United States Patent
Wilson et al.

(10) Patent No.: US 10,357,563 B2
(45) Date of Patent: Jul. 23, 2019

(54) METHODS AND COMPOSITION FOR NEUTRALIZATION OF INFLUENZA

(71) Applicant: The University of Chicago, Chicago, IL (US)

(72) Inventors: Patrick C. Wilson, Chicago, IL (US); Carole J. Henry Dunand, Chicago, IL (US)

(73) Assignee: The University of Chicago, Chicago, IL (US)

( * ) Notice: Subject to any disclaimer, the term of this patent is extended or adjusted under 35 U.S.C. 154(b) by 102 days.

(21) Appl. No.: 15/536,857

(22) PCT Filed: Dec. 17, 2015

(86) PCT No.: PCT/US2015/066281
§ 371 (c)(1),
(2) Date: Jun. 16, 2017

(87) PCT Pub. No.: WO2016/100615
PCT Pub. Date: Jun. 23, 2016

(65) Prior Publication Data
US 2017/0360931 A1     Dec. 21, 2017

Related U.S. Application Data

(60) Provisional application No. 62/093,870, filed on Dec. 18, 2014.

(51) Int. Cl.
| | | |
|---|---|---|
| *A61K 39/12* | (2006.01) | |
| *A61K 39/42* | (2006.01) | |
| *C07K 16/10* | (2006.01) | |
| *A61K 39/00* | (2006.01) | |

(52) U.S. Cl.
CPC .......... *A61K 39/42* (2013.01); *C07K 16/1018* (2013.01); *A61K 2039/505* (2013.01); *C07K 2317/21* (2013.01); *C07K 2317/33* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,676,980 A | 6/1987 | Segal et al. |
| 4,816,567 A | 3/1989 | Cabilly et al. |
| 4,831,175 A | 5/1989 | Gansow et al. |
| 4,946,778 A | 8/1990 | Ladner et al. |
| 5,260,203 A | 11/1993 | Ladner et al. |
| 2012/0039899 A1 | 2/2012 | Olsen et al. |
| 2012/0076726 A1 | 3/2012 | Gellerfors et al. |

FOREIGN PATENT DOCUMENTS

| | | |
|---|---|---|
| WO | WO 1988001649 A1 | 3/1988 |
| WO | WO 2011056997 A1 | 5/2011 |
| WO | WO 2014194111 A1 | 12/2014 |

OTHER PUBLICATIONS

Baker et al., Protein Structure Predication and Structural Genomics, Science (2001) vol. 294, No. 5540, pp. 93-96. (Year: 2001).*
Attwood, T. The Babel of Bioinformatics, Science (2000) vol. 290, No. 5491, pp. 471-473. (Year: 2000).*
AIR, Sequence relationships among the hemagglutinin genes of 12 subtypes of influenza A virus, Proc Natl Acad Sci, vol. 78(12), pp. 7639-7643, 1981.
Arnon et al. (1985) Monoclonal Antibodies for Immunotargeting of Drugs in Cancer Therapy, in Monoclonal Antibodies and Cancer Therapy, ed.
Baldwin et al. "Monoclonal Antibodies for Cancer Detection and Therapy" in Academic Press, New York, 1985, pp. 303-316.
Belser et al., Pathogenesis and transmission of avian influenza A (H7N9) virus in ferrets and mice, Nature, vol. 501, pp. 556-560, 2013.
Brandenburg et al., Mechanisms of Hemagglutinin Targeted Influenza Virus Neutralization, PLoS One, vol. 8(12), 14 pages, 2013.
Chothia et al., Canonical Structures for the Hypervariable Regions of Immunoglobulins, J Mol Biol, vol. 196, pp. 901-917, 1987.
Chothia et al., Conformations of immunoglobulin hypervariable regions, Nature, vol. 342, pp. 877-883, 1989.
Clackson et al., Making antibody fragments using phage display libraries, Nature, vol. 352, pp. 624-628, 1991.
Corti et al., A Neutralizing Antibody Selected from Plasma Cells That Binds to Group 1 and Group 2 Influenza A Hemagglutinins, Science, vol. 333(6044), pp. 850-856, 2011.
Corti et al., Heterosubtypic neutralizing antibodies are produced by individuals immunized with a seasonal influenza vaccine, J Clin Invest, vol. 120(5), pp. 1663-1673, 2010.
Crotty et al., Tracking human antigen-specific memory B cells: a sensitive and generalized ELISPOT system. Journal of immunological methods. 2004;286(1-2):111-22.
Dryefus et al. Highly Conserved Protective Epitopes on Influenza B Viruses, Science. 2012;337(6100):1343-8.
Ekiert et al. A Highly Conserved Neutralizing Epitope on Group 2 Influenza A Viruses. Science. 2011;333(6044):843-50.
Ekiert et al. Cross-neutralization of influenza A viruses mediated by a single antibody loop. Nature. 2012; 489(7417):526-32.
Ekiert et al., Antibody recognition of a highly conserved influenza virus epitope. Science.2009;324(5924):246-51.
Fodor et al., Rescue of Influenza A Virus from Recombinant DNA, J Virol, vol. 73(11), pp. 9679-9682, 1999.
Fouchier et al., Avian influenza A virus (H7N7) associated with human conjunctivitis and a fatal case of acute respiratory distress syndrome., Proc Natl Acad Sci, vol. 101(5), pp. 1356-1361, 2004.
Friesen et al., A common solution to group 2 influenza virus neutralization, Proc Natl Acad Sci, vol. 111(1), pp. 445-450, 2014.

(Continued)

*Primary Examiner* — Michelle S Horning
(74) *Attorney, Agent, or Firm* — Casimir Jones SC; David W. Staple

(57) ABSTRACT

Provided herein are compositions useful for neutralization of influenza virus, and methods of use and manufacture thereof. In particular, compositions comprising antibodies that are cross-reactive with multiple influenza strains are provided, as well as methods of treatment and prevention of influenza infection therewith.

20 Claims, 21 Drawing Sheets

Specification includes a Sequence Listing.

(56) References Cited

OTHER PUBLICATIONS

Gao et al., Human Infection with a Novel Avian-Origin Influenza A (H7N9) Virus, N Engl J Med, vol. 368(20), pp. 1888-1897, 2013.
Hai et al., Influenza A(H7N9) virus gains neuraminidase inhibitor resistance without loss of in vivo virulence or transmissibility, Nature Communications, vol. 4(2854), 9 pages, 2013.
Hai et al., Influenza Viruses Expressing Chimeric Hemagglutinins: Globular Head and Stalk Domains Derived from Different Subtypes, J Virol, vol. 86(10), pp. 5774-5781, 2012.
Hellstrom et al. (1987)"Antibodies for Drug Delivery," in Controlled Drug Delivery, ed. Robinson et al. (2d ed; Marcel Dekker, Inc.), pp. 623-653.
Hensley et al. Hemagglutinin Receptor Binding Avidity Drives Influenza A Virus Antigenic Drift. Science. 2009;326(5953):734-6.
Hirst et al. Novel Avian Influenza H7N3 Strain Outbreak, British Columbia, Emerg Infect Dis. 2004;10(12):2192-5.
Hirst et al., Novel Avian Influenza H7N3 Strain Outbreak, British Columbia, Emerg Infect Dis, vol. 10(12), pp. 2192-2195, 2004.
Hu et al., Association between adverse clinical outcome in human disease caused by novel influenza A H7N9 virus and sustained viral shedding and emergence of antiviral resistance, Lancet, vol. 381(9885), pp. 2273-2279, 2013.
Hudson et al., Engineered antibodies, Nat Med, vol. 9(1), pp. 129-134, 2003.
Kapczynski et al., Characterization of the 2012 Highly Pathogenic Avian Influenza H7N3 Virus Isolated from Poultry in an Outbreak in Mexico: Pathobiology and Vaccine Protection, J Virol, vol. 87(16), pp. 9086-9096, 2013.
Kaur et al. Targeting B cell responses in universal influenza vaccine design, Trends in immunology. 2011; 32(11):524-31.
Kohler et al. (1975) "Continuous cultures of fused cells secreting antibody of predefined specificity." Nature 256: 495-499.
Krammer et al., An H7N1 Influenza Virus Vaccine Induces Broadly Reactive Antibody Responses against H7N9 in Humans, CVI, vol. 21(8), pp. 1153-1163, 2014.
Krammer et al., Divergent H7 Immunogens Offer Protection from H7N9 Virus Challenge, J Virol, vol. 88(8), pp. 3976-3985, 2014.
Krammer et al., H3 Stalk-Based Chimeric Hemagglutinin Influenza Virus Constructs Protect Mice from H7N9 Challenge, J Virol, vol. 88(4), pp. 2340-2343, 2014.
Li et al., Pandemic H1N1 influenza vaccine induces a recall response in humans that favors broadly cross-reactive memory B cells, Proc Natl Acad Sci, vol. 109(23), pp. 9047-9052, 2012.
Margine et al. Expression of Functional Recombinant Hemagglutinin and Neuraminidase Proteins from the Novel H7N9 Influenza Virus Using the Baculovirus Expression System, Journal of visualized experiments: JoVE. 201381:e51112.
Margine et al., Hemagglutinin Stalk-Based Universal Vaccine Constructs Protect against Group 2 Influenza A Viruses, J Virol, vol. 87(19), pp. 10435-10446, 2013.
Margine et al., H3N2 Influenza Virus Infection Induces Broadly Reactive Hemagglutinin Stalk Antibodies in Humans and Mice, J Virol, vol. 87(8), pp. 4728-4737, 2013.
Marks et al., By-passing Immunization: Human Antibodies from V-gene Libraries Displayed on Phage, J Mol Biol, vol. 222, pp. 581-597, 1991.
Martin, Remington's Pharmaceutical Sciences, 15th Ed., Mack Publ. Co., Easton, Pa. (1975).
Medina et al., Influenza A viruses: new research developments, Nat Rev Microbiol, vol. 9(8), pp. 590-603, 2011.

Morens et al., H7N9 Avian Influenza A Virus and the Perpetual Challenge of Potential Human Pandemicity, Mbio, vol. 4(4), e00445-13, 2013.
O'Donnell, Antibody Pressure by a Human Monoclonal Antibody Targeting the 2009 Pandemic H1N1 Virus Hemagglutinin Drives the Emergence of a Virus with Increased Virulence in Mice, Mbio, vol. 3(3), 10 pages, 2012.
Pauli et al., *Staphylococcus aureus* infection induces protein A-mediated immune evasion in humans, J Exp Med, 9 pages, 2014.
Pinchera et al. "Analysis, Results, and Future Prospective of the Therapeutic Use of Radiolabeled Antibody in Cancer Therapy," in Monoclonal Antibodies for Cancer Detection and Therapy, ed. pp. 475-506 (Editrice Kurds, Milano, Italy, 1985).
Quinlivan et al., Attenuation of Equine Influenza Viruses through Truncations of the NS1 Protein, J Virol, vol. 79(13), pp. 8431-8439, 2005.
Ramos et al., H7N9 influenza viruses interact preferentially with a2,3-linked sialic acids and bind weakly to a2,6-linked sialic acids, the Journal of General Virology, vol. 94, pp. 2417-2423, 2013.
Reisfeld et al. Monoclonal Antibodies and Cancer Therapy. (Alan R. Liss, Inc.), pp. 243-256; ed.
Shaw M.L. et al. Orthomyxoviruses. In: Knipe DM, Howley PM, eds. Fields Virology. Philadelphia, Pennsylvania, USA: Lippincott Williams and Wilkins; 2013.
Smith et al., Rapid generation of fully human monoclonal antibodies specific to a vaccinating antigen. Nat Protoc. 2009;4(3):372-84.
Sui et al. Structural and functional bases for broad-spectrum neutralization of avian and human influenza A viruses. Nat Struct Mol Biol. 2009;16(3):265-73.
Tan et al., Characterization of a Broadly Neutralizing Monoclonal Antibody That Targets the Fusion Domain of Group 2 Influenza A Virus Hemagglutinin, J Virol, vol. 88(23), pp. 13580-13592, 2014.
Thomson et al., Pandemic H1N1 influenza infection and vaccination in humans induces cross-protective antibodies that target the hemagglutinin stem, Frontiers in Immunology, vol. 3(87), 19 pages, 2012.
Thorpe et al. The Preparation and Cytotoxic Properties of Antibody-Toxin Conjugates. Immunol. Rev. 62:119-158, 1982.
Throsby et al., Heterosubtypic Neutralizing Monoclonal Antibodies Cross-Protective against H5N1 and H1N1 Recovered from Human IgM+ Memory B Cells, PloS One, vol. 3(12), e3942, 2008.
Wang et al., Broadly Protective Monoclonal Antibodies against H3 Influenza Viruses following Sequential Immunization with Different Hemagglutinins, PLoS Pathogens, vol. 6(2), e1000796, 2010.
Watanabe et al. Characterization of H7N9 influenza A viruses isolated from humans. 15 Nature. 2013.
Wilson P.C. et al. Tools to therapeutically harness the human antibody response. Nature reviews Immunology. 2012;12(10):709-19.
Wrammert et al. Broadly cross-reactive antibodies dominate the human B cell response against 2009 pandemic H1N1 influenza virus infectionNature. 2008;453(7195):667-71.
Wrammert et al., Broadly cross-reactive antibodies dominate the human B cell response against 2009 pandemic H1N1 influenza virus infection, J Exp Med, vol. 208(1), pp. 181-193, 2011.
Xu et al. Preferential Recognition of Avian-Like Receptors in Human Influenza A H7N9 Viruses. Science. 2013;342(6163):1230-5.
Zhang et al., H7N9 Influenza Viruses Are Transmissible in Ferrets by Respiratory Droplet, Science, vol. 341, pp. 410-414, 2013.
International Search Report of related PCTUS2015066281, dated May 2, 2016, 20 pages.

* cited by examiner

FIG. 9B

METHODS AND COMPOSITION FOR NEUTRALIZATION OF INFLUENZA

CROSS-REFERENCE TO RELATED APPLICATIONS

The present invention is a § 371 U.S. National Entry of PCT/US2015/066281, filed Dec. 17, 2015, which claims the priority benefit of U.S. Provisional Patent Application 62/093,870, filed Dec. 18, 2014, each of which is incorporated by reference in its entirety.

FIELD

Provided herein are compositions useful for neutralization of influenza virus, and methods of use and manufacture thereof. In particular, compositions comprising antibodies that are cross-reactive with multiple influenza strains are provided, as well as methods of treatment and prevention of influenza infection therewith.

BACKGROUND

The emergence and seasonal persistence of pathogenic H7N9 influenza viruses in China have raised concerns about the pandemic potential of these viruses due to their ability to bind to human sialic acid receptors and the development of resistance to neuraminidase inhibitors without a loss in fitness. Widespread H7N9 infections throughout the human population have a substantial impact on global health and economies. The pre-existing immunity to H7N9 strains from prior exposure to circulating human influenza viruses or influenza vaccination has yet to be investigated.

Influenza A viruses evade the human immune system by changing the antigenic regions of their surface glycoproteins using two mechanisms: antigenic drift (point mutations) and antigenic shift (gene segment reassortments) (Shaw M L and Palese P. Orthomyxoviruses. In: Knipe D M, Howley P M, eds. Fields Virology. Philadelphia, Pa., USA: Lippincott Williams and Wilkins; 2013; herein incorporated by reference in its entirety). Antigenic variation is further increased by divergent evolution as influenza virus strains recirculate continually among different host reservoirs, especially humans and avian species. The hemagglutinin (HA) glycoprotein is the main target of neutralizing antibodies, and is composed of an immuno-dominant globular head domain and a stalk domain (Kaur et al. Trends in immunology. 2011; 32(11):524-31; herein incorporated by reference in its entirety). HA subtypes are classified into two groups based on their antigenic properties, amino acid sequences and structural features (Air. Proc Natl Acad Sci USA. 1981; 78(12):7639-43; herein incorporated by reference in its entirety). Group 2 Influenza A viruses includes the H3 subtype, which further contains the seasonal H3N2 human strains, and the H7 subtype which contains highly pathogenic avian influenza (HPAI) A viruses (Medina & Garcia-Sastre. Nat Rev Microbiol. 2011; 9(8):590-603; herein incorporated by reference in its entirety). Previously, infections with H7 viruses, through exposure to poultry, generally resulted in uncomplicated influenza illness and/or mild conjunctivitis (demonstrated for H7N3), with only one fatal case observed during an outbreak in the Netherlands (H7N7) (Hirst et al. Emerg Infect Dis. 2004; 10(12):2192-5; Fouchier et al. Proc Natl Acad Sci USA. 2004; 101(5):1356-61; herein incorporated by reference in their entireties). However in 2013, a novel influenza A virus (H7N9), the reassortment product of various avian strains, emerged in China. This virus, associated with a high frequency of fatal human disease, appeared to have a wide dispersion and the potential for human-to-human transmission (Gao et al. N Engl J Med. 2013; 368(20):1888-97; Belser et al. Pathogenesis and transmission of avian influenza A (H7N9) virus in ferrets and mice. Nature. 2013; Watanabe et al. Characterization of H7N9 influenza A viruses isolated from humans. Nature. 2013; Morens et al. MBio. 2013; 4(4); Hu et al. Lancet. 2013; 381(9885):2273-9; Zhang et al. Science. 2013; 341(6144):410-4; herein incorporated by reference in their entireties). Although most publicized in 2013 (153 cases), the H7N9 virus shows a seasonal pattern with most infections occurring during the winter season. The incidence of infection continues to increase with nearly twice as many new H7N9 infections (301 cases) reported in 2014, totaling 454 cases, according to the World Health Organization as of July, 2014. These cases occurred in 12 provinces of China and imported cases in Malaysia and Taiwan. The incidence of H7N9 infections combined with its abilities to bind to human receptor orthologs and to develop resistance to neuraminidase inhibitors without fitness loss has raised concerns about the pandemic potential of H7N9 virus (Xu et al. Science. 2013; 342(6163):1230-5; Ramos et al. The Journal of general virology. 2013; 94 (Pt 11):2417-23; Hai et al. Nature communications. 2013; 4(2854.); herein incorporated by reference in their entireties).

SUMMARY

Provided herein are compositions useful for neutralization of influenza virus, and methods of use and manufacture thereof. In particular, compositions comprising antibodies that are cross-reactive with multiple influenza strains are provided, as well as methods of treatment and prevention of influenza infection therewith.

Provided herein, in part, is the isolation from individuals vaccinated with influenza vaccine (e.g., seasonal influenza vaccine, vaccine against H1 influenza strains, vaccine against H3 influenza strains, etc.) of antibodies (e.g., antibodies that bind to HA, human antibodies, monoclonal antibodies, antibody fragments, etc.) that neutralize infection of more than one strains of influenza A virus (e.g., H7 and one or more additional strains), as well as novel epitopes to which the antibodies of the invention bind, and antibody fragments or modified antibodies based thereon. Accordingly, in one aspect, provided herein are antibodies and antigen binding fragments thereof that neutralize infection of more than one strain of influenza A virus.

In some embodiments, provided herein is an isolated antibody, or an antigen binding fragment thereof, that neutralizes infection of an H7 strain of influenza (e.g., H7N9). In another embodiment, an antibody or an antigen-binding fragment thereof also neutralizes infection of a H1 (e.g., H1N1) and/or H3 (e.g., H3N2) strain influenza A virus. In some embodiments, antibodies specifically bind to an epitope in the stalk region of influenza A hemagglutinin (HA).

In certain embodiments, provided herein is an antibody, or antigen binding fragment thereof, that neutralizes infection of an H7 strain of influenza A virus (e.g., and one or both of an H1 strain or H3 strain), wherein the antibody or fragment thereof is expressed by an immortalized B cell clone. In some embodiments, the antibody or fragment thereof is expressed from the immunoglobulin genes of an isolated B cell.

In another aspect, provided herein are nucleic acids comprising a polynucleotide encoding an antibody or antibody fragment described herein. In some embodiments, provided herein are vectors comprising a nucleic acid molecule or a cell expressing an antibody or an antigen binding fragment described herein. In some embodiments, provided herein are cells comprising a vector described herein. In some embodiments, provided herein are isolated or purified immunogenic polypeptides comprising an epitope that binds to an antibody or antigen binding fragment described herein.

Also provided herein are pharmaceutical compositions comprising an antibody or an antigen binding fragment described herein, a nucleic acid molecule described herein, a vector comprising a nucleic acid molecule described herein, a cell expressing an antibody or an antibody fragment described herein, a cell comprising a vector, or an immunogenic polypeptide; and a pharmaceutically acceptable diluent or carrier. In some embodiments, provided herein are pharmaceutical compositions comprising a first antibody or an antigen binding fragment thereof, and a second antibody, or an antigen binding fragment thereof, wherein the first antibody is an antibody described herein, and the second antibody is any antibody, or antigen binding fragment thereof, that neutralizes influenza A or influenza B virus infection.

The use of an antibody or an antigen binding fragment thereof, a nucleic acid, a vector comprising a nucleic acid, a cell expressing a vector, an isolated or purified immunogenic polypeptide comprising an epitope that binds to an antibody or antibody fragment described herein, or a pharmaceutical composition: (i) in the manufacture of a medicament for the treatment of influenza A virus infection, (ii) in a vaccine, (iii) in a composition for inducing an immune response, (iv) in diagnosis of influenza A virus infection, or (v) for research purposes, is also within the scope described herein.

In another aspect, provided herein are methods of preventing, treating or reducing influenza A virus infection or lowering the risk of influenza A virus infection comprising administering to a subject in need thereof, a therapeutically effective amount of an antibody or an antigen binding antibody fragment of the invention.

Also provided herein are epitopes which specifically binds to an antibody of or an antigen binding fragment described herein, for use (i) in therapy, (ii) in the manufacture of a medicament for treating influenza A virus infection, (iii) as a vaccine, or (iv) in screening for ligands able to neutralize influenza A virus infection.

In some embodiments, provided herein are binding agents (e.g., antibodies or antibody fragments) comprising: (a) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with a polypeptide encoded by one of SEQ ID NOs. 1-3 and 33; and (b) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with a polypeptide encoded by one of SEQ ID NOs. 4-6 and 34; wherein the binding agent exhibits similar influenza epitope-binding characteristics to an antibody comprising a heavy and light chain variable regions with 100% sequence identity to those encoded by one of SEQ ID NOs: 1:4, 2:5, 3:6, or 33:34, respectively. In some embodiments, similar influenza epitope-binding characteristics comprises: (1) binding to the same epitope, (2) binding to the same epitope with the same affinity (e.g., as measured by immunofluorescence, ELISA, etc.), binding to the same epitope with less than 10-fold reduction (e.g., 8-fold, 6-fold, 4-fold, 2-fold, etc.) in affinity (e.g., as measured by immunofluorescence, ELISA, etc.). In some embodiments, the polypeptide of (a) and the polypeptide of (b) comprise first and second polypeptides. In some embodiments, the binding agent is a monoclonal antibody or monobody. In some embodiments, the binding agent is an antibody fragment (e.g., Fab, F(ab')$_2$, Fab'. scFv, di-scFv, sdAb, etc.). In some embodiments, the polypeptide of (a) and the polypeptide of (b) are a single polypeptide chain. In some embodiments, the binding agent comprises a binding affinity for an epitope or epitopes displayed on two or more different virus strains. In some embodiments, the two or more different virus strains are influenza strains (e.g., influenza A stains). In some embodiments, a first influenza strain is an H7 strain. In some embodiments, the first influenza strain is an H7N9 strain. In some embodiments, the second influenza strain is an H1 or H3 strain. In some embodiments, the second influenza strain is an H1N1 strain. In some embodiments, the second influenza strain is an H3N2 strain.

In some embodiments, provided herein are binding agents (e.g., antibodies or antibody fragments) comprising: (a) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with one of SEQ ID NOs. 7-9 and 35; and (b) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with one of SEQ ID NOs. 10-12 and 36; wherein the binding agent exhibits similar influenza epitope-binding characteristics to an antibody comprising a heavy and light chain variable regions with 100% sequence identity to those encoded by one of SEQ ID NOs: 7:10, 8:11, 9:12, or 35:36, respectively. In some embodiments, the binding agent is an artificial polypeptide (e.g., not a naturally-occurring sequence or a fragment of a naturally-occurring sequence).

In some embodiments, provided herein are binding agents (e.g., antibodies or antibody fragments) comprising: (a) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with a polypeptide encoded by SEQ ID NO. 1; and (b) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with a polypeptide encoded by SEQ ID NO. 4; and wherein the binding agent exhibits similar influenza epitope-binding characteristics to an antibody comprising a heavy and light chain variable regions with 100% sequence identity to those encoded by SEQ ID NO. 1 and SEQ ID NO. 4, respectively. In some embodiments, the binding agent is an artificial polypeptide (e.g., not a naturally-occurring sequence or a fragment of a naturally-occurring sequence).

In some embodiments, provided herein are binding agents (e.g., antibodies or antibody fragments) comprising: (a) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with SEQ ID NO. 7; and (b) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with SEQ ID NO. 10; and wherein the binding agent exhibits similar influenza epitope-binding characteristics to an antibody comprising a heavy and light chain variable regions with 100% sequence identity to SEQ ID NO. 7 and SEQ ID NO. 10, respectively. In some embodiments, the binding agent is an artificial polypeptide (e.g., not a naturally-occurring sequence or a fragment of a naturally-occurring sequence).

In some embodiments, provided herein are binding agents (e.g., antibodies or antibody fragments) comprising: (a) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with a polypeptide encoded by SEQ ID NO. 2; and (b) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with a polypeptide encoded by SEQ ID NO. 5; and wherein the binding agent exhibits similar influenza epitope-binding characteristics to an antibody comprising a heavy and light chain variable regions with 100% sequence identity to those encoded by SEQ ID NO. 2 and SEQ ID NO. 5, respectively. In some embodiments, the binding agent is an artificial polypeptide (e.g., not a naturally-occurring sequence or a fragment of a naturally-occurring sequence).

In some embodiments, provided herein are binding agents (e.g., antibodies or antibody fragments) comprising: (a) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with SEQ ID NO. 8; and (b) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with SEQ ID NO. 11; and wherein the binding agent exhibits similar influenza epitope-binding characteristics to an antibody comprising a heavy and light chain variable regions with 100% sequence identity to SEQ ID NO. 8 and SEQ ID NO. 11, respectively. In some embodiments, the binding agent is an artificial polypeptide (e.g., not a naturally-occurring sequence or a fragment of a naturally-occurring sequence).

In some embodiments, provided herein are binding agents (e.g., antibodies or antibody fragments) comprising: (a) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with a polypeptide encoded by SEQ ID NO. 3; and (b) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with a polypeptide encoded by SEQ ID NO. 6; and wherein the binding agent exhibits similar influenza epitope-binding characteristics to an antibody comprising a heavy and light chain variable regions with 100% sequence identity to those encoded by SEQ ID NO. 3 and SEQ ID NO. 6, respectively. In some embodiments, the binding agent is an artificial polypeptide (e.g., not a naturally-occurring sequence or a fragment of a naturally-occurring sequence).

In some embodiments, provided herein are binding agents (e.g., antibodies or antibody fragments) comprising: (a) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with SEQ ID NO. 9; and (b) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with SEQ ID NO. 12; and wherein the binding agent exhibits similar influenza epitope-binding characteristics to an antibody comprising a heavy and light chain variable regions with 100% sequence identity to SEQ ID NO. 9 and SEQ ID NO. 12, respectively. In some embodiments, the binding agent is an artificial polypeptide (e.g., not a naturally-occurring sequence or a fragment of a naturally-occurring sequence).

In some embodiments, provided herein are binding agents (e.g., antibodies or antibody fragments) comprising: (a) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with a polypeptide encoded by SEQ ID NO. 33; and (b) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with a polypeptide encoded by SEQ ID NO. 34; and wherein the binding agent exhibits similar influenza epitope-binding characteristics to an antibody comprising a heavy and light chain variable regions with 100% sequence identity to those encoded by SEQ ID NO. 33 and SEQ ID NO. 34, respectively. In some embodiments, the binding agent is an artificial polypeptide (e.g., not a naturally-occurring sequence or a fragment of a naturally-occurring sequence).

In some embodiments, provided herein are binding agents (e.g., antibodies or antibody fragments) comprising: (a) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with SEQ ID NO. 35; and (b) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with SEQ ID NO. 36; and wherein the binding agent exhibits similar influenza epitope-binding characteristics to an antibody comprising a heavy and light chain variable regions with 100% sequence identity to SEQ ID NO. 35 and SEQ ID NO. 36, respectively. In some embodiments, the binding agent is an artificial polypeptide (e.g., not a naturally-occurring sequence or a fragment of a naturally-occurring sequence).

In some embodiments, provided herein is a binding agent (e.g., antibody, antibody fragment, etc.) that neutralizes infection of an H7 strain of influenza A virus and an H1 or H3 strain of influenza and comprises: (i) a heavy chain variable region comprising a CDR1 of SEQ ID NO: 13, a CDR2 of SEQ ID NO: 14 and CDR3 of SEQ ID NO: 15, and a light chain variable region comprising a CDR1 of SEQ ID NO: 22, a CDR2 of SEQ ID NO: 23 and CDR3 of SEQ ID NO: 24; (ii) a heavy chain variable region comprising a CDR1 of SEQ ID NO: 16, a CDR2 of SEQ ID NO: 17 and CDR3 of SEQ ID NO: 18, and a light chain variable region comprising a CDR1 of SEQ ID NO: 25, a CDR2 of SEQ ID NO: 26 and CDR3 of SEQ ID NO: 27; (iii) a heavy chain variable region comprising a CDR1 of SEQ ID NO: 19, a CDR2 of SEQ ID NO: 20 and CDR3 of SEQ ID NO: 21, and a light chain variable region comprising a CDR1 of SEQ ID NO: 28, a CDR2 of SEQ ID NO: 29 and CDR3 of SEQ ID NO: 30; or (iv) a heavy chain variable region comprising a CDR1 of SEQ ID NO: 37, a CDR2 of SEQ ID NO: 38 and CDR3 of SEQ ID NO: 39, and a light chain variable region comprising a CDR1 of SEQ ID NO: 40, a CDR2 of SEQ ID NO: 41 and CDR3 of SEQ ID NO: 42.

In some embodiments, provided herein is a binding agent (e.g., antibody, antibody fragment, etc.) that neutralizes infection of an H7 strain of influenza A virus and an H1 or H3 strain of influenza and comprises: (i) a heavy chain variable region comprising a CDR1 with 70% or greater sequence identity (e.g., 70%, 75%, 80%, 85%, 90%, 95%, or more) with SEQ ID NO: 13, a CDR2 with 70% or greater sequence identity (e.g., 70%, 75%, 80%, 85%, 90%, 95%, or more) with SEQ ID NO: 14 and CDR3 with 70% or greater sequence identity (e.g., 70%, 75%, 80%, 85%, 90%, 95%, or more) with SEQ ID NO: 15, and a light chain variable region comprising a CDR1 with 70% or greater sequence identity (e.g., 70%, 75%, 80%, 85%, 90%, 95%, or more) with SEQ ID NO: 22, a CDR2 with 70% or greater sequence identity (e.g., 70%, 75%, 80%, 85%, 90%, 95%, or more) with SEQ ID NO: 23 and CDR3 with 70% or greater sequence identity with SEQ ID NO: 24; (ii) a heavy chain variable region comprising a CDR1 with 70% or greater sequence identity (e.g., 70%, 75%, 80%, 85%, 90%, 95%, or more) with SEQ ID NO: 16, a CDR2 with 70% or greater sequence identity (e.g., 70%, 75%, 80%, 85%, 90%, 95%, or more) with SEQ ID NO: 17 and CDR3 with 70% or greater sequence identity (e.g., 70%, 75%, 80%, 85%, 90%, 95%, or more) with SEQ ID NO: 18, and a light chain variable region comprising a CDR1 with 70% or greater sequence identity (e.g., 70%, 75%, 80%, 85%, 90%, 95%, or more) with SEQ ID NO: 25, a CDR2 with 70% or greater sequence identity (e.g., 70%, 75%, 80%, 85%, 90%, 95%, or more) with SEQ ID NO: 26 and CDR3 with 70% or greater sequence identity (e.g., 70%, 75%, 80%, 85%, 90%, 95%, or more) with SEQ ID NO: 27; (iii) a heavy chain variable region comprising a CDR1 with 70% or greater sequence identity (e.g., 70%, 75%, 80%, 85%, 90%, 95%, or more) with SEQ ID NO: 19, a CDR2 with 70% or greater sequence identity (e.g., 70%, 75%, 80%, 85%, 90%, 95%, or more) with SEQ ID NO: 20 and CDR3 with 70% or greater sequence identity (e.g., 70%, 75%, 80%, 85%, 90%, 95%, or more) with SEQ ID NO: 21, and a light chain variable region comprising a CDR1 with 70% or greater sequence identity (e.g., 70%, 75%, 80%, 85%, 90%, 95%, or more) with SEQ ID NO: 28, a CDR2 with 70% or greater sequence identity (e.g., 70%, 75%, 80%, 85%, 90%, 95%, or more) with SEQ ID NO: 29 and CDR3 with 70% or greater sequence identity (e.g., 70%, 75%, 80%, 85%, 90%, 95%, or more) with SEQ ID NO: 30; or (iv) a heavy chain variable region comprising a CDR1 with 70% or greater sequence identity (e.g., 70%, 75%, 80%, 85%, 90%, 95%, or more) with SEQ ID NO: 37, a CDR2 with 70% or greater sequence identity (e.g., 70%, 75%, 80%, 85%, 90%, 95%, or more) with SEQ ID NO: 38 and CDR3 with 70% or greater sequence identity (e.g., 70%, 75%, 80%, 85%, 90%, 95%, or more) with SEQ ID NO: 39, and a light chain variable region comprising a CDR1 with 70% or greater sequence identity (e.g., 70%, 75%, 80%, 85%, 90%, 95%, or more) with SEQ ID NO: 40, a CDR2 with 70% or greater sequence identity (e.g., 70%, 75%, 80%, 85%, 90%, 95%, or more) with SEQ ID NO: 41 and CDR3 with 70% or greater sequence identity (e.g., 70%, 75%, 80%, 85%, 90%, 95%, or more) with SEQ ID NO: 42.

In some embodiments, provided herein are polynucleotides comprising a portion with 70% or greater sequence identity with one or more of SEQ ID NOs: 1-6 and/or 33-34. In some embodiments, provided herein are polynucleotides encoding the binding agents (e.g., antibodies, antibody fragments, etc.) described herein. In some embodiments, provided herein are polynucleotides comprising a portion encoding a polypeptide with 70% or greater sequence identity (e.g., 70%, 75%, 80%, 85%, 90%, 95%, or more) with one or more of SEQ ID NOs: 7-12 and/or 35-36. In some embodiments, provided herein are polynucleotides comprising a portion encoding a heavy chain variable region polypeptide with 70% or greater sequence identity (e.g., 70%, 75%, 80%, 85%, 90%, 95%, or more) with of SEQ ID NO: 7 and comprising a CDR1 of SEQ ID NO: 13, a CDR2 of SEQ ID NO: 14 and CDR3 of SEQ ID NO: 15. In some embodiments, provided herein are polynucleotides comprising a portion encoding a heavy chain variable region polypeptide with 70% or greater sequence identity (e.g., 70%, 75%, 80%, 85%, 90%, 95%, or more) with SEQ ID NO: 8 and comprising a CDR1 of SEQ ID NO: 16, a CDR2 of SEQ ID NO: 17 and CDR3 of SEQ ID NO: 18. In some embodiments, provided herein are polynucleotides comprising a portion encoding a heavy chain variable region polypeptide with 70% or greater sequence identity (e.g., 70%, 75%, 80%, 85%, 90%, 95%, or more) with SEQ ID NO: 9 and comprising a CDR1 of SEQ ID NO: 19, a CDR2 of SEQ ID NO: 20 and CDR3 of SEQ ID NO: 21. In some embodiments, provided herein are polynucleotides comprising a portion encoding a heavy chain variable region polypeptide with 70% or greater sequence identity (e.g., 70%, 75%, 80%, 85%, 90%, 95%, or more) with SEQ ID NO: 35 and comprising a CDR1 of SEQ ID NO: 37, a CDR2 of SEQ ID NO: 38 and CDR3 of SEQ ID NO: 39. In some embodiments, provided herein are polynucleotides comprising a portion encoding a light chain variable region polypeptide with 70% or greater sequence identity (e.g., 70%, 75%, 80%, 85%, 90%, 95%, or more) with SEQ ID NO: 10 and comprising a CDR1 of SEQ ID NO: 22, a CDR2 of SEQ ID NO: 23 and CDR3 of SEQ ID NO: 24. In some embodiments, provided herein are polynucleotides comprising a portion encoding a light chain variable region polypeptide with 70% or greater sequence identity (e.g., 70%, 75%, 80%, 85%, 90%, 95%, or more) with SEQ ID NO: 11 and comprising a CDR1 of SEQ ID NO: 25, a CDR2 of SEQ ID NO: 26 and CDR3 of SEQ ID NO: 27. In some embodiments, provided herein are polynucleotides comprising a portion encoding a light chain variable region polypeptide with 70% or greater sequence identity (e.g., 70%, 75%, 80%, 85%, 90%, 95%, or more) with SEQ ID NO: 12 and comprising a CDR1 of SEQ ID NO: 28, a CDR2 of SEQ ID NO: 29 and CDR3 of SEQ ID NO: 30. In some embodiments, provided herein are polynucleotides comprising a portion encoding a light chain variable region polypeptide with 70% or greater sequence identity (e.g., 70%, 75%, 80%, 85%, 90%, 95%, or more) with SEQ ID NO: 36 and comprising a CDR1 of SEQ ID NO: 40, a CDR2 of SEQ ID NO: 41 and CDR3 of SEQ ID NO: 42.

In some embodiments, provided herein are pharmaceutical preparations, compositions, and formulations comprising the binding agents (e.g., antibodies, antibody fragments, etc.) described herein.

In some embodiments, provided herein are methods comprising administering a therapeutic dose of a pharmaceutical preparation, composition, and/or formulation described herein (e.g., comprising a binding agents (e.g., antibodies, antibody fragments, etc.) described herein) to a subject. In some embodiments, the subject is a human or non-human animal. In some embodiments, the subject is infected with influenza. In some embodiments, the subject is infected with at least one H7 strain of influenza. In some embodiments, the subject is at risk of influenza infection. In some embodiments, the binding agent is co-administered with one or more additional therapeutic agents. In some embodiments, the one or more additional therapeutic agents are selected from the group consisting of antivirals, immunologic agents, antibiotics, and agents for relieving symptoms of influenza infection.

In some embodiments, provided herein are methods of treating or preventing an H7 influenza virus infection comprising administering to a first subject an antibody generated by vaccination of a second subject with a vaccine against an H1 and/or H3 infection. In some embodiments, the antibody is a monoclonal antibody. In some embodiments, the antibody is an antibody fragment. In some embodiments, the antibody is produced by hybridoma, recombinant technology, and/or chemical synthesis. In some embodiments, the antibody administered to the first subject is a modified version of the antibody generated by vaccination of the second subject.

In some embodiments, provided herein are binding agents (e.g., antibodies, antibody fragments, etc.) that neutralize infection of an H7 strain of influenza A virus and an H1 and/or H3 strain of influenza, and bind the same epitope as one of: (i) the heavy chain variable sequence set forth in SEQ ID NO: 7, and the light chain variable sequence set forth in SEQ ID NO: 10; or (ii) the heavy chain variable sequence set forth in SEQ ID NO: 8, and the light chain variable sequence set forth in SEQ ID NO: 11; or (iii) the heavy chain variable sequence set forth in SEQ ID NO: 9, and the light chain variable sequence set forth in SEQ ID NO: 12, or (iv) the heavy chain variable sequence set forth in SEQ ID NO: 35, and the light chain variable sequence set forth in SEQ ID NO: 36. In some embodiments, the binding agent has an affinity for the epitope of at least $10^7$ $M^{-1}$.

In some embodiments, provided herein is a binding agent (e.g., antibody, antibody fragment, etc.) that neutralizes infection of an H7 strain of influenza A virus and an H1 or H3 strain of influenza and binds the same epitope as one of: (i) the heavy chain CDR1, CDR2 and CDR3 sequences as set forth in SEQ ID NO: 7, respectively, and the light chain CDR1, CDR2, and CDR3 sequences as set forth in SEQ ID NO: 10, respectively; or (ii) the heavy chain CDR1, CDR2 and CDR3 sequences as set forth in SEQ ID NO: 8, respectively, and the light chain CDR1, CDR2, and CDR3 sequences as set forth in SEQ ID NO: 11, respectively; or (iii) the heavy chain CDR1, CDR2 and CDR3 sequences as set forth in SEQ ID NO: 9, respectively, and the light chain CDR1, CDR2, and CDR3 sequences as set forth in SEQ ID NO: 12, respectively; or (iii) the heavy chain CDR1, CDR2 and CDR3 sequences as set forth in SEQ ID NO: 35, respectively, and the light chain CDR1, CDR2, and CDR3 sequences as set forth in SEQ ID NO: 36, respectively. In some embodiments, the binding agent has an affinity for the epitope of at least $10^7$ $M^{-1}$.

In some embodiments, provided herein is a binding agent (e.g., antibody, antibody fragment, etc.) that neutralizes infection of an H7 strain of influenza A virus and an H1 or H3 strain of influenza and binds the same epitope as one of: (i) a heavy chain variable region comprising a CDR1 of SEQ ID NO: 13, a CDR2 of SEQ ID NO: 14 and CDR3 of SEQ ID NO: 15, and a light chain variable region comprising a CDR1 of SEQ ID NO: 22, a CDR2 of SEQ ID NO: 23 and CDR3 of SEQ ID NO: 24; (ii) a heavy chain variable region comprising a CDR1 of SEQ ID NO: 16, a CDR2 of SEQ ID NO: 17 and CDR3 of SEQ ID NO: 18, and a light chain variable region comprising a CDR1 of SEQ ID NO: 25, a CDR2 of SEQ ID NO: 26 and CDR3 of SEQ ID NO: 27; (iii) a heavy chain variable region comprising a CDR1 of SEQ ID NO: 19, a CDR2 of SEQ ID NO: 20 and CDR3 of SEQ ID NO: 21, and a light chain variable region comprising a CDR1 of SEQ ID NO: 28, a CDR2 of SEQ ID NO: 29 and CDR3 of SEQ ID NO: 30; or (iv) a heavy chain variable region comprising a CDR1 of SEQ ID NO: 37, a CDR2 of SEQ ID NO: 38 and CDR3 of SEQ ID NO: 39, and a light chain variable region comprising a CDR1 of SEQ ID NO: 40, a CDR2 of SEQ ID NO: 41 and CDR3 of SEQ ID NO: 42. In some embodiments, the binding agent has an affinity for the epitope of at least $10^7$ $M^{-1}$.

In some embodiments, provided herein is the use of the antibodies or antibody fragments described herein for the treatment of influence infection. In some embodiments, provided herein are the antibodies or antibody fragments described herein for use as a medicament. In some embodiments, provided herein are antibodies or antibody fragments for use in the treatment of influenza infection. In some embodiments, provided herein is the use of the antibodies or antibody fragments described herein for the manufacture of a medicament for the treatment of influenza infection.

Figure 4A:
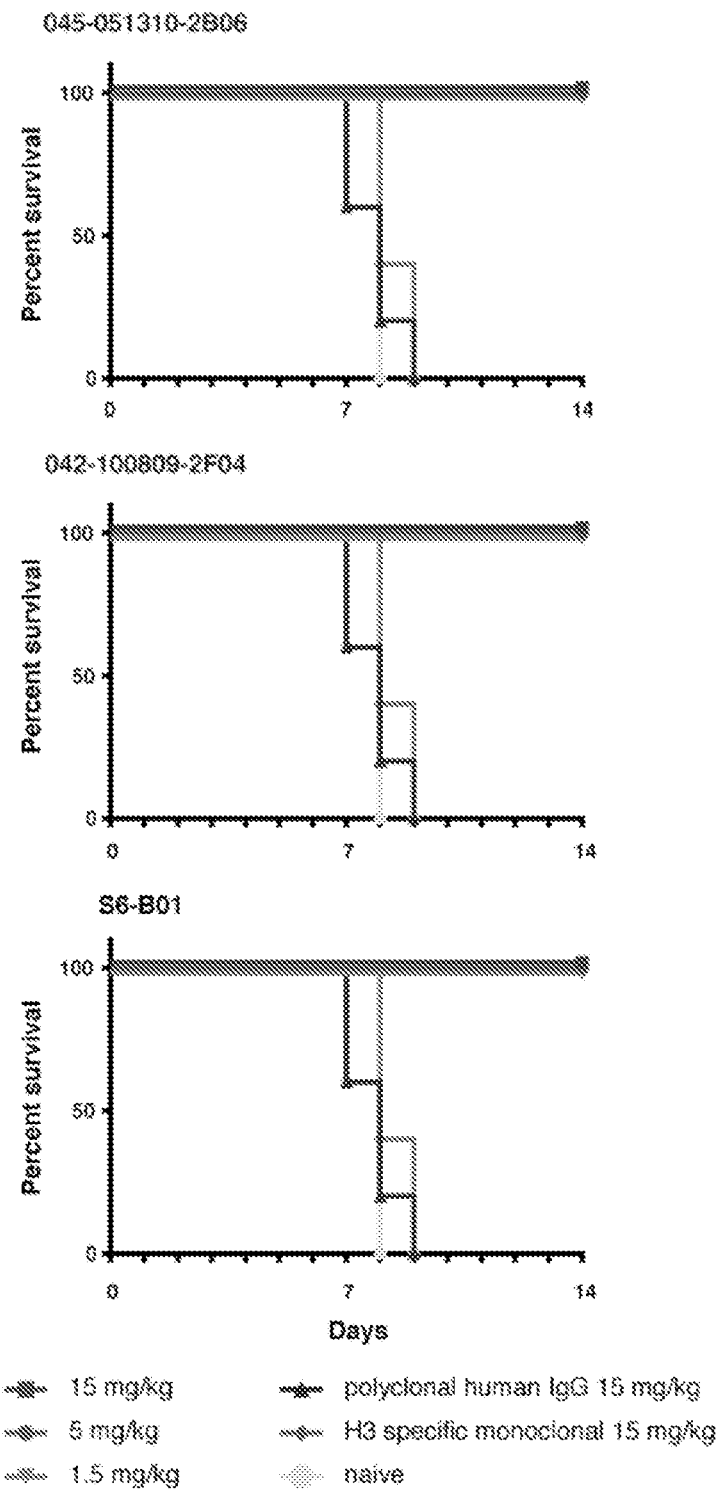
Figure 4B:
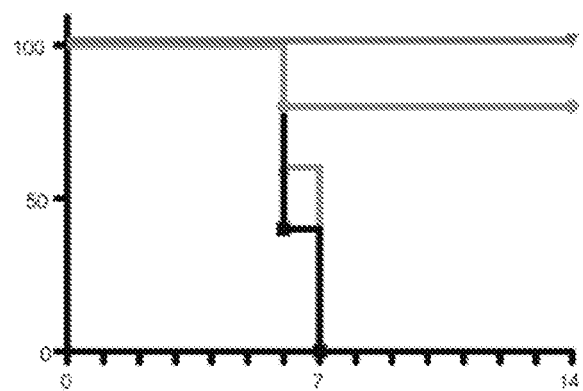
Figure 4B:
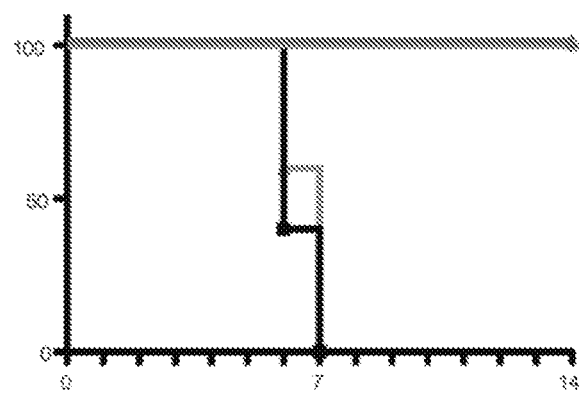
Figure 4B:
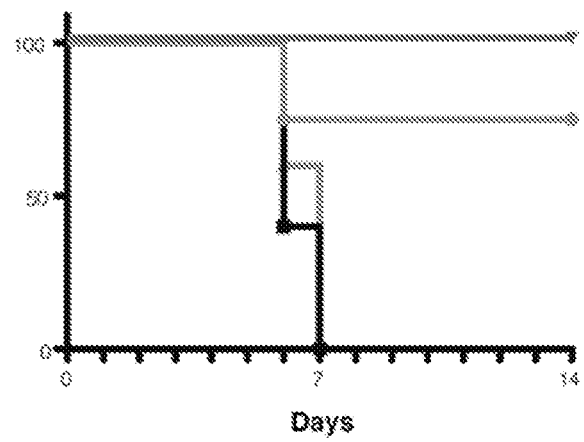

FIGS. 4A-B. Passive transfer of the H7N9 neutralizing antibodies in mice. Survival curves of (A) 6-8 week old female BALB/c mice (5 per experimental condition) injected intraperitoneally with 1.5, 5 or 15 mg/kg of antibody and then infected with a lethal dose (7.5 LD50) of A/Shanghai/1/2013 virus (B) 6-8 week old female BALB/c mice (5 per experimental condition) infected with a lethal dose (7.5 LD50) of A/Shanghai/1/2013 virus and then injected intraperitoneally with 15 mg/kg of antibody (24 or 72 hours postinfection).

Figure 5:
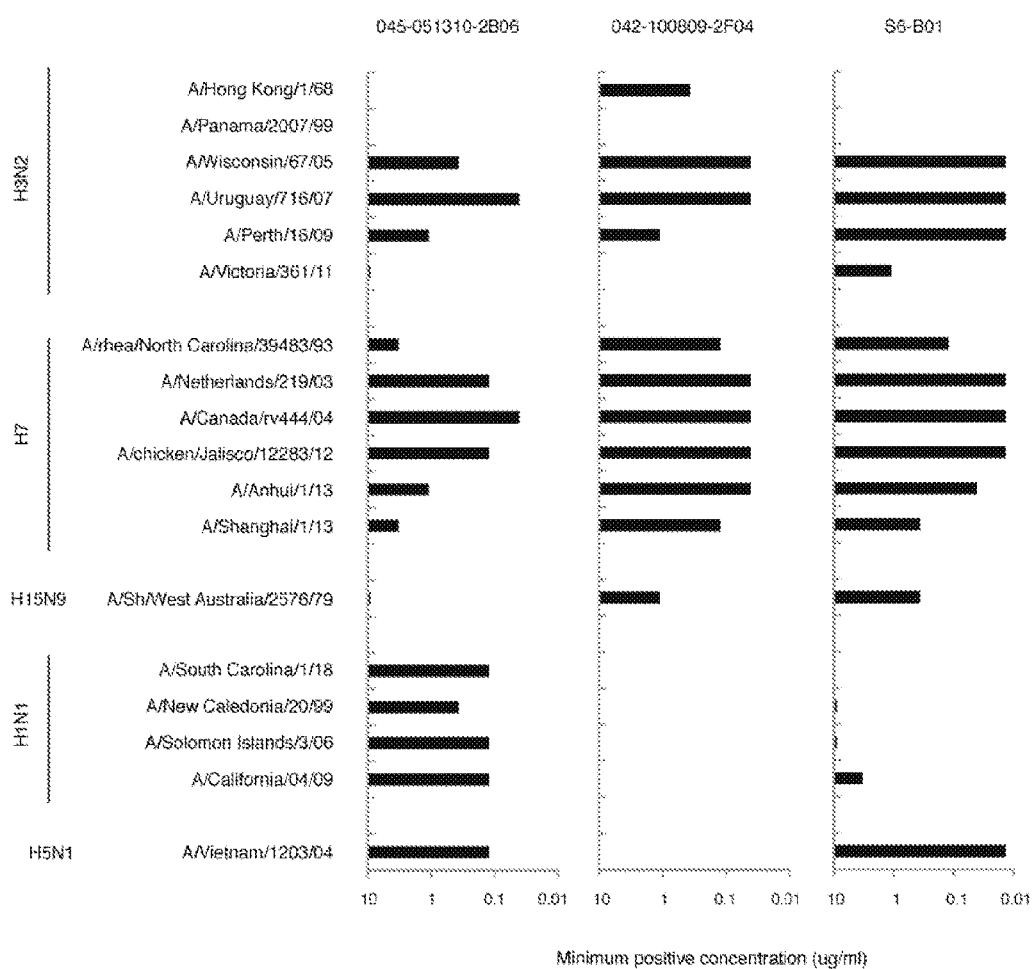

FIG. 5. Virus strain cross-reactivity of the H7N9 neutralizing antibodies. Binding of the antibodies to multiple influenza A recombinant HA proteins from group 2 (H3N2 and H7) and group 1 (H1N1 and H5N1) was assessed by ELISA. The minimum positive concentration was defined as two standard deviations above mean binding of randomly chosen naïve B cell antibodies, as previously described (16). Data are representative of independent experiments.

Figure 6:
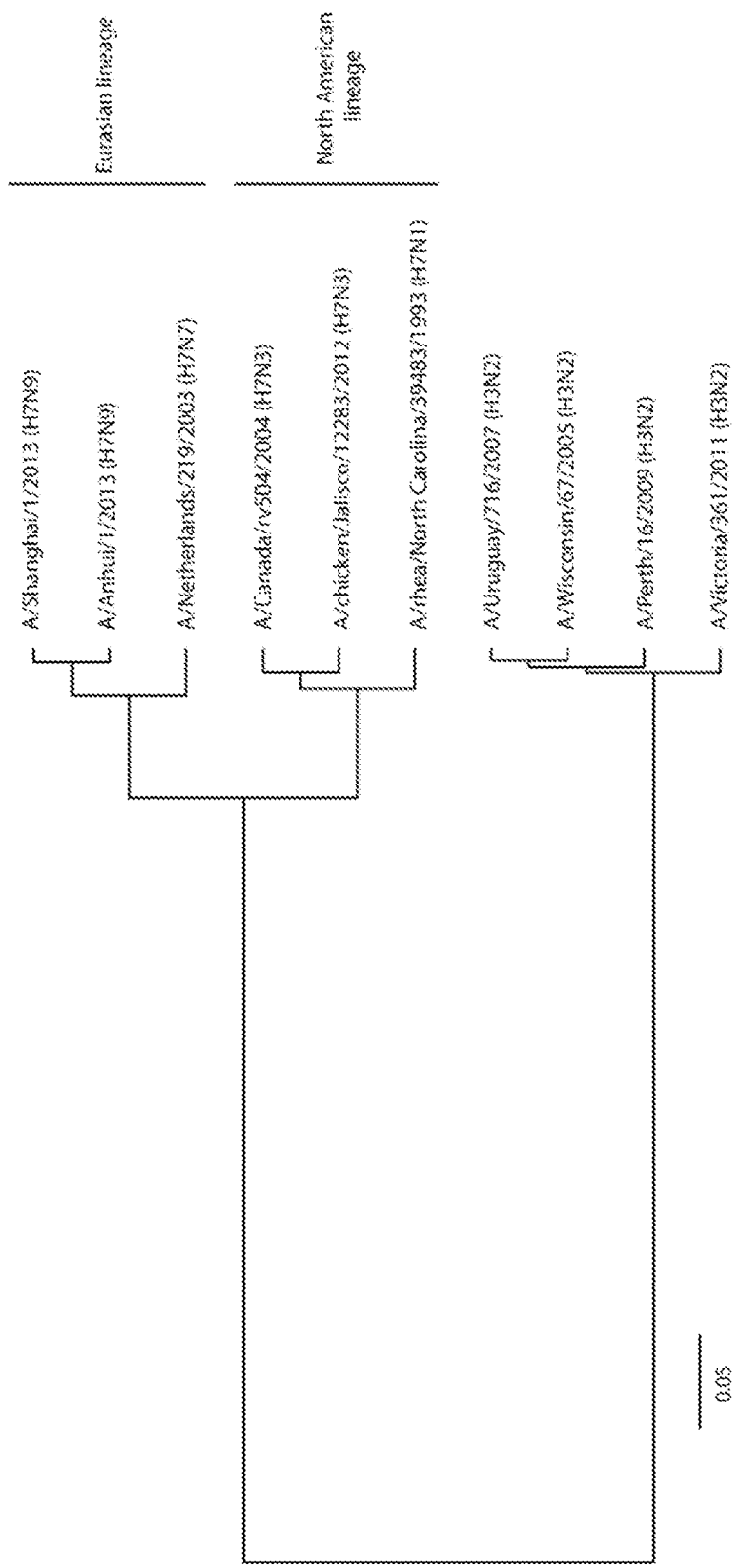

FIG. 6. Phylogeny of selected H7 and H3N2 subtype hemagglutinins. H7 subtypes from both the Eurasian and North American lineages are shown. Multiple alignments were performed using the CLUSTALW algorithm. Phylogenetic rooted tree was constructed using the neighbor-joining method and was visualized using FigTree v1.4.0 software, with amino acid sequences of full length HAs.

Figure 7A:
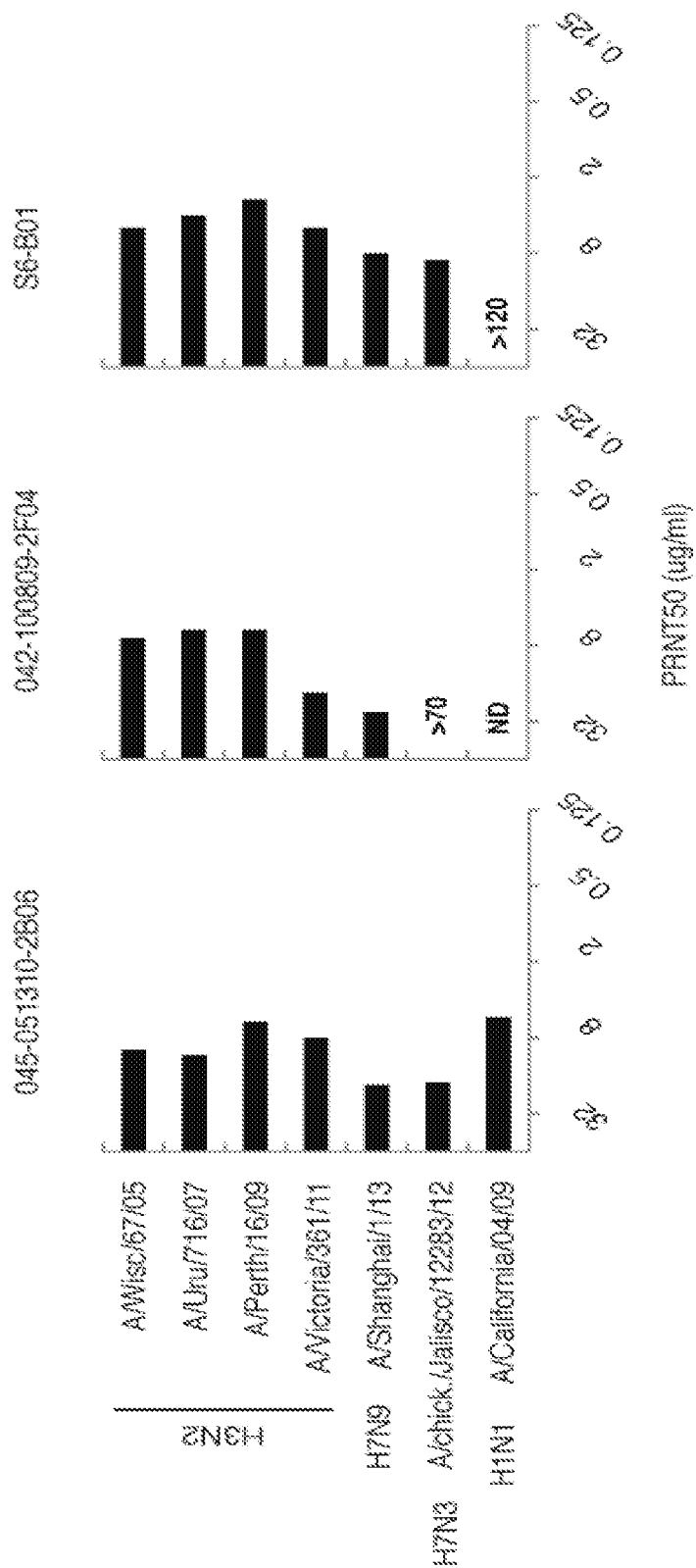
Figure 7B:
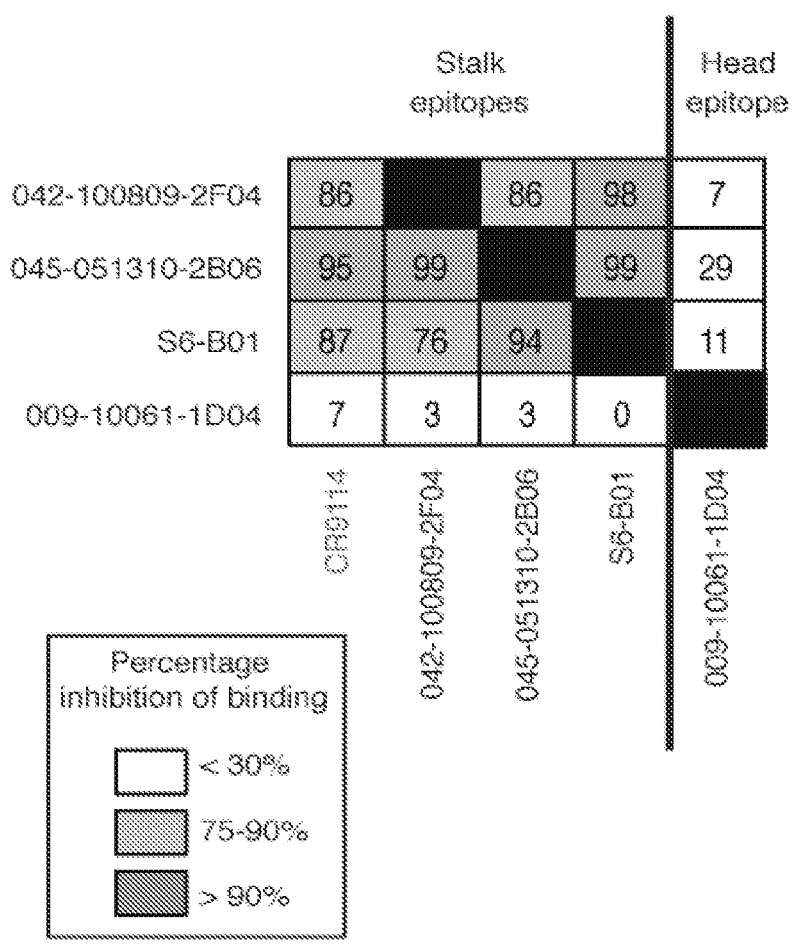
Figure 7C:
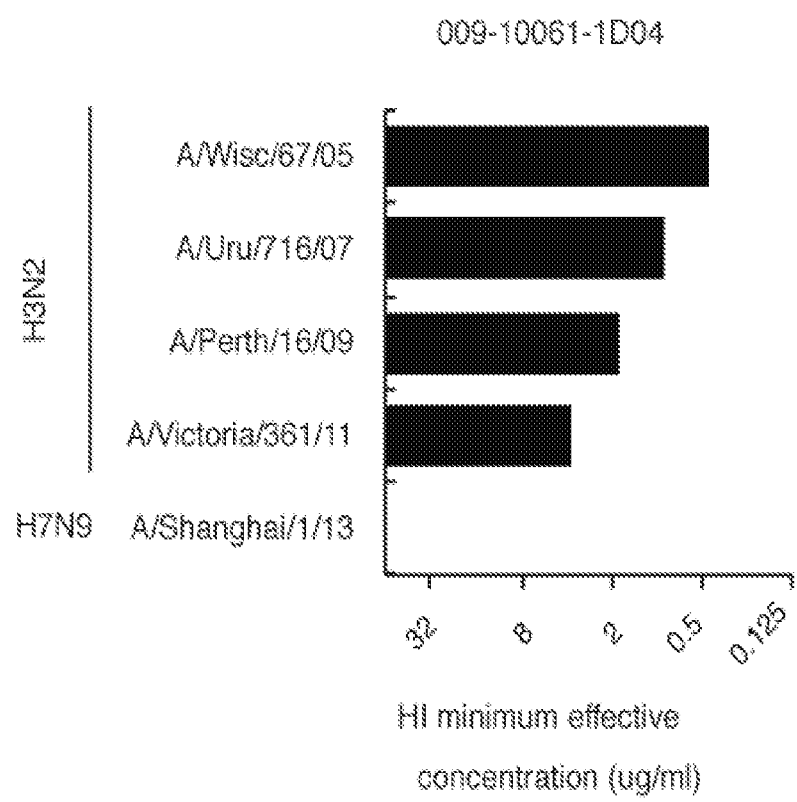

FIGS. 7A-C. Functional analysis of the H7N9 neutralizing antibodies. (A) In vitro neutralization by plaque reduction assay. PRNT50 values in µg/ml are displayed. The data shown are means of 4 replicates (2 independent experiments). (B) Competition ELISA was used to confirm binding of the antibodies to epitopes either on the stalk or the globular head of HA. The percentage of competition of each antibody against the other neutralizing antibodies and the CR9114 antibody, using the A/Uruguay/716/2007 recombinant HA protein, is shown. The percentage here is the mean of three independent experiments. (C) Hemagglutination inhibition assay (HAI) with various H3N2 strains and the H7N9 A/Shanghai/1/13 strain. Minimum effective concentration is shown in µg/ml and results are displayed only for the antibody 009-10061-1D04, as the H7N9 neutralizing antibodies are negative on this assay. Data are representative of independent experiments.

Figure 8A:
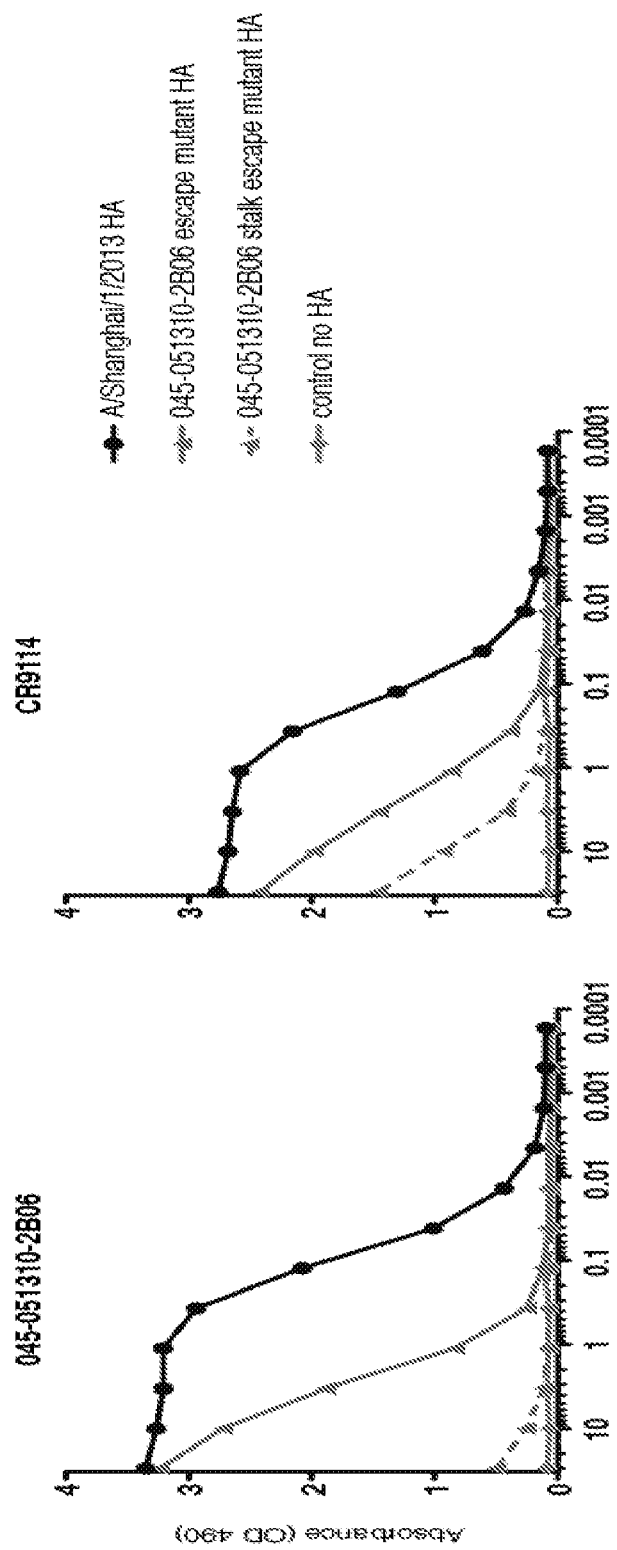
Figure 8B:
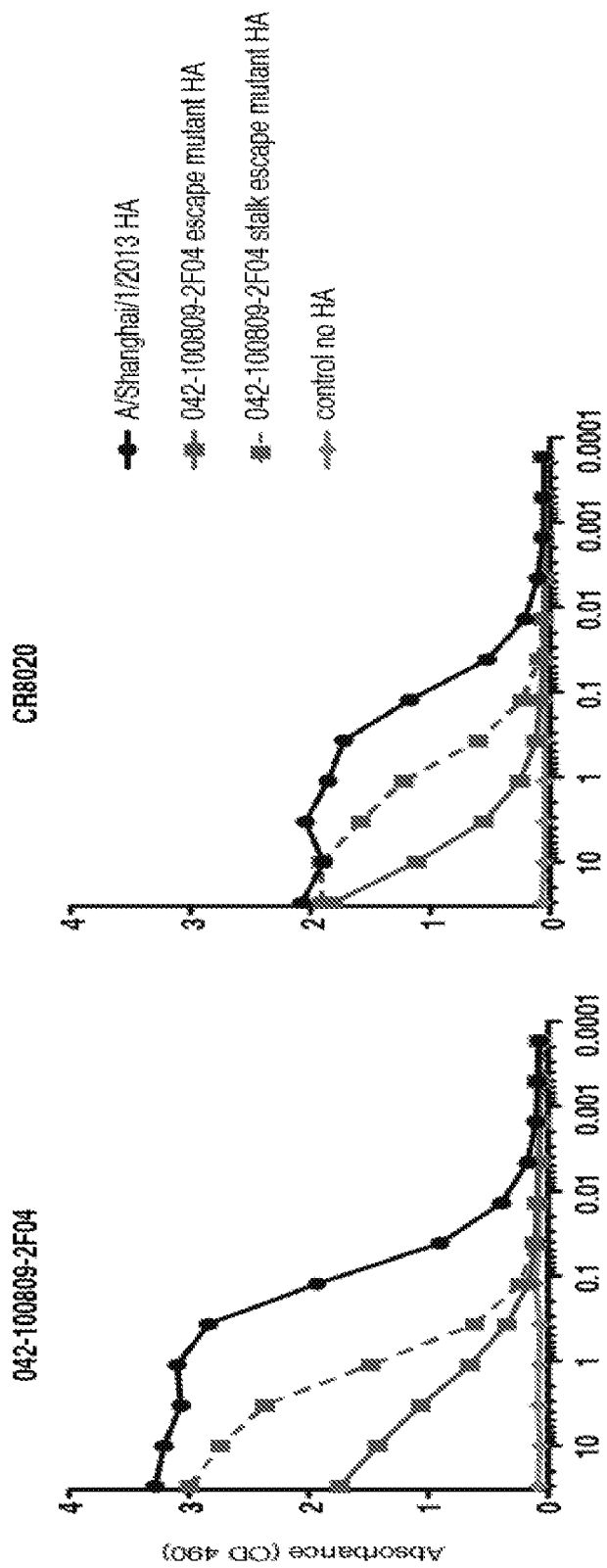
Figure 8C:
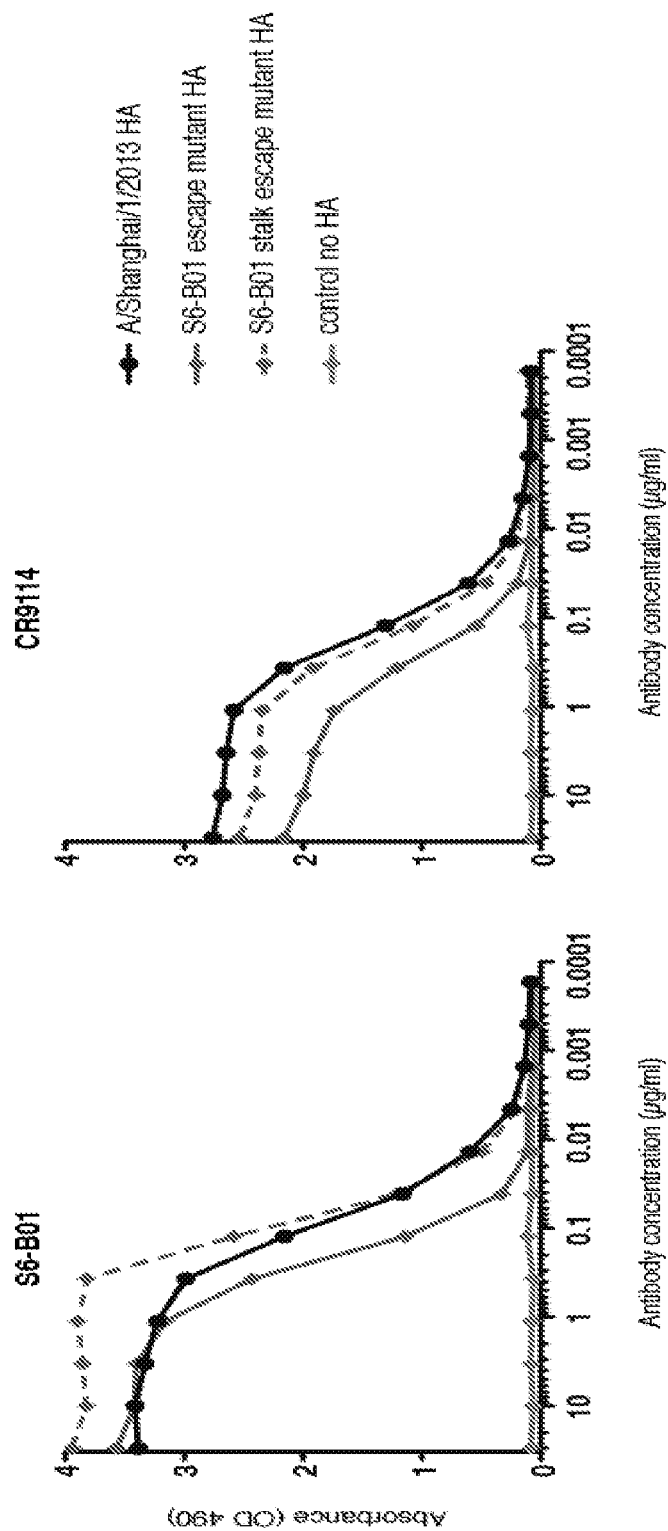

FIGS. 8A-C. Binding analysis of the antibodies to recombinant HA escape mutants. Binding of the antibodies 045-051310-2B06, 042-100809-2F04 and S6-B01 to the corresponding HA mutants (both head and stalk mutations or stalk-only mutants) was assessed by ELISA. CR9114 and CR8020 antibodies were also tested against the mutant HAs. Absorbance was read at 490 nm. Reading above 3 is outside the linear range.

Figure 9A:
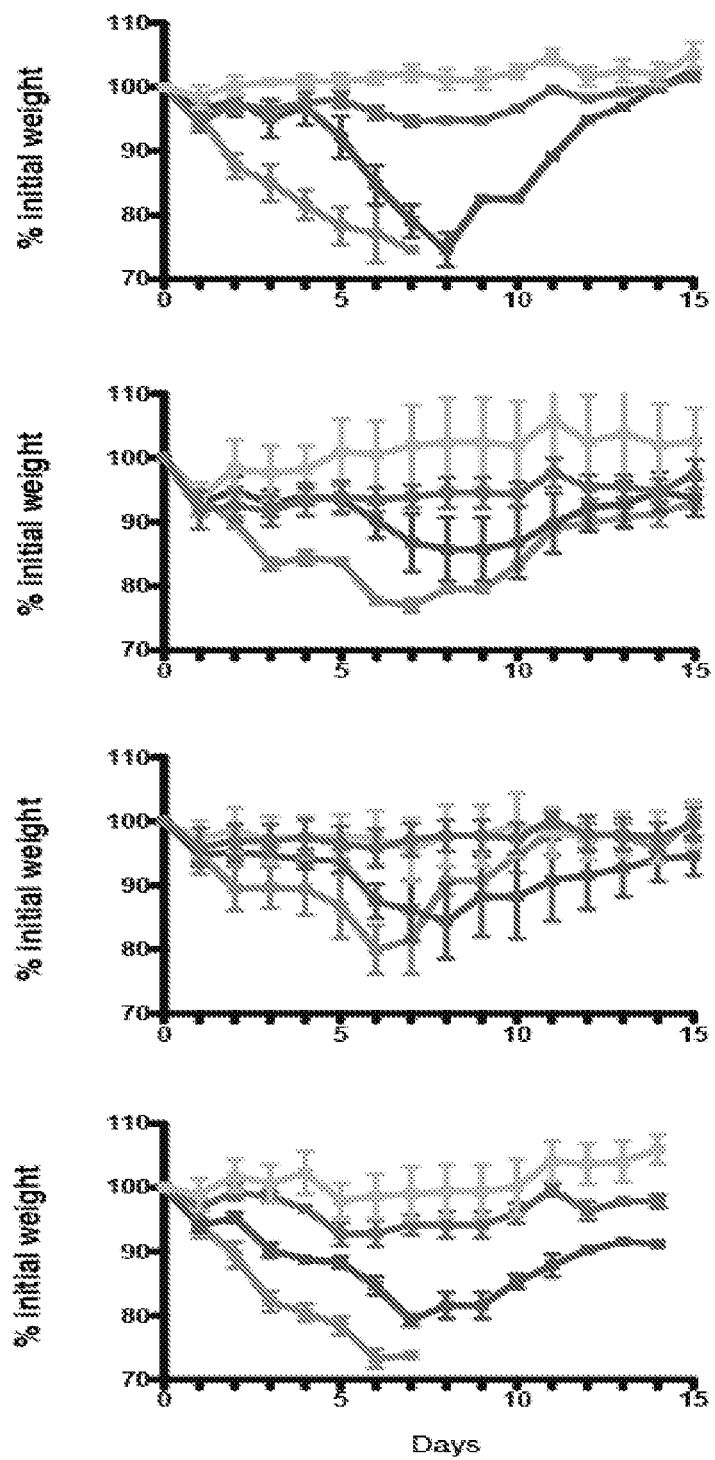
Figure 9B:
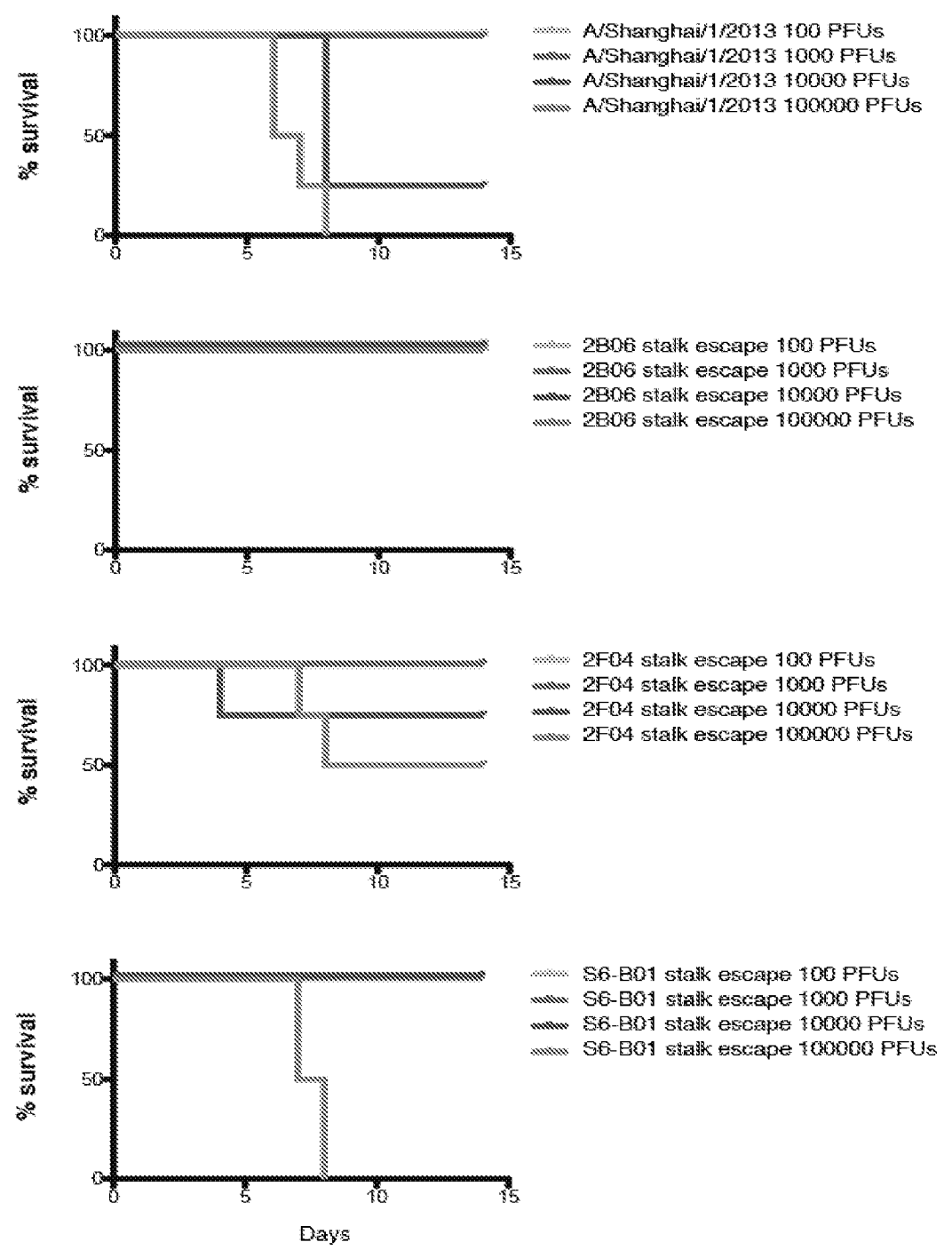

FIGS. 9A-B. Pathogenicity of the stalk escape mutant viruses in vivo. Mice were challenged with escalating doses, ranging from 100 to 100,000 plaque forming units (PFU) of A/Shanghai/1/2013 H7N9 wild-type virus, 045-051310-2B06 stalk escape mutant virus, 042-100809-2F04 stalk escape mutant virus, or S6-B01 stalk escape mutant virus. (A) Percentage of initial body weight (mean±SEM) and (B) percent survival (mean±SEM) are plotted for each escape mutants.

Figure 10:
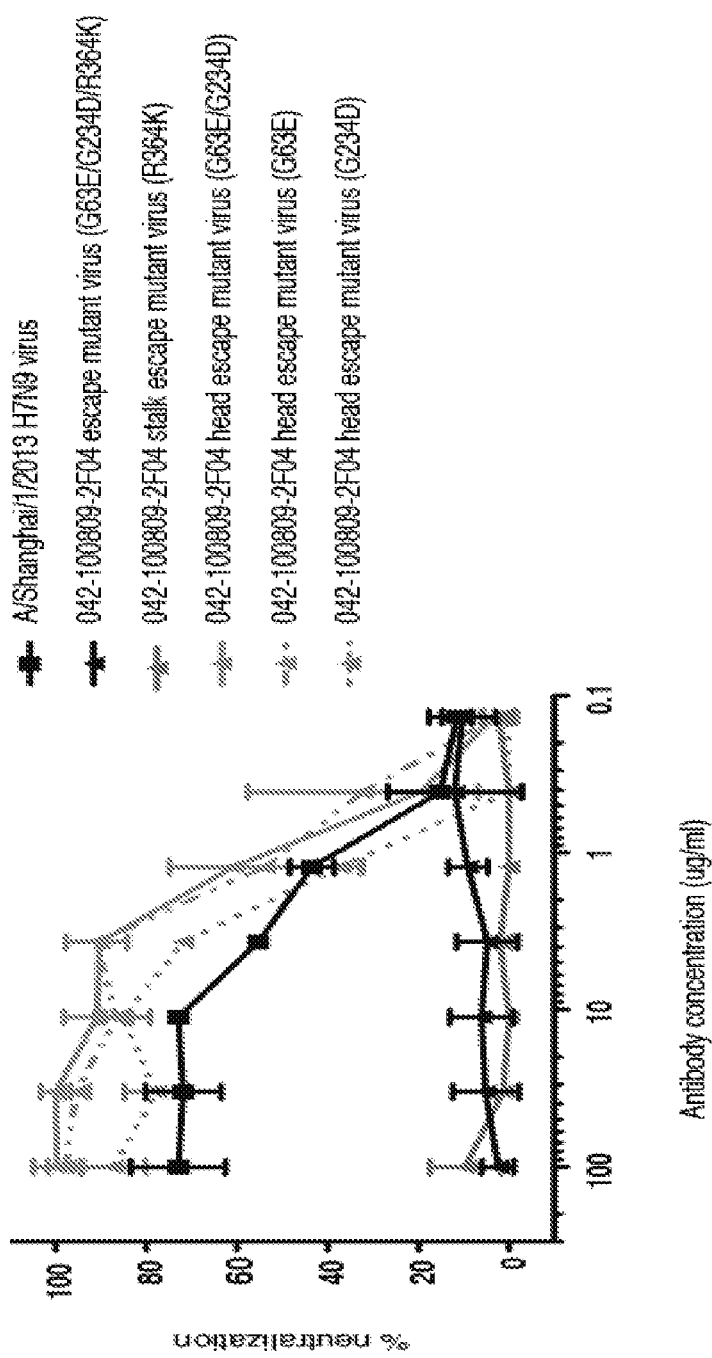

FIG. 10. Characterization of point-mutant escape viruses for the 042-100809-2F04 antibody. In vitro microneutralization assay using the 5 different escape mutant viruses generated for the 042-100809-2F04 antibody. A/Shanghai/1/2013 (H7N9) viruses were used as a control.

Figure 11:
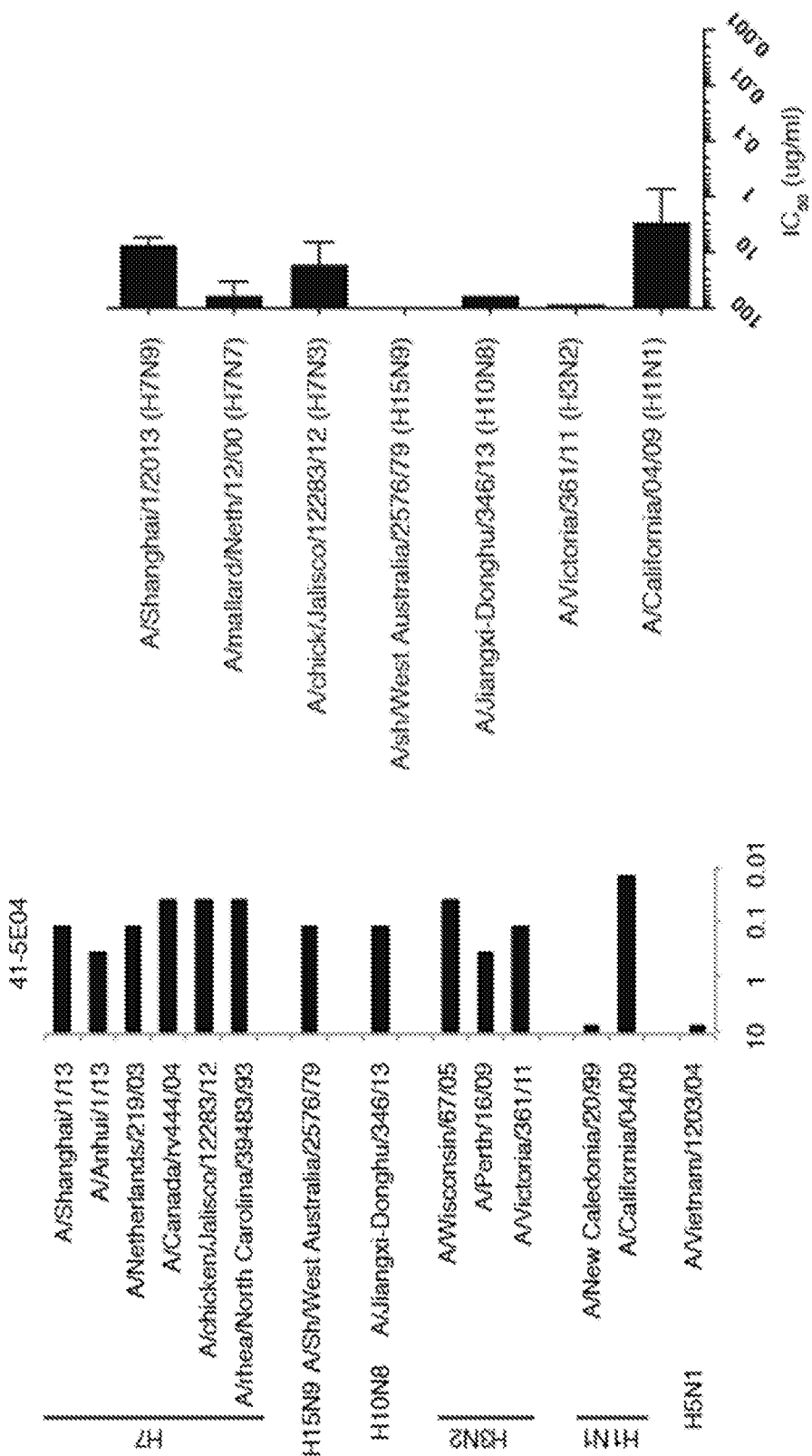

FIG. 11. (A) Binding of 41-5E04 to multiple recombinant HA proteins by ELISA. Minimum positive concentrations (µg/ml) are represented. B. Neutralization capacity of 41-5E04 determined by in vitro microneutralization assay (IC50 in µg/ml).

Figure 12:
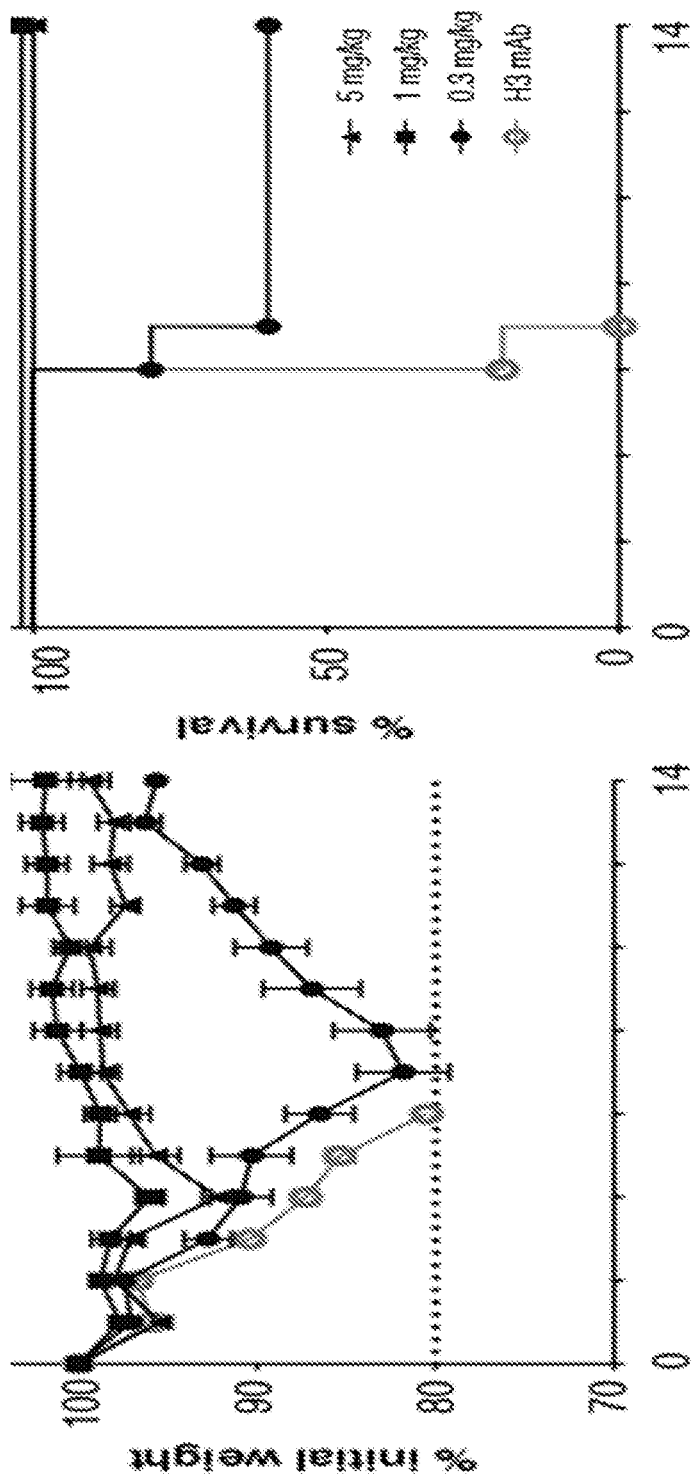

FIG. 12. Antibody 41-5E04 was tested for protection against an H7N9 challenge in mice. Percent of initial weight and percent survival are plotted. Values represent mean±SEM (n=5 mice per group). Mice that received an H3-reactive but not H7-reactive antibody died at day 6 after the challenge.

DEFINITIONS

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the term "antibody" refers to a whole antibody molecule or a fragment thereof (e.g., fragments such as Fab, Fab', and F(ab')$_2$), it may be a polyclonal or monoclonal antibody, a chimeric antibody, a humanized antibody, a human antibody, etc.

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, $V_H$, and three constant regions, $C_{H1}$, $C_{H2}$, and $C_{H3}$. The $V_H$ domain is at the amino-terminus of the heavy chain, and the $C_{H3}$ domain is at the carboxy-terminus. In a native antibody, a light chain comprises a variable region, $V_L$, and a constant region, $C_L$. The variable region of the light chain is at the amino-terminus of the light chain. In a native antibody, the variable regions of each light/heavy chain pair typically form the antigen binding site. The constant regions are typically responsible for effector function.

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. H3, for example, in certain instances, can be as short as two amino acid residues or greater than 26. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia, C., and Lesk, A. M. (1987) J. Mol. Biol. 196:901-917; or Chothia, C. et al. Nature 342:878-883 (1989). In the present application, the term "CDR" refers to a CDR from either the light or heavy chain, unless otherwise specified.

As used herein, the term "heavy chain" refers to a polypeptide comprising sufficient heavy chain variable region sequence to confer antigen specificity either alone or in combination with a light chain.

As used herein, the term "light chain" refers to a polypeptide comprising sufficient light chain variable region sequence to confer antigen specificity either alone or in combination with a heavy chain.

As used herein, when an antibody or other entity "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ $M^{-1}$ (e.g., $>10^7$ $M^{-1}$, $>10^8$ $M^{-1}$, $>10^9$ $M^{-1}$, $>10^{10}$ $M^{-1}$, $>10^{11}$ $M^{-1}$, $>10^{12}$ $M^{-1}$, $>10^{13}$ $M^{-1}$, etc.). In certain such embodiments, an antibody is capable of binding different antigens so long as the different antigens comprise that particular epitope. In certain instances, for example, homologous proteins from different species may comprise the same epitope.

As used herein, the term "anti-influenza antibody" refers to an antibody which specifically recognizes an antigen and/or epitope presented by one or more strains of influenza virus. A "cross-reactive influenza antibody" refers to an antibody which specifically recognizes an antigen and/or epitope presented by more than one strain of influenza virus. For example, an "H3/H7 cross-reactive influenza antibody" or "H3/H7 cross-reactive antibody" specifically recognizes an antigen and/or epitope presented by H3 and H7 strains of influenza.

As used herein, the term "monoclonal antibody" refers to an antibody which is a member of a substantially homogeneous population of antibodies that specifically bind to the same epitope. In certain embodiments, a monoclonal antibody is secreted by a hybridoma. In certain such embodiments, a hybridoma is produced according to certain methods known to those skilled in the art. See, e.g., Kohler and Milstein (1975) Nature 256: 495-499; herein incorporated by reference in its entirety. In certain embodiments, a monoclonal antibody is produced using recombinant DNA methods (see, e.g., U.S. Pat. No. 4,816,567). In certain embodiments, a monoclonal antibody refers to an antibody fragment isolated from a phage display library. See, e.g., Clackson et al. (1991) Nature 352: 624-628; and Marks et al. (1991) J. Mol. Biol. 222: 581-597; herein incorporated by reference in their entireties. The modifying word "monoclonal" indicates properties of antibodies obtained from a substantially-homogeneous population of antibodies, and does not limit a method of producing antibodies to a specific method. For various other monoclonal antibody production techniques, see, e.g., Harlow and Lane (1988) Antibodies: A Laboratory Manual (Cold Spring Harbor Laboratory, Cold Spring Harbor, N.Y.); herein incorporated by reference in its entirety.

As used herein, the term "antibody fragment" refers to a portion of a full-length antibody, including at least a portion antigen binding region or a variable region. Antibody fragments include, but are not limited to, Fab, Fab', $F(ab')_2$, Fv, scFv, Fd, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody). produced by recombinant DNA techniques, or chemical polypeptide synthesis.

For example, a "Fab" fragment comprises one light chain and the $C_{H1}$ and variable region of one heavy chain. The heavy chain of a Fab molecule cannot form a disulfide bond with another heavy chain molecule. A "Fab'" fragment comprises one light chain and one heavy chain that comprises additional constant region, extending between the $C_{H1}$ and $C_{H2}$ domains. An interchain disulfide bond can be formed between two heavy chains of a Fab' fragment to form a "$F(ab')_2$" molecule.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen.

Other antibody fragments will be understood by skilled artisans.

As used herein, the term "chimeric antibody" refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from a non-human animal fused to a constant region of an antibody derived from a human.

A "humanized" antibody refers to a non-human antibody that has been modified so that it more closely matches (in amino acid sequence) a human antibody. A humanized antibody is thus a type of chimeric antibody. In certain embodiments, amino acid residues outside of the antigen binding residues of the variable region of the non-human antibody are modified. In certain embodiments, a humanized antibody is constructed by replacing all or a portion of a complementarity determining region (CDR) of a human antibody with all or a portion of a CDR from another antibody, such as a non-human antibody, having the desired antigen binding specificity. In certain embodiments, a humanized antibody comprises variable regions in which all or substantially all of the CDRs correspond to CDRs of a non-human antibody and all or substantially all of the framework regions (FRs) correspond to FRs of a human antibody. In certain such embodiments, a humanized antibody further comprises a constant region (Fc) of a human antibody.

The term "human antibody" refers to a monoclonal antibody that contains human antibody sequences and does not contain antibody sequences from a non-human animal. In certain embodiments, a human antibody may contain synthetic sequences not found in native antibodies. The term is not limited by the manner in which the antibodies are made. For example, in various embodiments, a human antibody may be made in a transgenic mouse, by phage display, by human B-lymphocytes, or by recombinant methods.

As used herein, the term "natural antibody" refers to an antibody in which the heavy and light chains of the antibody have been made and paired by the immune system of a multicellular organism. For example, the antibodies produced by the antibody-producing cells isolated from a first animal immunized with an antigen are natural antibodies. Natural antibodies contain naturally-paired heavy and light chains. The term "natural human antibody" refers to an antibody in which the heavy and light chains of the antibody have been made and paired by the immune system of a human subject.

Native human light chains are typically classified as kappa and lambda light chains. Native human heavy chains are typically classified as mu, delta, gamma, alpha, or epsilon, and define the antibody's isotype as IgM, IgD, IgG, IgA, and IgE, respectively. IgG has subclasses, including, but not limited to, IgG1, IgG2, IgG3, and IgG4. IgM has subclasses including, but not limited to, IgM1 and IgM2. IgA has subclasses including, but not limited to, IgA1 and IgA2. Within native human light and heavy chains, the variable and constant regions are typically joined by a "J" region of about 12 or more amino acids, with the heavy chain also including a "D" region of about 10 more amino acids. See, e.g., Fundamental Immunology (1989) Ch. 7 (Paul, W., ed., 2nd ed. Raven Press, N.Y.); herein incorporated by reference in its entirety.

The term "neutralizing antibody" or "antibody that neutralizes" refers to an antibody that reduces at least one activity of a polypeptide comprising the epitope to which the antibody specifically binds. In certain embodiments, a neutralizing antibody reduces an activity in vitro and/or in vivo. In some embodiments, by neutralizing the polypeptide comprising the epitope, the neutralizing antibody inhibits the capacity of the organism (or virus) displaying the epitope. For example, an "influenza neutralizing antibody" reduces the capacity of one or more strains of influenza to infect a subject.

The term "antigen-binding site" refers to a portion of an antibody capable of specifically binding an antigen. In certain embodiments, an antigen-binding site is provided by one or more antibody variable regions.

The term "epitope" refers to any polypeptide determinant capable of specifically binding to an immunoglobulin or a T-cell receptor. In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three dimensional structural characteristics (e.g., a "conformational" epitope) and/or specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

As used herein, the term "artificial" refers to compositions and systems that are designed or prepared by man, and are not naturally occurring. For example, an artificial polypeptide (e.g., antibody or antibody fragment) or nucleic acid is one comprising a non-natural sequence (e.g., a polypeptide without 100% identity with a naturally-occurring protein or a fragment thereof).

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("Octan"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "artificial polypeptide", "artificial antibody", or "artificial binding agent", consistent with the definition of "artificial" above, refers to a polypeptide, antibody, or binding agent having a distinct amino acid sequence or chemical makeup from those found in natural polypeptides, antibodies, and binding agents. An artificial polypeptide or antibody is not a subsequence of a naturally occurring protein, either the wild-type (i.e., most abundant) or mutant versions thereof. An "artificial polypeptide", "artificial antibody", or "artificial binding agent", as used herein, may be produced or synthesized by any suitable method (e.g., recombinant expression, chemical synthesis, enzymatic synthesis, purification from whole animal, etc.).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);

4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (histidine (H), lysine (K), and arginine (R)); polar negative (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics (e.g., chemically modified peptides, peptoids (side chains are appended to the nitrogen atom of the peptide backbone, rather than to the α-carbons), β-peptides (amino group bonded to the β carbon rather than the α carbon), etc.) and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families (see above). The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence "having at least 70% sequence identity with SEQ ID NO:8" may have up to 37 substitutions relative to SEQ ID NO:8, and may therefore also be expressed as "having 37 or fewer substitutions relative to SEQ ID NO:8." Further, a sequence "having at least 90% sequence similarity with SEQ ID NO:7" may have up to 11 non-conservative substitutions relative to SEQ ID NO:7, and may therefore also be expressed as "having 11 or fewer non-conservative substitutions relative to SEQ ID NO:7."

The term "effective dose" or "effective amount" refers to an amount of an agent, e.g., a neutralizing antibody, that results in the reduction of symptoms in a patient or results in a desired biological outcome. In certain embodiments, an effective dose or effective amount is sufficient to reduce or inhibit the infectivity of one or more strains of influenza.

As used herein, the terms "administration" and "administering" refer to the act of giving a drug, prodrug, or other agent, or therapeutic to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

The term "treatment" encompasses both therapeutic and prophylactic/preventative measures unless otherwise indicated. Those in need of treatment include, but are not limited to, individuals already having a particular condition (e.g., influenza infection) as well as individuals who are at risk of acquiring a particular condition or disorder (e.g., those needing prophylactic/preventative measures, those at risk of influenza exposure, those at risk of having particularly bad outcomes from influenza infection, etc.). The term "treating" refers to administering an agent to a subject for therapeutic and/or prophylactic/preventative purposes.

A "therapeutic agent" refers to an agent that may be administered in vivo to bring about a therapeutic and/or prophylactic/preventative effect.

A "therapeutic antibody" refers to an antibody that may be administered in vivo to bring about a therapeutic and/or prophylactic/preventative effect.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone.

Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term pharmaceutical composition" refers to the combination of an active agent (e.g., binding agent) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintegrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

DETAILED DESCRIPTION

Provided herein are compositions useful for neutralization of influenza virus, and methods of use and manufacture thereof. In particular, compositions comprising antibodies that are cross-reactive with multiple influenza strains (e.g., H7/H1, H7/H3, etc.) are provided, as well as methods of treatment and prevention of influenza infection therewith. Some embodiments described herein relate to antibodies, and antigen binding fragments thereof, that specifically bind to epitopes in an H7 strain of influenza. Embodiments also relate to nucleic acids that encode, immortalized B cells and cultured single plasma cells that produce, and to epitopes that bind, to such antibodies and antibody fragments. In addition, described herein is the use of the antibodies, antibody fragments, and epitopes in screening methods as well as in the diagnosis, treatment and prevention of influenza virus infection. In some embodiments, antibodies and antibody fragments provided herein bind in the stalk region of influenza hemagglutinin (e.g., of an influenza H7 strain and one or more of H1 and H3 strains) and neutralize the influenza virus.

With H7 strains currently posing a threat to human health, experiments were conducted during development of embodiments described herein to determine whether there is cross-protection generated from group 2 influenza virus vaccinations. Human antibodies were generated from plasmablasts of volunteers vaccinated with the seasonal influenza virus vaccine (Wrammert et al. J Exp Med. 2011; 208(1):181-93; Wrammert et al. Nature. 2008; 453(7195): 667-71; herein incorporated by reference in their entireties). Because plasmablasts are activated during an ongoing immune response, this allows for the determination if prior vaccination, especially with H3N2 strains, induced cross-reactive antibodies that neutralize H7 strains. Given the lack of a vaccine against novel H7 viruses, the isolation and characterization of monoclonal antibodies with neutralizing activity can direct vaccine design and also provide a therapeutic resource.

Experiments conducted during development of embodiments described herein demonstrate that at the monoclonal antibody level, a small subset of H3 hemagglutinin-reactive antibodies that were tested neutralized H7N9 viruses and protected mice against homologous challenge. The antibodies bind to the HA stalk domain, but differ in breadth of reactivity to influenza subtypes. Viral escape mutation mapping indicate that these antibodies bind at least two different epitopes on the stalk region. These broadly neutralizing antibodies contribute to the development of therapies against H7N9 strains and are effective against pathogenic H7 strains.

Experiments were conducted during development of embodiments described herein to utilize an antibody microarray and subsequent functional assays to identify and characterize antibodies that neutralize the emerging H7N9 influenza virus strain and protect subjects from infection. In some embodiments, provided herein are H7/H1 (e.g., H7N9/ H1N1) and/or H7/H3 (e.g., H7N9/H3N2) cross-reactive antibodies (e.g., induced by vaccination with influenza A H1N1 and/or H3N2). It has been shown that broadly reactive antibodies binding to the HA stalk region are relatively rare (Corti et al. J Clin Invest. 2010; 120(5):1663-73; herein incorporated by reference in its entirety), but they were preferentially induced by exposure to the highly unique 2009 pandemic H1N1 strain (Wrammert et al. J Exp Med. 2011; 208(1):181-93; Li et al. Proc Natl Acad Sci USA. 2012; 109(23):9047-52; Thomson et al. Frontiers in immunology. 2012; 3(87); herein incorporated by reference in their entireties). It is contemplated that exposure to this pandemic strain, which has a globular head domain that is highly divergent from pre-pandemic seasonal H1N1 strains, was activating cross-reactive memory B cells reactive with conserved epitopes (e.g. in the stalk region) that the virus shared with previous seasonal strains (Kaur et al. Trends in immunology. 2011; 32(11):524-31. Wilson & Andrews. Nature reviews Immunology. 2012; 12(10):709-19; herein incorporated by reference in their entireties). Indeed, one of the H7N9 neutralizing antibodies (045-051310-2B06) identified in experiments conducted during development of embodiments described herein was induced by vaccination with this pandemic influenza strain. Two other neutralizing antibodies, and three H7 cross-reactive antibodies that bound without neutralizing activity, were primed by H3N2 seasonal strains. While it has been shown that H3N2 infection/vaccination can induce HA stalk reactive antibodies, the design of past studies could not predict the frequency at which the H3 stalk epitopes are targeted (Ekiert et al. Nature. 2012; 489(7417):526-32; Margine et al. J Virol. 2013; 87(8):4728-37; herein incorporated by reference in their entireties). Experiments were conducted during development of embodiments described herein that demonstrate the presence of group 2 cross-reactive antibodies following vaccination with seasonal H3N2 strains. Results indicate that prior immunity against the H7N9 strain and other novel strains are boosted with a vaccine eliciting cross-reactive memory B cells. Indeed, as recently demonstrated in mice, immunization with a chimeric HA protein expressing the H3 stalk domain induces broad protection against divergent H3N2 and H7 viruses infection (Margine et al. J Virol. 2013; 87(19):10435-46; Krammer et al. J Virol. 2014; 88(4):2340- 3; herein incorporated by reference in their entireties).

Booster immunizations with divergent influenza strains in the general human population can lead to universal protection against most influenza strains. A better understanding of epitopes targeted by broadly neutralizing antibodies benefits the design and development of new influenza vaccines. The escape viral mutations identified in experiments conducted during development of embodiments described herein (e.g., at residue 384 (I384N for 045-051310-2B06 and I384T for S6-B01)) are located in the epitope targeted by the CR9114 antibody (VH1-69 gene segment), and the binding patterns of the antibodies (CR9114 and 045-051310-2B06; CR9114 and S6-B01) to the HA variants from escape mutants are identical. These antibodies target the same or considerably overlapping epitopes on the stalk region. The differences in the sensitivity to epitope mutations between the two neutralizing antibodies are explained by the fact that different antibodies have unique modes of binding. The approach angle of an antibody to an HA stalk region explains diversity in antibody potency (Friesen et al. Proc Natl Acad Sci USA. 2014; 111(1):445-50; herein incorporated by reference in its entirety). The antibody 042-100809-2F04 is encoded by $V_H3$-23 (Table 1). This antibody only binds and neutralizes group 2 strains and does not bind to the 045-051310-2B06 and S6-B01 escape mutants. Furthermore, the R364K mutation is located in the epitope targeted by the CR8020 antibody (Ekiert et al. Science. 2011; 333(6044):843-50; herein incorporated by reference in its entirety). 042-100809-2F04 also has a similar binding pattern to HA variants as CR8020, indicating that both antibodies have overlapping binding sites on the HA stalk region, but target a different epitope than the group 1 and 2 broadly neutralizing antibodies.

TABLE 1

Repertoire of the protective antibodies.

|  | Heavy chain (V/J) | Light chain (V/J) |
| --- | --- | --- |
| 045051310-2B06 | VH1-18/JH6 | VK3-11/JK5 |
| 042100809-2F04 | VH3-23/JH5 | VK4-1/JK4 |
| S6-B01 | VH1-18/JH6 | VK3-20/JK2 |

The binding of the antibody S6-B01 to the escape mutant HA was not altered by the mutations occurring in the stalk region, despite viral escape and growth. This is the first demonstration of viral escape without the ablation of antibody binding. This mechanism provides a distinct selective advantage to the resulting virus, as B cell memory to this epitope are now non-protective, allowing immune evasion in an original antigenic sin fashion.

All three neutralizing viruses developed not only mutations in the stalk region, but also amino acid substitutions in the globular head domain of HA. Due to the distance between the mutations in the stalk domain and these in the globular head domain, and the fact that the mutations in the stalk domain were sufficient to strongly interfere with binding to the HA, the mutations in the globular head domain are not directly impacting the binding of 042-100809-2F04, 045-051310-2B06 and S6-B01. Elucidating the binding requirements of 042-100809-2F04 in the context of an in vitro infection, clearly demonstrates that 042-100809-2F04 is binding to the stalk domain regardless of the head mutations. Instead, the globular head mutations compensate for the loss of structural integrity caused by escape mutations in the stalk. Escape from neutralization with stalk-reactive antibodies comes with a fitness loss for the virus, which was observed in mice for all three escape mutant viruses. In addition, these head mutations cause other effects, such as enhanced avidity to cellular receptors or increased in structural stability, which facilitates escape from neutralizing antibodies (O'Donnell et al. MBio. 2012; 3(3); herein incorporated by reference in its entirety).

In an exemplary embodiment, an antibody, or an antibody fragment thereof, is provided that is specific for influenza A virus subtype H7 and H3 (e.g. H7N9 and H3N2); H7 and H1 (e.g. H7N9 and H1N1); or H7, H1, and H3 (e.g. H7N9, H1N1, and H3N2). In some embodiments, antibodies and antibody fragments are specific for any of H1, H3, H5, H7 and H9 (e.g. H1N1, H3N2, H5N1, H7N1, H7N7, H9N2, etc.). Other exemplary combinations of subtypes of influenza A virus are also provided.

In some embodiments, an antibody or antibody fragment comprises a heavy chain variable region having an amino acid sequence that is about 70%, 75%, 80%, 85%, 90%, 95%, 97%, 98%, 99% or 100% identical (or any ranges therein) to the sequence recited in any one of SEQ ID NOs: 7, 8, 9, or 35. In some embodiments, an antibody or antibody fragment comprises a heavy chain variable region having >50%, >60%, >70%, >75%, >80%, >85%, >90%, >95%, >97%, >98%, >99% or 100% sequence similarity (or any ranges therein) to one of SEQ ID NOs: 7, 8, 9, or 35. In another embodiment, an antibody or antibody fragment of the invention comprises a light chain variable region having an amino acid sequence that is about 70%, 75%, 80%, 85%, 90%, 95%, 97%, 98%, 99% or 100% identical (or any ranges therein) to the sequence recited in SEQ ID NOs: 10, 11, 12, or 36. In some embodiments, an antibody or antibody fragment comprises a light chain variable region having >50%, >60%, >70%, >75%, >80%, >85%, >90%, >95%, >97%, >98%, >99% or 100% sequence similarity (or any ranges therein) to one of SEQ ID NOs: 10, 11, 12, or 36.

In some embodiments, an antibody or antibody fragment comprises a heavy chain variable region having an amino acid sequence that has about 50%, 60%, 70%, 75%, 80%, 85%, 90%, 95%, 97%, 98%, 99% or 100% sequence similarity (or any ranges therein) to a sequence recited in any one of SEQ ID NOs: 7, 8, 9, or 35. In some embodiments, an antibody or antibody fragment comprises a heavy chain variable region having >50%, >60%, >70%, >75%, >80%, >85%, >90%, >95%, >97%, >98%, >99% or 100% sequence similarity (or any ranges therein) to one of SEQ ID NOs: 7, 8, 9, or 35. In another embodiment, an antibody or antibody fragment of the invention comprises a light chain variable region having an amino acid sequence that is about 50%, 60%, 70%, 75%, 80%, 85%, 90%, 95%, 97%, 98%, 99% or 100% sequence similarity (or any ranges therein) to a sequence recited in SEQ ID NOs: 10, 11, 12, or 36. In some embodiments, an antibody or antibody fragment comprises a light chain variable region having >50%, >60%, >70%, >75%, >80%, >85%, >90%, >95%, >97%, >98%, >99% or 100% sequence similarity (or any ranges therein) to one of SEQ ID NOs: 10, 11, 12, or 36.

In some embodiments, an antibody or antibody fragment exhibits all or a portion of the epitope binding affinity of one of 045-051310-2B06, S6-B01, 042-100809-2F04, or 41 5E04. In some embodiments, an antibody or antibody fragment binds the same epitope as one of 045-051310-2B06, S6-B01, 042-100809-2F04, 41 5E04. In some embodiments, an antibody or antibody fragment exhibits the influenza neutralizing activity of one of 045-051310-2B06, S6-B01, 042-100809-2F04, 41 5E04. In some embodiments, an antibody or antibody fragment neutralizes the same influenza strains as one of 045-051310-2B06, S6-B01, 042-100809-2F04, 41 5E04. In some embodiments, an antibody is not a natural antibody. In some embodiments, an antibody is not a natural human antibody.

The CDRs of the antibody heavy chains are referred to as CDRH1 (or HCDR1), CDRH2 (or HCDR2) and CDRH3 (or HCDR3), respectively. Similarly, the CDRs of the antibody light chains are referred to as CDRK1 (or KCDR1), CDRK2 (or KCDR1) and CDRK3 (or KCDR1), respectively. In some embodiments, antibodies or antibody fragments are provided with heavy chain CDRs corresponding to one of SEQ ID NOs: 13-15, 16-18, 19-21, or 37-39. In some embodiments, antibodies or antibody fragments are provided with heavy chain CDR1 corresponding to one of SEQ ID NOs: 13, 16, 19, or 37. In some embodiments, antibodies or antibody fragments are provided with heavy chain CDR2 corresponding to one of SEQ ID NOs: 14, 17, 20, 38. In some embodiments, antibodies or antibody fragments are provided with heavy chain CDR3 corresponding to one of SEQ ID NOs: 15, 18, 21, 39. In some embodiments, antibodies or antibody fragments are provided with light chain CDRs corresponding to one or SEQ ID NOs: 22-24, 25-27, 28-30, or 40-42. In some embodiments, antibodies or antibody fragments are provided with light chain CDR1 corresponding to one of SEQ ID NOs: 22, 25, 28, or 40. In some embodiments, antibodies or antibody fragments are provided with light chain CDR2 corresponding to one of SEQ ID NOs: 23, 26, 29, or 41. In some embodiments, antibodies or antibody fragments are provided with light chain CDR3 corresponding to one of SEQ ID NOs: 24, 27, 30, or 42. In some embodiments, CDRs are provided having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with one of SEQ ID NOs: 13-30 and 37-42. In some embodiments, CDRs are provided having at least 50% sequence similarity (e.g., 50%, 60%, 70%, 75%, 80%, 85%, 90%, 95%, 98%, 99%, 100%, and any ranges with such endpoints (e.g., 50-100%, 80-100%, 85-99%, 90-99%, etc.)) with one of SEQ ID NOs: 13-30 and 37-42. In some embodiments, CDRs (or a combination thereof) are provided that recognize the same HA epitopes as 045-051310-2B06, S6-B01, 042-100809-2F04, or 41 5E04.

In certain embodiments, an antibody or antigen binding fragment comprises all of the CDRs of antibody 045-051310-2B06 (SEQ ID NOs: 16-18 and 25-27), and neutralizes influenza A virus infection (e.g., in H1N1, H3N2, H7N9, and H15N9 strains). In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 045-051310-2B06 (SEQ ID NOs: 16-18 and 25-27), binds the epitope(s) of antibody 045-051310-2B06, and/or neutralizes influenza A virus infection (e.g., in H1N1, H3N2, H7N9, and H15N9 strains).

In certain embodiments, an antibody or antigen binding fragment comprises all of the CDRs of antibody S6-B01 (SEQ ID NOs: 19-21 and 28-30), and neutralizes influenza A virus infection (e.g., in H5N1, H3N2, H7N9, and H15N9 strains). In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody S6-B01 (SEQ ID NOs: 19-21 and 28-30), binds the epitope(s) of antibody S6-B01, and/or neutralizes influenza A virus infection (e.g., in H5N1, H3N2, H7N9, and H15N9 strains).

In certain embodiments, an antibody or antigen binding fragment comprises all of the CDRs of antibody 042-100809-2F04 (SEQ ID NOs: 13-15 and 22-24), and neutralizes influenza A virus infection (e.g., in H3N2, H7N9, and H15N9 strains). In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 042-100809-2F04 (SEQ ID NOs: 13-15 and 22-24), binds the epitope(s) of antibody 042-100809-2F04, and/or neutralizes influenza A virus infection (e.g., in H3N2, H7N9, and H15N9 strains).

In certain embodiments, an antibody or antigen binding fragment comprises all of the CDRs of antibody 41 5E04 (SEQ ID NOs: 37-39 and 40-42), and neutralizes influenza A virus infection (e.g., in H5N1, H3N2, H7N9, and H15N9 strains). In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 41 5E04 (SEQ ID NOs: 37-39 and 40-42), binds the epitope(s) of antibody 41 5E04, and/or neutralizes influenza A virus infection (e.g., in H5N1, H3N2, H7N9, and H15N9 strains).

The invention further comprises an antibody, or fragment thereof, that binds to the same epitope as an antibody described herein (e.g., 045-051310-2B06, S6-B01, 042-100809-2F04, or 41 5E04), or an antibody that competes with an antibody or antigen binding fragment described herein.

Antibodies within the scope described herein may also include hybrid antibody molecules that comprise one or more CDRs from an antibody described herein (e.g., 045-051310-2B06, S6-B01, 042-100809-2F04, or 41 5E04) and one or more CDRs from another antibody to the same epitope. In one embodiment, such hybrid antibodies comprise three CDRs from an antibody described herein and three CDRs from another antibody to the same epitope. Exemplary hybrid antibodies comprise: (i) the three light chain CDRs from an antibody described herein and the three heavy chain CDRs from another antibody to the same epitope, or (ii) the three heavy chain CDRs from an antibody described herein and the three light chain CDRs from another antibody to the same epitope.

Variant antibodies are also included within the scope herein. Thus, variants of the sequences recited in the application are also included within the scope herein. Such variants include natural variants generated by somatic mutation in vivo during the immune response or in vitro upon culture of immortalized B cell clones. Alternatively, variants may arise due to the degeneracy of the genetic code, or may be produced due to errors in transcription or translation.

Further variants of the antibody sequences having improved affinity and/or potency may be obtained using methods known in the art and are included within the scope herein. For example, amino acid substitutions may be used to obtain antibodies with further improved affinity. Alternatively, codon optimization of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences here are also within the scope included herein.

In some embodiments, variant antibody sequences may share 70% or more (e.g., 75%, 80%, 85%, 90%, 95%, 97%, 98%, 99% or more, or ranges therein) amino acid sequence identity with the sequences recited herein (e.g., SEQ ID NOs: 7-30 and 35-42). In some embodiments, variant antibody sequences may share 50% or more (e.g., 55%, 60%, 65%, 75%, 80%, 85%, 90%, 95%, 97%, 98%, 99% or more, or ranges therein) amino acid sequence similarity with the sequences recited herein (e.g., SEQ ID NOs: 7-30 and 35-42).

In one embodiment, nucleic acid sequences described herein include nucleic acid sequences having at least 70%, at least 75%, at least 80%, at least 85%, at least 90%, at least 95%, at least 98%, or at least 99% identity to the nucleic acid encoding a heavy or light chain of an antibody described herein (e.g., SEQ ID NOs: 7-12 and 35-36). In another embodiment, a nucleic acid sequence has the sequence of a nucleic acid encoding a heavy or light chain CDR of an antibody of the invention (e.g., SEQ ID NOs: 13-30, and 37-42).

In some embodiments, provided herein are modified antibodies and/or modified antibody fragments (e.g., antibodies and antibody fragments comprising non-natural amino acids, substituents, bonds, moieties, connections, etc.). For example, modifications may comprise the introduction of disulfide bonds, glycosylation, lipidation, acetylation, phosphorylation, or any other manipulation or modification, such as conjugation with a labeling or therapeutic agent. Modifications may also include the substitution of natural amino acids for amino acid analogs (including, for example, unnatural amino acids, etc.), as well as other modifications known in the art.

In some embodiments, an antibody finding use in embodiments herein is a non-natural immunogenic agent, such as: an antibody fragment, a non-natural antibody comprising the CDRs herein, a modified antibody, a monoclonal antibody, a humanized antibody, a chimeric antibody, and non-natural combinations thereof.

Further included within the scope of the invention are vectors, for example, expression vectors, comprising a nucleic acid sequence described herein. Cells transformed with such vectors are also included. Examples of such cells include but are not limited to, eukaryotic cells, e.g. yeast cells, animal cells or plant cells. In one embodiment the cells are mammalian, e.g. human, CHO, HEK293T, PER.C6, NS0, myeloma or hybridoma cells.

Embodiments within the scope of this disclosure include methods of preventing or treating influenza infections comprising administering a therapeutically-effective or prophylactically effective amount of a monoclonal antibody having specificity for an epitope in an H7 influenza and one or more additional strains of influenza (e.g., H1, H2, H3, H5, and/or H9 strains). In some embodiments, an antibody recognizes (e.g., has affinity and/or specificity for) epitopes having at least 90%, at least 92%, at least 95%, at least 97%, at least 98%, or at least 99% homology to epitope(s) recognized by (e.g., has affinity and/or specificity for) the cross-reactive (e.g., H1/H7, H3/H7, etc.) antibodies described herein.

In some embodiments, a pharmaceutical composition comprising the antibodies disclosed herein includes an acceptable carrier and is formulated into a suitable dosage form according to administration modes. Pharmaceutical preparations suitable for administration modes are known, and generally include surfactants that facilitate transport across the membrane. Such surfactants may be derived from steroids, or may be cationic lipids such as N-[1-(2,3-dioleyloxy)propyl]-N,N,N-trimethylammonium chloride (DOTMA), or various compounds such as cholesterol hemisuccinate and phosphatidyl glycerol.

For oral administration, the pharmaceutical composition may be presented as discrete units, for example, capsules or tablets; powders or granules; solutions, syrups or suspensions (edible foam or whip formulations in aqueous or non-aqueous liquids); or emulsions.

For parenteral administration, the pharmaceutical composition may include aqueous and non-aqueous sterile injection solutions which may contain anti-oxidants, buffers, bacteriostats and solutes which render the formulation substantially isotonic with the blood of the intended recipient; and aqueous and non-aqueous sterile suspensions which may include suspending agents and thickening agents. Excipients available for use in injectable solutions include, for example, water, alcohol, polyols, glycerin, and vegetable oils. Such a composition may be presented in unit-dose (single dose) or multiple dose (several doses) containers, for example, sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The pharmaceutical composition may include antiseptics, solubilizers, stabilizers, wetting agents, emulsifiers, sweeteners, colorants, odorants, salts, buffering agents, coating agents, or anti-oxidants.

Compositions may comprise, in addition to the antibody or antibodies described herein, a therapeutically active agent (e.g., drug), additional antibodies (e.g., against influenza or another target), etc.

The present composition may be formulated into dosage forms for use in humans or veterinary use. The composition comprising the antibodie(s) may be administered to influenza-infected or highly susceptible humans and livestock, such as cows, horses, sheep, swine, goats, camels, and antelopes, in order to prevent or treat the incidence of influenza. When a subject is already infected, the present antibodie(s) may be administered alone or in combination with another antiviral treatment.

The antibody composition may be administered in a pharmaceutically effective amount in a single- or multiple-dose. The pharmaceutical composition may be administered via any of the common routes, as long as it is able to reach the desired tissue. Thus, the present composition may be administered via oral or parenteral (e.g., subcutaneous, intramuscular, intravenous, or intradermal administration) routes, and may be formulated into various dosage forms. In one embodiment, the formulation is an injectable preparation. Intravenous, subcutaneous, intradermal, intramuscular and dropping injectable preparations are possible.

Antibodies may be coupled to a drug for delivery to a treatment site or coupled to a detectable label to facilitate imaging of a site comprising cells of interest, such as cells infected with influenza A virus. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody of the invention and an epitope of interest (an influenza A virus epitope) can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}$I, $^{131}$I, $^{35}$S, or $^3$H. Such labeled reagents may be used in a variety of well-known assays, such as radioimmunoassays, enzyme immunoassays, e.g., ELISA, fluorescent immunoassays, and the like.

An antibody may be conjugated to a therapeutic moiety. Such antibody conjugates can be used for modifying a given biological response; the drug moiety is not to be construed as limited to classical chemical therapeutic agents. For example, the drug moiety may be a protein or polypeptide possessing a desired biological activity. Techniques for conjugating such therapeutic moiety to antibodies are well known. See, for example, Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurds, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158; herein incorporated by reference in their entireties.

Alternatively, an antibody, or antibody fragment thereof, can be conjugated to a second antibody, or antibody fragment thereof, to form an antibody heteroconjugate as described in U.S. Pat. No. 4,676,980; herein incorporated by reference in its entirety. In addition, linkers may be used between the labels and the antibodies of the invention (e.g. U.S. Pat. No. 4,831,175; herein incorporated by reference in its entirety).

Antibodies of the invention may also be attached to a solid support. Additionally, antibodies of the invention, or functional antibody fragments thereof, can be chemically modified by covalent conjugation to a polymer to, for example, increase their circulating half-life. In some embodiments the polymers may be selected from polyoxyethylated polyols and polyethylene glycol (PEG). PEG is soluble in water at room temperature and has the general formula: R(O—CH$_2$—CH$_2$)$_n$O—R where R can be hydrogen, or a protective group such as an alkyl or alkanol group.

Water-soluble polyoxyethylated polyols may also be employed. They include polyoxyethylated sorbitol, polyoxyethylated glucose, polyoxyethylated glycerol (POG), and the like. Another drug delivery system that can be used for increasing circulatory half-life is the liposome.

Antibodies may be provided in purified form. Typically, the antibody will be present in a composition that is substantially free of other polypeptides e.g. where less than 90% (by weight), usually less than 60% and more usually less than 50% of the composition is made up of other polypeptides.

Antibodies of the invention can be of any isotype (e.g. IgA, IgG, IgM (e.g., an alpha, gamma or mu heavy chain). Within the IgG isotype, antibodies may be IgG1, IgG2, IgG3 or IgG4 subclass. Antibodies may have a kappa or a lamda light chain.

EXPERIMENTAL

Example 1

Materials and Methods

Cells, Viruses and Recombinant Hemagglutinin Proteins 293T and MDCK cells were obtained from the American Type Culture Collection (ATCC). H7N9 virus expressing the HA and NA of A/Shanghai/1/13 and the internal genes from A/Puerto Rico/8/34 was rescued as previously described (40). All influenza virus stocks used for the assays were freshly grown in SPF eggs, purified and titered. Recombinant HA proteins derived from influenza A virus strains A/Uruguay/716/2007 (H3N2), A/Wisconsin/57/05 (H3N2), A/Perth/16/2009 (H3N2), A/Victoria/361/2011 (H3N2), A/Canada/rv444/2004 (H7N3) and A/Netherlands/219/2003 (H7N7) were obtained from BEI resources. Recombinant HA proteins derived from influenza A virus strains A/Panama/2007/99 (H3N2), A/Hong Kong/1/1968 (H3N2), A/chicken/Jalisco/12283/12 (H7N3), A/Anhui/1/13 (H7N9), A/Shanghai/1/13 (H7N9), A/rhea/North Carolina/39483/93 (H7N1), A/shearwater/West Australia/2576/79 (H15N9), A/California/04/09 (H1N1) and A/South Carolina/1/18 (H1N1) were expressed with a C-terminal trimerization domain and a hexahistidine tag in the baculovirus expression system as described before (Margine et al. Journal of visualized experiments: JoVE. 201381):e51112; herein incorporated by reference in its entirety). A chimeric HA made of the stalk region of A/Shanghai/1/13 (H7N9) and the globular head domain of A/duck/Czechoslovakia/1956 (H4N6) was expressed as well using the same system (Krammer et al. Clinical and vaccine immunology: CVI. 2014; herein incorporated by reference in its entirety).

Antibody Microarray

Eighty-three H3N2 reactive antibodies were diluted in Protein Printing Buffer (ARRAYIT) to 250 μg/ml and printed in triplicate on SUPEREPDXY glass slides using the SpotBot® 3 microarrayer (ARRAYIT). Before use, slides were washed with PBS 0.05% TWEEN-20 and then treated with Blocklt® blocking buffer (ARRAYIT) for 1 h at room temperature (RT). Slides were washed three times with protein microarray wash buffer between each step and all the reactions were done at room temperature in protein microarray reaction buffer (ARRAYIT). To detect and normalize antibody signals, the slides were incubated for 1 h with Cy3-conjugated goat anti-human IgG, Fc-fragment specific antibody (Jackson ImmunoResearch). Recombinant HA proteins were biotinylated with EZ-Link Maleimide-PEG2-Biotin (Pierce) and excess free biotin was removed using Zeba Desalting Columns (Pierce). Slides were incubated with 40 μg/ml of each recombinant HA for 1 h and then with Alexa-Fluor 647-conjugated Streptavidin (Invitrogen) for 1 h. Signals were quantified using a GENEPIX 4000B microarray scanner and analyzed with GENEPIX Pro 6.0 software (Molecular Devices). Microarray data have deposited in the MIAME-compliant public database. The accession GEO numbers are GSE63249 and GPL19411.

ELISA Assays

Plates were coated with recombinant HAs at various concentrations depending on the HA (from 0.5 to 5 μg/ml) in PBS overnight at 4° C. After blocking, antibodies were incubated (starting concentration 10 μg/ml) for 1 h at 37° C. Horseradish peroxidase (HRP)-conjugated goat anti-human IgG antibody (Jackson ImmunoResearch) was used to detect binding of the mAbs, followed by development with Super Aquablue ELISA substrate (eBiosciences). Absorbance was measured at 405 nm on a microplate spectrophotometer (BioRad). To standardize the assays, high-affinity antibodies with known binding characteristics were included on each plate and the plates were developed when the absorbance of these controls reached 3.0±0.1 OD units.

Competition ELISAs were performed by inhibition of binding of each biotinylated antibody of interest at the half-maximal binding concentration with a 10-fold molar excess of competitor antibody. HRP-conjugated streptavidin (Southern Biotech) was used for detection. The absorbance value of each antibody against itself is scored at 100% inhibition and comparison of different antibodies was done as a percentage of this 100% inhibition.

Memory B-Cell Assay and ELISPOT

PBMC were plated at $5 \cdot 10^5$ cells/well in media supplemented with pokeweed mitogen extract (PWM), phosphothiolated CpG ODN-2006 (Sigma) and *Staphylococcus aureus* Cowan (SAC) (Sigma), as previously described (42). After 6 days, cells were washed and plated on 96-well filter plates (Millipore) coated with 2 μg/ml of various HAs. Cells were incubated overnight at 37° C., plates were washed and then incubated with an anti-human IgG-biotin antibody (Mabtech) followed by streptavidin alkaline phosphatase (Southern Biotech). Plates were developed using NBT/BCIP (Thermo Scientific).

Hemagglutination Inhibition Assay (HAI)

Viruses were diluted to 8 HA units/50 μl and 25 μl was combined in duplicate wells with an equal volume of antibody serially diluted in PBS. 50 μl of 0.5% Turkey red blood cells (Lampire Biological) was then added and incubated for 1 h at RT. Minimum effective concentrations were read based on the final dilution for which hemagglutination was observed.

Microneutralization Assay

MDCK cells were maintained in minimum essential medium (MEM) supplemented with 10% fetal calf serum (FCS) at 37° C. Three-fold serially diluted antibody (starting concentration 300 μg/ml) in serum free MEM with TPCK-treated trypsin (Sigma) was mixed with an equal volume of virus (~1000 TCID50) and incubated 1 h at 37° C. Confluent MDCK cells in 96-well format were washed twice with PBS, the mixture antibody/virus was added to the cells and incubated for 1 h at 37° C. Then the antibody/virus mixture was removed and cells were cultured for 20 hours at 37° C. with serum-free MEM containing TPCK-treated trypsin and the antibody at the appropriate concentration. Then cells were washed twice with PBS, fixed with 80% ice cold acetone at −20° C. for 1 h, washed 3 times with PBS, blocked for 30 min with 5% milk-PBS and then treated 30 min with 2% $H_2O_2$. An anti-NP antibody (EVS) diluted in 3% BSA-PBS was incubated for 1 h at RT. An HRP anti-mouse antibody (Santa Cruz Biotechnology) was used for detection, the plates were developed using SigmaFast OPD (Sigma) and the absorbance was measured at 490 nm. The final concentration of antibody that reduced infection to 50% ($IC_{50}$) was determined using GraphPad Prism software.

Plaque Assay and $PRNT_{50}$ Assay

Plaque assay was done as previously published (Wrammert et al. J Exp Med. 2011; 208(1):181-93; herein incorporated by reference in its entirety) except that cells were incubated 48 h with the agar overlay. Plaques were counted and the final concentration of antibody that reduced plaques to 50% ($PRNT_{50}$) was determined using GraphPad Prism software.

Evaluation of the Prophylactic and Therapeutic Efficacy in Mice

Groups of 5 female BALB/c mice (Jackson laboratories) aged 6-8 weeks received a dose of 1.5, 5 or 15 mg/kg of purified antibody intraperitoneally. Control mice received purified human polyclonal IgG (Sigma) or a non-H7 binding H3N2 neutralizing monoclonal antibody (011-10069 2C01) at a 15 mg/kg dose. Two hours post treatment, mice were deeply anesthetized using a ketamine/xylazine mixture and infected with 7.5 $LD_{50}$ (3975 $TCID_{50}$) of A/Shanghai/1/2013 (H7N9) viruses diluted in PBS (pH 7.4). In a therapeutic setting, mice received a 15 mg/kg dose of each antibody individually 24 hours or 72 hours post-infection (h.p.i.). The mice were monitored daily for survival and weight loss until day 14 post-infection. Animals that lost more than 25% of their initial body weight were euthanized.

Evaluation of the Pathogenicity of the Escape Mutant Viruses in Mice and Determination of the $LD_{50}$ Mice were challenged with escalating doses, ranging from 100-100,000 plaque forming units (PFU), of the A/Shanghai/1/2013 H7N9 wild-type virus, the 045-051310-2B06 escape mutant virus, the 042-100809-2F04 escape mutant virus, or the S6-B01 escape mutant virus. The mice were monitored daily for survival and weight loss until day 14 post-infection. Animals that lost more than 25% of their initial body weight were euthanized. The $LD_{50}$ were determined using GraphPad Prism software.

Generation of Escape Mutants

A/Shanghai/1/2013 virus was diluted in serum free MEM media and was incubated with MDCK cells in 24 well plates for 45 minutes. After the incubation, TPCK-treated trypsin containing MEM media supplemented with antibody (045-051310-2B06, 042-100809-2F04 or S6-B01) at a concentration equivalent to one $IC_{50}$ was added to the wells. Positive control wells (virus only) and negative control wells (no virus) were overlayed with TPCK-treated trypsin containing MEM media only. Twenty-four hours post-infection, supernatants were harvested and used to infect fresh cells that were again overlayed with TPCK-treated trypsin containing MEM media, with or without one $IC_{50}$ of the respective antibody. After six passages, the antibody concentration was increased to two $IC_{50}$. Three $IC_{50}$ concentrations were used for passage 7 and 8. Viruses from passage 8 were plaque purified and 4 clones of each virus were picked and grown in ten-day old embryonated chicken eggs for 48 hours. The presence of virus was confirmed using an HA assay. RNA was extracted from allantoic fluid using TriZol reagent (Invitrogen), cDNA was generated using Superscript III reverse transcriptase (Invitrogen) and HA segments were subjected to Sanger sequencing.

Generation of A/Shanghai/1/2013 with 042-100809-2F04 Escape Mutant Point Mutations A/Shanghai/1/2013 WT was amplified with the following primers: TCGACCTCCGAAGTTGGGGGGGAGCAAA AGCAGGGGAAAATAAAAACAACCAAAATGAAC AC TCAAATCCTGGTATTCGCTCTGATTG (H7HA forward;

SEQ ID NO: 31) or TTTTGGGCCGCCGGGTTATTAGTA-GAAACAAGGGTGTTTTTCCTCATA TTTCTGAAAT-TCTAATCTTATATACAAATAGTGCACCGCATGTTTC-CATTCT (H7 HA reverse; SEQ ID NO: 32). Point mutations, corresponding to 042-100809-2F04 escape mutant amino acid substitutions, were introduced to the A/Shanghai/1/2013 (H7N9) virus HA segment through site-directed mutagenesis via mutagenizing primers with regions of overlap. Alongside PCR fragments coding for 042-100809-2F04 point mutations, A/Shanghai/1/2013 WT PCR fragments were generated with similar primers lacking the nucleotide substitutions. PCR amplification with H7 HA forward and H7 HA reverse, along with combinations of these PCR fragments, allowed for generation of the four full length HA segments, leading to the generation and isolation of the following gene segments: A/Shanghai/1/2013 HA R364K, A/Shanghai/1/2013 HA G63E/G234D, A/Shanghai/1/2013 HA G63E, and A/Shanghai/1/2013 HA G234D. The HA gene segments were then subcloned into the ambisense expression vector pDZ (Quinlivan et al. J Virol. 2005; 79(13):8431-9; herein incorporated by reference in its entirety) via In-Fusion HD Plus cloning kit (Clontech). Virus was rescued via a reverse genetics system, as previously described (44, 45) with minor modifications to generate 6:2 reassortants. Individually, each pDZ plasmid coding for the HA segment was transfected with seven other plasmids, coding for A/Shanghai/1/2013 NA and the remaining six segments from A/Puerto Rico/8/1934, into 293T cells. Twenty-four hours post-transfection, supernatant/cell mixture was propagated in embryonated chicken eggs, as previously described. Rescued virus pools were dilution purified and sequence confirmed.

Immunofluorescence Assay

MDCK cells were infected with A/Shanghai/1/2013 wild type virus, the escape mutants (045-051310-2B06, 042-100809-2F04 or S6-B01 mutants), or with the single point mutation viruses (A/Shanghai/1/2013 HA R364K, A/Shanghai/1/2013 HA G63E/G234D, A/Shanghai/1/2013 HA G63E, or A/Shanghai/1/2013 HA G234D) a an MOT of 3 in the absence of trypsin overnight. The cell monolayer was fixed with PBS containing 0.5% parafortnaldehyde for 30 minutes and then blocked with PBS containing 5% non-fat milk for another 30 minutes at RT. Monoclonal antibodies (045-051310-2B06, 042-100809-2F04 or S6-B01) were diluted to 5 μg/ml in PBS 1% BSA and incubated for two hours at RT. Cells were then washed three times with PBS. A goat anti-human IgG Alexa Fluor 488 conjugated antibody (Life Technologies, Inc.) was used for detection. Binding was visualized using an Olympus IX70 inverted fluorescence microscope. The mouse mAb E10 (anti-M2 antibody, Center for Therapeutic Antibody Development at Icahn School of Medicine at Mount Sinai) at 5 μg/ml or polyclonal serum, from a serially 147-immunized mouse were used as a positive infection control and a goat anti-mouse IgG Alexa Fluor 488 conjugated antibody (Life Technologies, Inc.) was used for detection.

Expression of HA Mutant Recombinant Proteins and Binding Analysis by ELISA

The HA segments of the escape mutants were cloned into baculovirus transfer vectors as described above. Additionally, hybrids with the head domain of the wild type HA A/Shanghai/1/2013 and the stalk domains (demarcation line cysteins 52 and 277, H3 numbering) of the escape mutants were generated by PCR and cloned into baculovirus transfer vectors as well. HA proteins were then expressed as described above and the binding of each antibody was assessed by ELISA using $Ni^{2+}$-plates (Qiagen). These plates were chosen specifically to ensure optimal structural integrity of the proteins. Briefly, plates were coated with recombinant HAs at 2 μg/ml in PBS overnight at 4° C. After blocking, antibodies were incubated (starting concentration 30 μg/ml) for 1 h at 37° C. An HRP-labeled anti-human (Sigma) or HRP-labeled anti-mouse (Santa Cruz) was used for detection, the plates were developed using SigmaFast OPD (Sigma) and the absorbance was measured at 490 nm.

Example 2

Cross-Reactive Antibodies

Cross-Reactive Antibodies React with Novel Pathogenic H7N9 Strains

Figure 1A:
FIGS. 1A-C. Identification of H3N2 specific antibodies cross-reacting with the HA of H7N9 strains. (A) The binding of 83 H3N2 reactive antibodies to a panel of H3N2 and H7 recombinant HA proteins was assessed using an antibody microarray. Median triplicate fluorescence ratios were used. The minimum and maximum values for each HA were used to normalize data to reflect relative binding of each antibody. The data shown is representative of two independent experiments. (B) Percentage of group 2 cross-reactive IgG memory cells in 13 vaccinated individuals using an ELISPOT assay. The frequency of H3N2 HA specific IgG memory cells binding to H7 HA stalk domain was assessed using H7 stalk/H4 head chimeric HA (H4 head HA and H7 head HA were used as a control). Each symbol represents one individual. Median value is represented. (C) In vitro microneutralization assay using A/Shanghai/1/2013 (H7N9) virus.

To identify H7 binding antibodies, antibody microarray technology was developed that allows high-throughput screening for cross-reactivity to influenza HA proteins (FIG. 1A). 83 antibodies were selected from 28 individuals, that were previously detected as H3N2 reactive by ELISA, and their reactivity to different H3 and H7 recombinant HAs was assayed. Experiments conducted during development of embodiments described herein demonstrate that 6 of the 83 (7%) H3 reactive antibodies bind both the A/Shanghai/1/2013 (H7N9) and A/Anhui/1/2013 (H7N9) strains isolated from the first infected patients in China. These six antibodies were each from different individuals, thus 21% (6/28) of this cohort had evidence of H7 cross-reactive immunity.

Figure 1B:
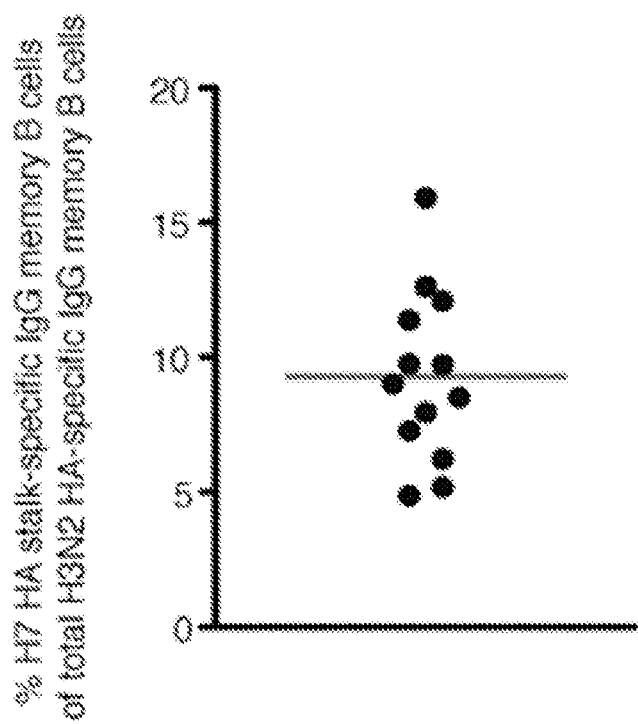

To more comprehensively assess the frequency of cross-reactive immunity within the vaccinated population, the frequency of H3/H7 reactive memory cells 14 days post-seasonal vaccination was analyzed by ELISPOT for 13 individuals. Since cross-reactive antibodies typically bind to conserved epitopes on the stalk domain, the percentage of H7 stalk reactive memory cells was determined using a chimeric HA, comprised of the stalk domain of the A/Shanghai/1/2013 (H7N9) strain and the globular head domain of an H4 strain (A/duck/Czechoslovakia/1956 H4N6), to which humans are naïve (Krammer et al. Clinical and vaccine immunology: CVI. 2014; herein incorporated by reference in its entirety). Two control HAs were used: one comprising the globular head region of the H4 strain and one comprising the globular head region of the A/Shanghai/1/2013 (H7N9) strain. The reactivity of memory cells to H3 was assessed using commercially available H3 HAs. Using this method, 9% (median 9.3%, range 4.9-15.9%) of H3N2 HA-reactive IgG memory cells bound to the H7 stalk. This indicates that out of the H3N2 specific memory cells generated from seasonal vaccinations, 9% are group 2 cross-reactive (FIG. 1B). Collectively, the antibody microarray and ELISPOT results demonstrate that at least 7% of H3N2 reactive B cells react with H7 influenza strains.

Figure 1C:
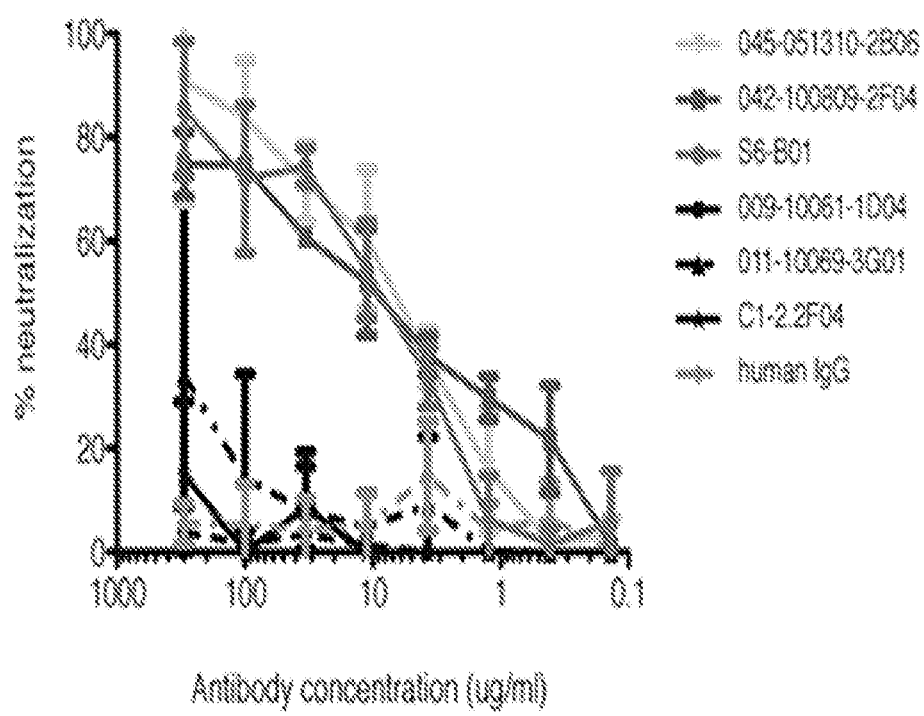
Figure 2:
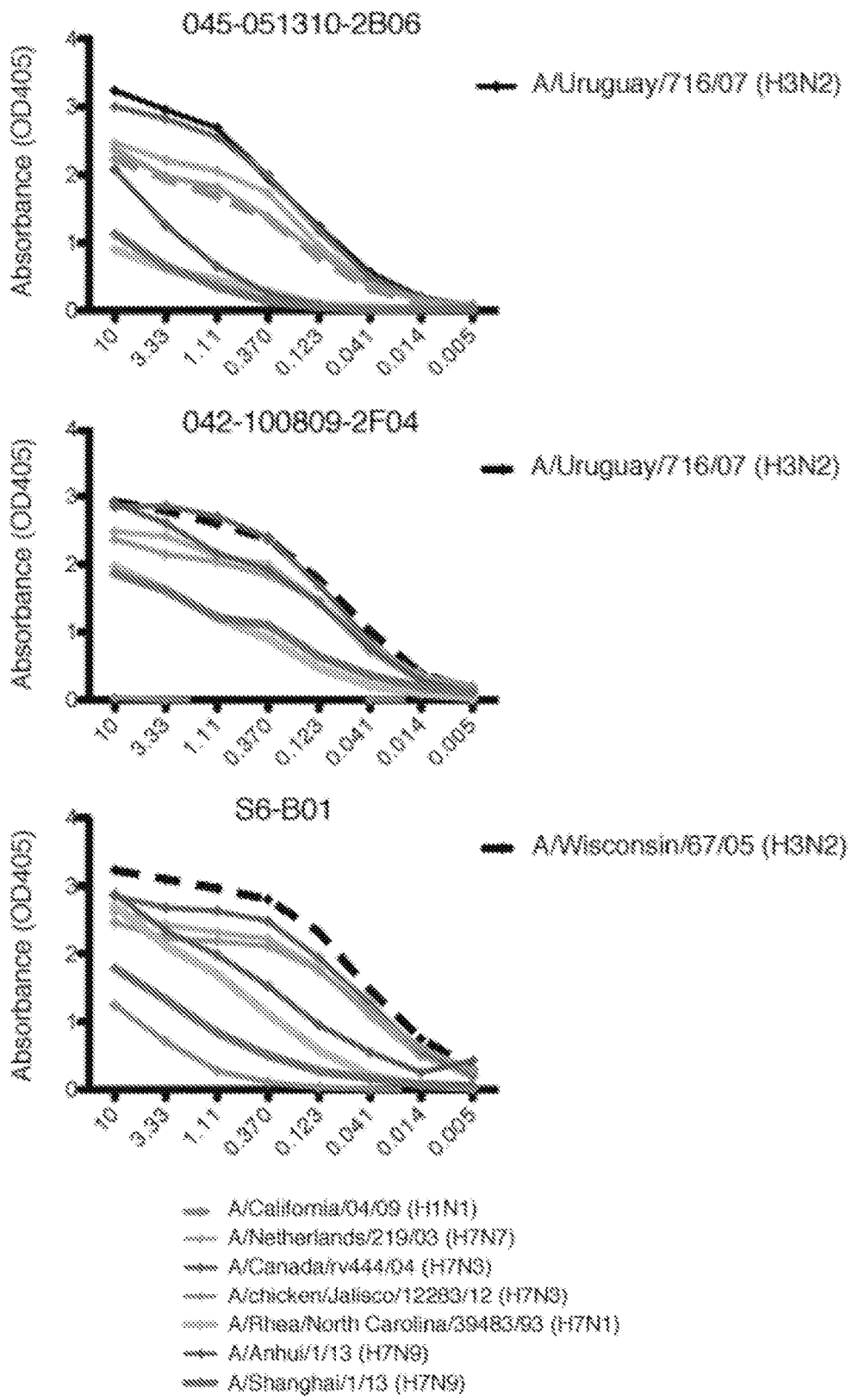
FIG. 2. Binding of the neutralizing antibodies to various H7 strains. ELISA binding curves for multiple recombinant HA proteins are shown. The dotted line corresponds to the strain the antibody was originally induced by. Data are representative of independent experiments.

Three of the Cross-Reactive Antibodies Neutralize Pathogenic H7N9 Strains In Vitro and Protect Mice from Lethal Infection To determine the functional capacity of H7 cross-reactive antibodies, the ability of the antibodies to neutralize the A/Shanghai/1/2013 virus was assessed in a standard microneutralization assay. Three of the 6 cross-reactive antibodies neutralized H7N9 virus in vitro: 045-051310-2B06, 042-100809-2F04 and S6-B01, whereas a human IgG control antibody did not (FIG. 1C). S6-B01 and 042-100809-2F04 were induced by the seasonal vaccine H3N2 strains A/Wisconsin/67/2005 and A/Uruguay/716/2007 respectively (table 2). The antibody 045-051310-2B06 was generated in response to the pandemic A/California/04/2009 (H1N1) strain. 045-051310-2B06 also bound the A/Uruguay/716/2007 (H3N2) strain and all three neutralizing antibodies bound various H7 strains (FIG. 2).

TABLE 2

Information on the strain and year of influenza vaccination

| | vaccine | strain |
|---|---|---|
| 45051310-2B06 | Pandemic H1N1 2009 | A/California/07/2009 |
| 042100809-2F04 | TIV 2009/2010 | A/Uruguay/716/2007 (H3N2) |
| S6-B01 | TIV 2006/2007 | A/Wisconsin/67/2005 (H3N2) |

Figure 3A:
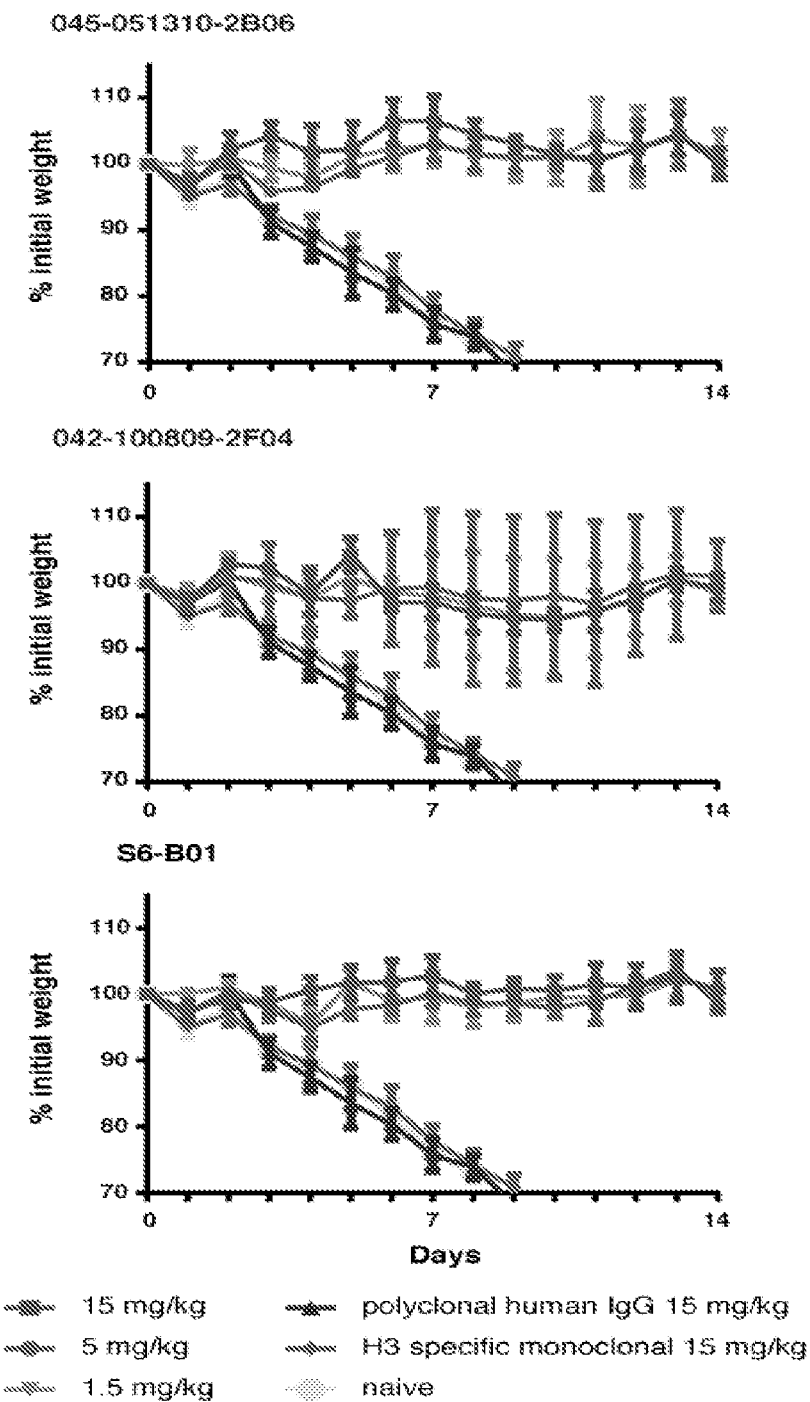
FIGS. 3A-B. Passive transfer of the H7N9 neutralizing antibodies in mice. (A) 6-8 week old female BALB/c mice (5 per experimental condition) were injected intraperitoneally with 1.5, 5 or 15 mg/kg of antibody (045-051310-2B06, 042-100809-2F04 or S6-B01) and then infected with a lethal dose (7.5 LD50) of A/Shanghai/1/2013 virus. Percentage of initial body weight was plotted for each antibody and compared to untreated mice, mice that received 15 mg/kg of a polyclonal human IgG antibody and mice that received 15 mg/kg of 011-10069 2C01 (H3N2 neutralizing antibody). Control groups are the same for all three panels. (B) 6-8 week old female BALB/c mice (5 per experimental condition) were infected with a lethal dose (7.5 LD50) of A/Shanghai/1/2013 virus and then injected intraperitoneally with 15 mg/kg of antibody 24 or 72 hours post-infection. Percentage of initial body weight is plotted for each antibody and compared to untreated mice, mice that received 15 mg/kg of a polyclonal human IgG antibody. Control groups are the same for all three panels.
Figure 3B:
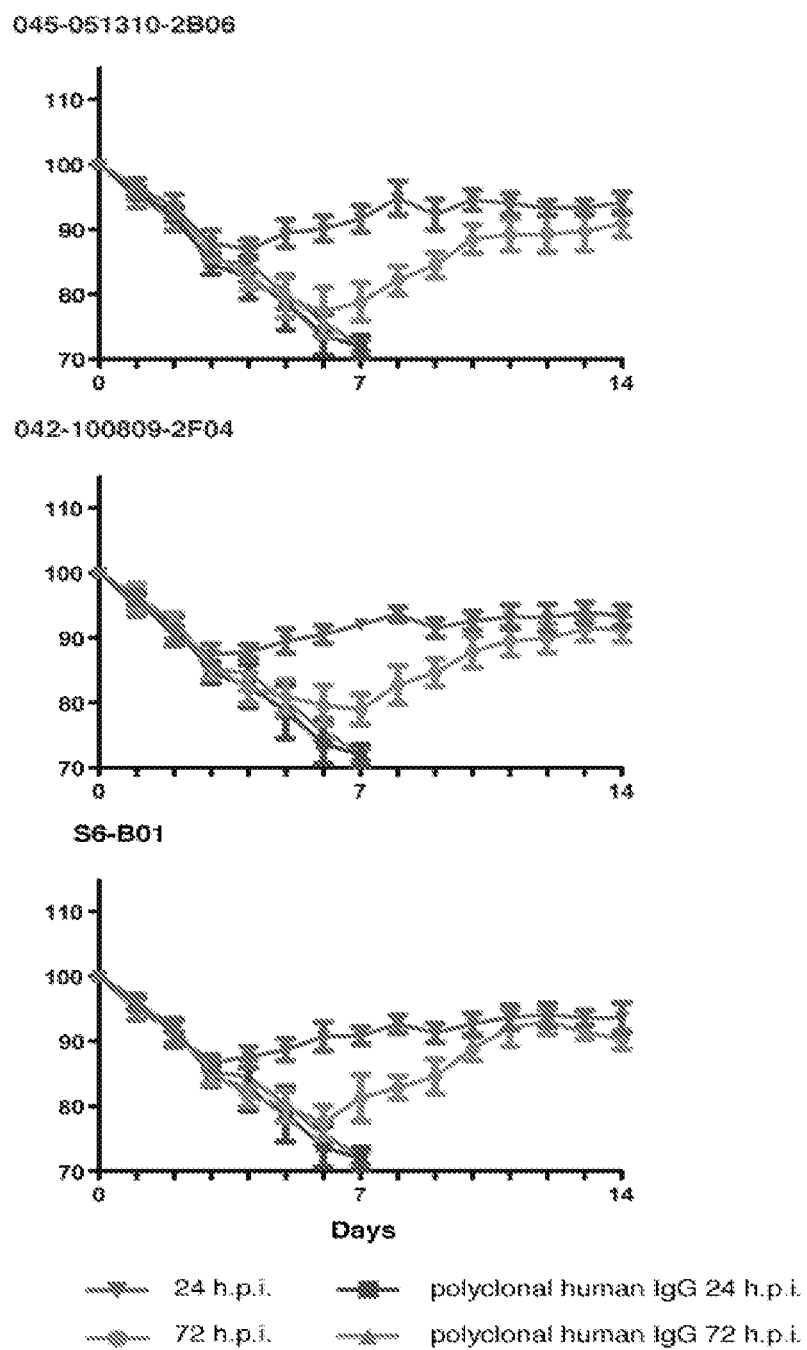

Because in vitro neutralization is not always predictive of in vivo potency (Dreyfus et al. Science. 2012; 337(6100): 1343-8; herein incorporated by reference in its entirety), the protective efficacy of the three H7N9 neutralizing antibodies was tested in a mouse model. Mice were treated prophylactically with 1.5, 5 or 15 mg/kg of each antibody intraperitoneally and then challenged with a lethal dose (7.5 $LD_{50}$) of A/Shanghai/1/2013 virus (H7N9). In this model, the three antibodies showed comparable efficacy as they conferred protection at the lowest dose of 1.5 mg/kg, with all mice in each group surviving infection. Although mice were protected from mortality at a dose of 1.5 mg/kg of 042-100809-2F04, one out of the five mice treated with 5 mg/kg of antibody showed weight loss of about 25%. Untreated control mice and those treated with 15 mg/kg of polyclonal human IgG lost weight and succumbed to infection by day 8-9. Furthermore, mice treated with an H3N2 neutralizing antibody that did not bind H7 (011-10069 2C01) did not survive past day 8-9 (FIGS. 3A and 4A). These antibodies were also tested in a therapeutic model, with 15 mg/kg of each antibody being administered 24 hours post-infection to their respective groups. All three antibodies were able to protect mice from the lethal challenge. A similar experiment was conducted with the antibody being delivered 72 hours post-infection and 100% survival was observed only with 042-100809-2F04. For the antibodies 045-051310-2B06 and S6-B01, reduced survival, 80% and 60% respectively, was observed (FIGS. 3B and 4B). These findings demonstrate that these antibodies that bind H3N2 influenza virus strains infectious to humans can provide in vivo protection of mice against lethal infections with the pathogenic H7N9 influenza virus.

The Cross-Reactive Antibodies Neutralize Various Influenza Strains

The H7 neutralizing antibodies bind to epitopes conserved among a wide variety of influenza strains. Therefore cross-reactivity to multiple influenza A group 1 (H1 and H5) and group 2 (H3, H7 and H15) recombinant HAs was assessed. 045-051310-2B06, 042-100809-2F04, and S6-B01 bound at low concentration to various H3N2 and H7 strains as well as the H15N9 strain, confirming their cross-reactivity within group 2 (FIG. 5). The antibodies bound H7 strains from both the North American and Eurasian lineages (phylogenetic tree, FIG. 6), and provide cross-protection with other avian H7 strains (20). 042-100809-2F04 bound only to group 2 HAs. 045-051310-2B06 bound the A/California/04/2009 H1N1 strain at low concentration but also cross-reacted with various H1N1 strains. Interestingly, S6-B01 also bound to H1N1 strains and both 045-051310-2B06 and S6-B01 cross-reacted with the A/Vietnam/1203/2004 (H5N1) HA (FIG. 5). None of the H7 neutralizing antibodies bound to influenza B HA of either the Yamagata or Victoria lineage (data not shown). Thus these three antibodies displayed unique strain-specificities.

To assess the breadth of neutralization capacity of these antibodies, plaque reduction assays were performed with various influenza virus strains (FIG. 7A). 045-051310-2B06 and 042-100809-2F04 were able to prevent infection of MDCK cells with similar efficacy for all of the H3N2 strains tested ($PRNT_{50}$ ranging from 6 to 19 µg/ml). Furthermore, both antibodies neutralized A/Shanghai/1/2013 (H7N9) but at a higher concentration when compared to H3N2 strains ($PRNT_{50}$=19µ/ml for 045-051310-2B06 and $PRNT_{50}$=27 µg/ml for 042-100809-2F04). 045-051310-2B06 also showed neutralization efficacy against the A/chicken/Jalisco/12283/12 (H7N3) strain from the North American lineage ($PRNT_{50}$=18 µg/ml). S6-B01 potently neutralized all H3N2 and H7 strains at low concentrations ($PRNT_{50}$ ranging from 3 to 6 µg/ml). 045-051310-2B06 neutralized the A/California/04/2009 (H1N1) strain ($PRNT_{50}$=5.5 µg/ml) whereas S6-B01 did not ($PRNT_{50}$>120 µg/ml). This demonstrates that 042-100809-2F04 is a group 2 broadly neutralizing antibody whereas 045-051310-2B06 is a pan-influenza A neutralizing antibody (both group 1 and 2). S6-B01 binds group 1 and 2 strains but in vitro neutralization is only detected among group 2 viruses.

The Neutralizing Cross-Reactive Antibodies Bind to Conserved but Distinct Epitopes on the HA-Stalk Domain The majority of neutralizing antibodies generated after exposure to influenza viruses are strain-specific, binding the highly variable loops on the globular head domain of HA. On the other hand, broadly neutralizing monoclonal antibodies (group 1 and 2) often bind conserved epitopes on the HA stalk domain. Antibodies that bind the head generally have hemagglutination inhibition (HI) activity, whereas antibodies that bind to the stalk domain of HA do not but neutralize by post-entry mechanisms of inhibition (21, 22). The H7N9 neutralizing antibodies herein showed no HI activity against any tested strain (data not shown). Moreover, competitive inhibition using CR9114, a previously described stalk-reactive antibody (Dreyfus et al. Science. 2012; 337(6100):1343-8; herein incorporated by reference in its entirety), indicated that the epitopes targeted by the three antibodies are within the stalk domain of HA (FIG. 4B). 009-10061-1D04, an antibody that displays HI activity (FIG. 7C) and binds to H3N2 and H7 strains (FIG. 1A), was not inhibited by any of the stalk antibodies tested (FIG. 7B).

To further map the epitopes targeted by the three neutralizing antibodies, escape mutants of the A/Shanghai/1/2013 (H7N9) virus were generated. It is postulated that under antibody pressure, viruses undergo mutations at sites that are targeted by the antibody and that allows the identification of the binding site. Four escape mutants were sequenced for each antibody and the mutations were analyzed. The same virus passaged in absence of antibody was used as a control. All four clones for each antibody displayed the same mutations. None of the mutations were found with the virus passaged without antibody suggesting that the mutations were a result of the antibody pressure. A total of three amino acid substitutions were identified for each antibody in the HA segment (table 3). Interestingly, mutations both in the stalk and the head domains were observed. The escape mutant generated with the antibody 045-051310-2B06 displayed two mutations in the stalk region, V318I and I384N (H7 numbering starting with methionine), and one in the globular head region, G195E. The escape mutant generated with the antibody S6-B01 displayed one mutation in the stalk region, I384T. This mutation arose at the same residue as the escape mutant generated by 045-051310-2B06 but the substitution was different. Both mutations at this residue were located in the conserved epitope targeted by CR9114

(19). Two mutations in the globular head, A198E and G214E, were also found. Finally, the escape mutant generated with the antibody 042-100809-2F04 displayed one mutation in the stalk region, R364K, and two in the globular head region, G63E and G234D. The stalk mutation was located in the conserved epitope targeted by CR8020, a group 2 neutralizing antibody (Ekiert et al. Science. 2011; 333(6044):843-50; herein incorporated by reference in its entirety).

TABLE 3

Mutations displayed by the escape mutants

| | Head mutations | Stalk mutations |
|---|---|---|
| 045-051310-2B06 | G195E | V318I |
| | | I384N |
| 042-100809-2F04 | G63E | R364K |
| | G234D | |
| S6-B01 | A198E | I384T |
| | G214E | |

Example 3

Escape Mutants

Escape-Mediated Loss of Binding is Complete for 045-051310-2B06 and 042-100809-2F04 but not for S6-B01

To test the effect of the mutations on antibody binding, MDCK cells were infected with the original virus (A/Shanghai/1/2013) or the different escape mutant viruses, and the binding of each antibody to the cells was assessed by immunofluorescence. MDCK cells were infected with the different escape mutant viruses (045-051310-2B06, 042-100809-2F04 or 56-B01) or the wild type A/Shanghai/1/2013 virus, and incubated with the neutralizing antibodies, individually, at 5 µg/ml. A mouse anti-M2 protein antibody (E10) was used as a positive control of infection for each virus variants. Binding was visualized using an anti-IgG Alexa. Fluor 488 conjugated antibody under an Olympus 1X70 inverted fluorescence microscope. The magnification was 100×. 045-051310-2B06 had no detectable binding when the cells were infected with its corresponding escape mutant, suggesting that the mutations affect antigenicity (Hensley et al. Science. 2009; 326(5953):734-6; herein incorporated by reference in its entirety). There was also no binding for 045-051310-2B06 to the escape mutant generated from S6-B01. Interestingly, for the S6-B01 antibody, binding to both of these escape mutants was only partially lost. Finally, the 042-100809-2F04 antibody lost binding to its own escape mutant, but not to the escape mutants generated from the other two antibodies. These results confirm that the neutralizing cross-reactive antibodies bind to two different epitopes on the HA-stalk domain.

To determine the role of the head versus stalk domain mutations, different variants of the mutated recombinant HAs were expressed. For each of the three escape mutants, two HAs were generated and assessed antibody binding by ELISA; the first HA incorporated the mutations in both the head and the stalk domains while the second HA incorporated only the stalk mutations with a wild type globular head domain. Reduced binding to both mutated HAs for the antibody 045-051310-2B06 was observed (FIGS. 8A-C). However, the loss of binding was more dramatic with the stalk-only mutated HA, suggesting that the stalk mutations are antigenic mutations. The same pattern of binding was detected when CR9114 was tested with the 045-051310-2B06 HA variants. In line with the immunofluorescence observations, a slightly reduced binding was seen with the fully mutated HAs for S6-B01. However, there was no reduction in binding to the stalk-only mutated HA. This finding was confirmed using CR9114, which has the same footprint as 045-051310-2B06 and S6-B01. Therefore, although these mutations mediate viral escape from neutralization by the antibody, they do not ablate antibody binding. Finally, 042-100809-2F04 showed reduced binding to its own HA mutants (both mutated stalk-only and fully mutated HAs). But the loss of binding was more dramatic when both the head and the stalk mutations were present. This was confirmed with CR8020, which has the same footprint as 042-100809-2F04.

Escape Mutant Viruses have Diminished Pathogenicity In Vivo

To evaluate the importance of the stalk mutations in the loss of viral fitness, infectious reassortant viruses with these mutations were generated for each of the three antibodies and the $LD_{50}$ of the different viruses in mice was determined. Experiments were conducted with different challenge doses, ranging from 100 to 100,000 PFU per mouse. Although the 045-051310-2B06 and S6-B01 escape mutants probably share the same epitope, the lethality of the two mutants compared to the parental A/Shanghai H7N9 strain were quite different. The 045-051310-2B06 escape mutant was highly attenuated ($LD_{50}>1·10^5$) compared to the wild-type A/Shanghai H7N9 strain ($LD_{50}=4.6·10^3$), and none of the mice succumbed to infection. In contrast, the S6-B01 escape mutant closely mimicked the parental strain and all mice challenged with 100,000 PFU succumbed to infection. However, the $LD_{50}$ of the S6-B01 mutant ($LD_{50}=3.2·10^4$) was still higher that of the wild-type A/Shanghai H7N9 strain. The 042-100809-2F04 escape mutant was moderately attenuated ($LD_{50}=5.2·10^4$) (FIG. 9). All together, these results demonstrate that escape from stalk-reactive antibodies impacts negatively on virus fitness in vivo.

The Loss of Binding Observed for 042-100809-2F04 is Only Mediated by Escape Mutations in the HA-Stalk Domain It was demonstrated that the phenotype of the 045-051310-2B06 escape mutant was dependent on the stalk mutations (complete loss of binding and loss of viral fitness). Results also demonstrate that 045-051310-2B06 and S6-B01 bind to the same epitope on the stalk region. For the 042-100809-2F04 escape mutant, the loss of binding was more dramatic when the head and stalk mutations were combined. In addition, the pathogenicity of the escape mutant viruses was moderate. In order to confirm that the mutations in the stalk domain are responsible for antibody binding, infectious reassortant viruses were generated with individual head and stalk mutations. Immunofluorescence was used to characterize antibody binding to four 042-100809-2F04 point-mutant viruses: R364K (stalk mutation), G63E/G234D (head mutations), G63E, and G234D. 042-100809-2F04 bound to the wild type A/Shanghai H7N9 virus and to all combinations of the head domain mutations reassortants (G63E/G234D, G63E and G234D). MDCK cells were infected with viruses containing different combinations of point-mutations (R364K (stalk mutation), G63E/G234D (head mutations), G63E, and G234D), the full escape mutant (G63E/G234D/R364K), or the wild type A/Shanghai/1/2013 virus, then incubated with 042-100809-2F04 antibody at 5 µg/ml. A polyclonal serum was used as a positive control of infection for each virus variant. The antibody 6F12 was used as a negative control. Binding was visualized using an anti-IgG Alexa Fluor 488 conjugated antibody under an Olympus 1X70 inverted fluorescence microscope. Magnification was 100×. Binding to the stalk escape mutant (R364K) was lost, as well as binding to the control full escape mutant (G63E/G234D/R364K).

To further characterize these point-mutant viruses, viral replication was observed under the presence of antibody pressure (042-100809-2F04) in vitro via a microneutralization assay. In line with the above results, the full 042-100809-2F04 escape mutant (G63E/G234D/R364K) evaded antibody neutralization, as well as virus with the stalk mutation alone (R364K). In contrast, all combinations of mutations on the head domain failed to evade antibody neutralization. 042-100809-2F04 neutralized the wild type A/Shanghai H7N9 virus (FIG. 7). These results confirm that the binding site of 042-100809-2F04 is on the HA-stalk domain.

Example 4

Antibody 41-5E04

Antibody 41-5E04 was isolated from plasmablasts at day 7 after an inactivated virus vaccine H7N9. The individual had received two doses of a live attenuated cold-adapted influenza A/Anhui/1/2013 (H7N9) vaccine and then boosted 12 weeks later with an inactivated virus vaccine based on the closely related Shanghai/2/2013 (H7N9) strain. Plasmablasts were isolated 7 days after administration of the inactivated vaccine, then single-cell sorted and antibodies were cloned as previously described (Smith et al., 2009; Wrammert et al., 2008; herein incorporated by reference in their entireties).

41-5E04 binds to both group 1 and 2 HA proteins and neutralizes viruses in vitro (FIG. 11).

6-8 week old female BALB/c mice were treated prophylactically with 0.3, 1, or 5 mg/kg of 41-5E04 intraperitoneally and then challenged with a lethal dose (7.5 LD50) of A/Shanghai/1/2013 (H7N9) virus (FIG. 12). Doses were as low as 0.3 mg/kg All publications and patents provided herein are incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

SEQUENCES

The following sequences are references throughout by their corresponding SEQ ID NOs.

DY-2F04H
SEQ ID NO: 1
GAGGTGCAGCTGGTGGAGTCTGGGGGAGGCTTGGTCCAGCCTGGGGGGTC
CCTGAGACTCTCCTGTGTAGCCTCTGGATTCACCTTTAGTACTCCTTGGA
TGACGTGGATCCGCCAGGCTCCAGGGAAGGGGCTGGAGTGGGTGGCCCAC
ATAAAGCAGGATGGAAGTGAGACATACTATGTGGACTCTGTGAAGGGCCG
ATTCACCATCTCCAGAGACAACGCCAAGAACTCACTGTATCTGCAAATGA
ACAGCCTGAAAGCCGAGGACACGGCTTTATATTACTGTGCGAGAATGACG
CGGGAATCATCAGAAAACTACTGGGGCCAGGGAACCCTGGTCACCGTCTC
CTCAG

MP-2B06H
SEQ ID NO: 2
CAGGTGCAGCTGGTGCAGTCTGGACCTGAGATGAAGAAGCCTGGGGCCTC
AGTGAAGGTCTCCTGCAAGACTTCTGGTTACAGGTTTACCAGATATGGGA
TCAGTTGGGTGCGGCAGGCCCCTGGACGGGGGCTGGAGTGGCTGGGGTGG
ATCAGCGCATACAGTGGAGACACATATTATGGACAGAAATTCCAGGACAG
AGTCACCATGACTACAGACAGAGCCACGAGTACAGCCTATATGGAGTTGC
GGAACCTGGGATCTGACGACTCGGCCGTTTATTTCTGTGCGAGAGATCAC
GTCCAAGGGGAAGTGAGCATATATTATTATGCCATGGACGTCTGGGGCGA
AGGGACCACGGTCACCGTCTCCTCA

1B01H
SEQ ID NO: 3
CAGGTGCAGCTGGTGCAGTCTGGAGCTGAGGTGAAGAAGCCCGGGGCCTC
AGTGAAGGTCTCCTGCAAGGCTTCTGGTTACACGTTTAACAGCTATGGAA
TCAGTTGGGTGCGACAGGCCCCCGGACAAGGGCTTGAGTGGATGGGATGG
ATCAGCGCTTACACTGGCGACACAAAGTTTGCACAGAATGTGCAGGGCAG
AGTCACCATGACCATAGACACATCCACGAGTACCGCCTACATGGAACTGA
GGAGCCTGAGATCTGACGACACGGCCGTATATTACTGTGCGAGACATTAC
CTCCAAGGGGTAGTAGTGGTTGACCCCTACTCCCACGCTATGGACGTCTG
GGGCCAAGGGACCACGGTCACCGTCTCCTCA

DY2F04K
SEQ ID NO: 4
GATGTTGTGATGACTCAGTCTCCACTCTCCTTGCCCGTCACCCTTGGCCA
GCCGGCCTCCATCTCCTGCAGGTCTAGTCAAAGCCTCGTATACAGTGATG
GAGACACCTTCCTGGAATGGTTTCAGCAGAGGCCAGGCCAATCTCCAAGG
CGCCTAATTTATAAGGTTTCTAACCGGGATTCTGGGGTCCCAGACAGATT
CAGCGGCAGTGGGTCAGGCACTGATTTCACACTGAAAATCAGCAGGGTGG
AGGCTGAGGATGTTGGGCTTTATTACTGCATGCAACATACACACTGGCCG
CACACTTTTGGCCAGGGGACCAAGGTGGAGATCAAAC

MP-2B06K
SEQ ID NO: 5
GAAATTGTGTTGACACAGTCTCCAGCCACCCTGTCTTTGTCTCCAGGAGA
AAGAGTCACCCTCTCCTGCAGGGCCAGTGAGAGTGTTGGCAACAAGTTAG
CCTGGTTCCAACAGAGGCCTGGCCAGGCTCCCAGGCTCCTCATTTATAAT
GCATCCAACAGGGCCACTGACATCCCAGCCAGGTTCAGTGGCAGTGGGTC
TGGGACAGACTTCACTCTCACCATCAGCAGCCTGCAGCCTGAAGATTTTG
CAGTTTATTACTGTCAGCAGCGTGGCACGTGGCCTCGGGGCCTCATCACC
TTCGGCCAAGGGACACGACTGGAGATTAAAC

1B01K
SEQ ID NO: 6
GAAATTGTGTTGACGCAGTCTCCAGGCACCCTGTCTTTCTTTCCAGGGGA
AAGAGCCACCCTCTCCTGCAGGGCCAGTCAAACTATTAACAGCAGATTCT

-continued
```
TAGCCTGGTATCAGCAGAAACCTGGCCAGGCTCCCAGGCTCCTCATCTAT

GGTGCATCCAGCCGGGCCACTGGCATCCCGGACAGGTTCAGTGGCCGTGG

GTCTGGGACAGACTTCACTCTCGCCATCAGCAGACTGGAGCCTGAGGATT

TTGCAGTGTATTACTGTCAGTTGTATGGTAGCTCACGGACGACTTTTGGC

CAGGGGACCAAGGTGGAGATCAAAC
```

DY-2F04H
SEQ ID NO: 7
```
EVQLVESGGGLVQPGGSLRLSCVASGFTFSTPWMTWIRQAPGKGLEWVAH

IKQDGSETYYVDSVKGRFTISRDNAKNSLYLQMNSLKAEDTALYYCARMT

RESSENYWGQGTLVTVSS
```

MP-2B06H
SEQ ID NO: 8
```
QVQLVQSGPEMKKPGASVKVSCKTSGYRFTRYGISWVRQAPGRGLEWLGW

ISAYSGDTYYGQKFQDRVTMTTDRATSTAYMELRNLGSDDSAVYFCARDH

VQGEVSIYYYAMDVWGEGTTVTVSS
```

1B01H
SEQ ID NO: 9
```
QVQLVQSGAEVKKPGASVKVSCKASGYTFNSYGISWVRQAPGQGLEWMGW

ISAYTGDTKFAQNVQGRVTMTIDTSTSTAYMELRSLRSDDTAVYYCARHY

LQGVVVVDPYSHAMDVWGQGTTVTVSS
```

DY2F04K
SEQ ID NO: 10
```
DVVMTQSPLSLPVTLGQPASISCRSSQSLVYSDGDTFLEWFQQRPGQSPR

RLIYKVSNRDSGVPDRFSGSGSGTDFTLKISRVEAEDVGLYYCMQHTHWP

HTFGQGTKVEIK
```

MP-2B06K
SEQ ID NO: 11
```
EIVLTQSPATLSLSPGERVTLSCRASESVGNKLAWFQQRPGQAPRLLIYN

ASNRATDIPARFSGSGSGTDFTLTISSLQPEDFAVYYCQQRGTWPRGLIT

FGQGTRLEIK
```

1B01K
SEQ ID NO: 12
```
EIVLTQSPGTLSFFPGERATLSCRASQTINSRFLAWYQQKPGQAPRLLIY

GASSRATGIPDRFSGRGSGTDFTLAISRLEPEDFAVYYCQLYGSSRTTFG

QGTKVEIK
```

DY2F04 HCDR1
SEQ ID NO: 13
GFTFSTPW

DY2F04 HCDR2
SEQ ID NO: 14
IKQDGSET

DY2F04 HCDR3
SEQ ID NO: 15
ARMTRESSENY

MP-2B06 HCDR1
SEQ ID NO: 16
GYRFTRYG

MP-2B06 HCDR2
SEQ ID NO: 17
ISAYSGDT

MP-2B06 HCDR3
SEQ ID NO: 18
ARDHVQGEVSIYYYAMDV

HCDR1
SEQ ID NO: 19
GYTFNSYG

1B01 HCDR2
SEQ ID NO: 20
ISAYTGDT

1B01 HCDR3
SEQ ID NO: 21
ARHYLQGVVVVDPYSHAMDV

DY2F04 KCDR1
SEQ ID NO: 22
QSLVYSDGDTF

DY2F04 KCDR2
SEQ ID NO: 23
KVS

DY2F04 KCDR3
SEQ ID NO: 24
MQHTHWPHT

MP-2B06 KCDR1
SEQ ID NO: 25
ESVGNK

MP-2B06 KCDR2
SEQ ID NO: 26
NAS

MP-2B06 KCDR3
SEQ ID NO: 27
QQRGTWPRGLIT

1B01 KCDR1
SEQ ID NO: 28
QTINSRF

1B01 KCDR2
SEQ ID NO: 29
GAS

1B01 KCDR3
SEQ ID NO: 30
QLYGSSRTT

5E04H
SEQ ID NO: 33
```
GAGGTGCAGCTGGTGGAGTCTGGAGGAGGCTTGATAAACCCTGGGGGGTC

CCTGAGACTCTCCTGTGCAGCCTCTGGTTTCAACATCGATAACAACCAAA

TGATTTGGGTCCGCCAGGCTCCAAAGAAGGGCCTGGAGTGGGTCTCACTT

ATTTATAGCGGTGGTTCTACATATTCCGCAGACACCGTGAAGGGCCGATT

CACCATCTCCAGAGACAATTCCAAGAACACAGTGTATCTTCACATGAACA

GTCTGCGAGCCGAGGACACGGCCGTGTATTATTGTGCGAGAGATTTTCTC

AGGGGACCAATACATGATTACTTTTTCTACATGGACGTCTGGGGCAAGGG

GACCACGGTCACCGTCTCCTCA
```

5E04K
SEQ ID NO: 34
```
GAAATTGTGTTGACACAGTCTCCAGCCTCCCTGTCTTTGTCTCCAGGGGA

AAGAGCCACCCTCTCCTGCAGGGCCAGTCAGAGGGTTGACAGCTCCATAG

GCTGGTACCGACACAAACCTGGTCAGGCTCCCAGGCTCCTCATCTATGAT

GCAATTAAAAGGGCCACTGGCATCCCAGCCAGATTCAGTGGCAGTGGATA

TGGGACAGACTTCACTCTTACCATCAGCCGCCTAGAGGCTGAAGATTTTG

CAGTTTATTACTGTCAGCAGCGTAGCACCTGGCCCACTTTCGGCCCTGGG
```

```
                                -continued
ACCAAAGTGGATATCAAAC

5E04H
                                                  SEQ ID NO: 35
EVQLVESGGGLINPGGSLRLSCAASGFNIDNNQMIWVRQAPKKGLEWVSL

IYSGGSTYSADTVK

GRFTISRDNSKNTVYLHMNSLRAEDTAVYYCARDFLRGPIHDYFFYMDVW

GKGTTVTVSS

5E04K
                                                  SEQ ID NO: 36
EIVLTQSPASLSLSPGERATLSCRASQRVDSSIGWYRHKPGQAPRLLIYD

AIKRATGIPARFSGSGYGTDFTLTISRLEAEDFAVYYCQQRSTWPTFGPG

TKVDIK

5E04-HCDR1
                                                  SEQ ID NO: 37
GFNIDNNQ

5E04-HCDR2
                                                  SEQ ID NO: 38
IYSGGST

5E04-HCDR3
                                                  SEQ ID NO: 39
ARDFLRGPIHDYFFYMDV

5E04-KCDR1
                                                  SEQ ID NO: 40
QRVDSS

5E04-KCDR2
                                                  SEQ ID NO: 41
DAT

5E04-KCDR3
                                                  SEQ ID NO: 42
QQRSTWPT
```

REFERENCES

The following references are herein incorporated by reference in their entireties.

Shaw M L and Palese P. Orthomyxoviruses. In: Knipe D M, Howley P M, eds. Fields Virology. Philadelphia, Pa., USA: Lippincott Williams and Wilkins; 2013.

Kaur K, Sullivan M, and Wilson P C. Targeting B cell responses in universal influenza vaccine design. Trends in immunology. 2011; 32(11):524-31.

Air G M. Sequence relationships among the hemagglutinin genes of 12 subtypes of influenza A virus. Proc Natl Acad Sci USA. 1981; 78(12):7639-43.

Medina R A, and Garcia-Sastre A. Influenza A viruses: new research developments. Nat Rev Microbiol. 2011; 9(8): 590-603.

Hirst M, Astell C R, Griffith M, Coughlin S M, Moksa M, Zeng T, Smailus D E, Holt R A, Jones S, Marra M A, et al. Novel avian influenza H7N3 strain outbreak, British Columbia. Emerg Infect Dis. 2004; 10(12):2192-5.

Fouchier R A, Schneeberger P M, Rozendaal F W, Broekman J M, Kemink S A, Munster V, Kuiken T, Rimmelzwaan G F, Schutten M, Van Doornum G J, et al. Avian influenza A virus (H7N7) associated with human conjunctivitis and a fatal case of acute respiratory distress syndrome. Proc Natl Acad Sci USA. 2004; 101(5):1356-61.

Gao R, Cao B, Hu Y, Feng Z, Wang D, Hu W, Chen J, Jie Z, Qiu H, Xu K, et al. Human infection with a novel avian-origin influenza A (H7N9) virus. N Engl J Med. 2013; 368(20):1888-97.

Belser J A, Gustin K M, Pearce M B, Maines T R, Zeng H, Pappas C, Sun X, Carney P J, Villanueva J M, Stevens J, et al. Pathogenesis and transmission of avian influenza A (H7N9) virus in ferrets and mice. Nature. 2013.

Watanabe T, Kiso M, Fukuyama S, Nakajima N, Imai M, Yamada S, Murakami S, Yamayoshi S, Iwatsuki-Horimoto K, Sakoda Y, et al. Characterization of H7N9 influenza A viruses isolated from humans. Nature. 2013.

Morens D M, Taubenberger J K, and Fauci A S. H7N9 Avian Influenza A Virus and the Perpetual Challenge of Potential Human Pandemicity. MBio. 2013; 4(4).

Hu Y, Lu S, Song Z, Wang W, Hao P, Li J, Zhang X, Yen H L, Shi B, Li T, et al. Association between adverse clinical outcome in human disease caused by novel influenza A H7N9 virus and sustained viral shedding and emergence of antiviral resistance. Lancet. 2013; 381(9885):2273-9.

Zhang Q, Shi J, Deng G, Guo J, Zeng X, He X, Kong H, Gu C, Li X, Liu J, et al. H7N9 influenza viruses are transmissible in ferrets by respiratory droplet. Science. 2013; 341(6144):410-4.

Xu R, de Vries R P, Zhu X, Nycholat C M, McBride R, Yu W, Paulson J C, and Wilson I A. Preferential recognition of avian-like receptors in human influenza A H7N9 viruses. Science. 2013; 342(6163): 1230-5.

Ramos I, Krammer F, Hai R, Aguilera D, Bernal-Rubio D, Steel J, Garcia-Sastre A, and Fernandez-Sesma A. H7N9 influenza viruses interact preferentially with alpha2,3-linked sialic acids and bind weakly to alpha2,6-linked sialic acids. The Journal of general virology. 2013; 94 (Pt 11):2417-23.

Hai R, Schmolke M, Leyva-Grado V H, Thangavel R R, Margine I, Jaffe E L, Krammer F, Solorzano A, Garcia-Sastre A, Palese P, et al. Influenza A(H7N9) virus gains neuraminidase inhibitor resistance without loss of in vivo virulence or transmissibility. Nature communications. 2013; 4(2854.

Wrammert J, Koutsonanos D, Li G M, Edupuganti S, Sui J, Morrissey M, McCausland M, Skountzou I, Hornig M, Lipkin W I, et al. Broadly cross-reactive antibodies dominate the human B cell response against 2009 pandemic H1N1 influenza virus infection. J Exp Med. 2011; 208 (1):181-93.

Wrammert J, Smith K, Miller J, Langley W A, Kokko K, Larsen C, Zheng N Y, Mays I, Garman L, Helms C, et al. Rapid cloning of high-affinity human monoclonal antibodies against influenza virus. Nature. 2008; 453(7195): 667-71.

Krammer F, Jul-Larsen A, Margine I, Hirsh A, Sjursen H, Zambon M, and Cox R J. An H7N1 influenza virus vaccine induces broadly reactive antibody responses against H7N9 in humans. Clinical and vaccine immunology: CVI. 2014.

Dreyfus C, Laursen N S, Kwaks T, Zuijdgeest D, Khayat R, Ekiert D C, Lee J H, Metlagel Z, Bujny M V, Jongeneelen M, et al. Highly conserved protective epitopes on influenza B viruses. Science. 2012; 337(6100):1343-8.

Kapczynski D R, Pantin-Jackwood M, Guzman S G, Ricardez Y, Spackman E, Bertran K, Suarez D L, and Swayne D E. Characterization of the 2012 highly pathogenic avian influenza H7N3 virus isolated from poultry in an outbreak in Mexico: pathobiology and vaccine protection. J Virol. 2013; 87(16):9086-96.

Brandenburg B, Koudstaal W, Goudsmit J, Klaren V, Tang C, Bujny M V, Korse H J, Kwaks T, Otterstrom J J, Juraszek J, et al. Mechanisms of hemagglutinin targeted influenza virus neutralization. PLoS One. 2013; 8(12): e80034.

Tan G S, Lee P S, Hoffman R M, Mazel-Sanchez B, Krammer F, Leon P E, Ward A B, Wilson I A, and Palese P. Characterization of a broadly neutralizing monoclonal antibody that targets the fusion domain of group 2 influenza a virus hemagglutinin. J Virol. 2014; 88(23):13580-92.

Ekiert D C, Friesen R H, Bhabha G, Kwaks T, Jongeneelen M, Yu W, Ophorst C, Cox F, Korse H J, Brandenburg B, et al. A highly conserved neutralizing epitope on group 2 influenza A viruses. Science. 2011; 333(6044):843-50.

Hensley S E, Das S R, Bailey A L, Schmidt L M, Hickman H D, Jayaraman A, Viswanathan K, Raman R, Sasisekharan R, Bennink J R, et al. Hemagglutinin receptor binding avidity drives influenza A virus antigenic drift. Science. 2009; 326(5953):734-6.

Corti D, Suguitan A L, Jr., Pinna D, Silacci C, Fernandez-Rodriguez B M, Vanzetta F, Santos C, Luke C J, Torres-Velez F J, Temperton N J, et al. Heterosubtypic neutralizing antibodies are produced by individuals immunized with a seasonal influenza vaccine. J Clin Invest. 2010; 120(5):1663-73.

Li G M, Chiu C, Wrammert J, McCausland M, Andrews S F, Zheng N Y, Lee J H, Huang M, Qu X, Edupuganti S, et al. Pandemic H1N1 influenza vaccine induces a recall response in humans that favors broadly cross-reactive memory B cells. Proc Natl Acad Sci USA. 2012; 109(23): 9047-52.

Thomson C A, Wang Y, Jackson L M, Olson M, Wang W, Liavonchanka A, Keleta L, Silva V, Diederich S, Jones R B, et al. Pandemic H1N1 Influenza Infection and Vaccination in Humans Induces Cross-Protective Antibodies that Target the Hemagglutinin Stem. Frontiers in immunology. 2012; 3(87.

Wilson P C, and Andrews S F. Tools to therapeutically harness the human antibody response. Nature reviews Immunology. 2012; 12(10):709-19.

Ekiert D C, Kashyap A K, Steel J, Rubrum A, Bhabha G, Khayat R, Lee J H, Dillon M A, O'Neil R E, Faynboym A M, et al. Cross-neutralization of influenza A viruses mediated by a single antibody loop. Nature. 2012; 489 (7417):526-32.

Margine I, Hai R, Albrecht R A, Obermoser G, Harrod A C, Banchereau J, Palucka K, Garcia-Sastre A, Palese P, Treanor J J, et al. H3N2 influenza virus infection induces broadly reactive hemagglutinin stalk antibodies in humans and mice. J Virol. 2013; 87(8):4728-37.

Margine I, Krammer F, Hai R, Heaton N S, Tan G S, Andrews S A, Runstadler J A, Wilson P C, Albrecht R A, Garcia-Sastre A, et al. Hemagglutinin Stalk-Based Universal Vaccine Constructs Protect against Group 2 Influenza A Viruses. J Virol. 2013; 87(19):10435-46.

Krammer F, Margine I, Hai R, Flood A, Hirsh A, Tsvetnitsky V, Chen D, and Palese P. H3 stalk-based chimeric hemagglutinin influenza virus constructs protect mice from H7N9 challenge. J Virol. 2014; 88(4):2340-3.

Ekiert D C, Bhabha G, Elsliger M A, Friesen R H, Jongeneelen M, Throsby M, Goudsmit J, and Wilson I A. Antibody recognition of a highly conserved influenza virus epitope. Science. 2009; 324(5924):246-51.

Friesen R H, Lee P S, Stoop E J, Hoffman R M, Ekiert D C, Bhabha G, Yu W, Juraszek J, Koudstaal W, Jongeneelen M, et al. A common solution to group 2 influenza virus neutralization. Proc Natl Acad Sci USA. 2014; 111(1): 445-50.

O'Donnell C D, Vogel L, Wright A, Das S R, Wrammert J, Li G M, McCausland M, Zheng N Y, Yewdell J W, Ahmed R, et al. Antibody pressure by a human monoclonal antibody targeting the 2009 pandemic H1N1 virus hemagglutinin drives the emergence of a virus with increased virulence in mice. MBio. 2012; 3(3).

Wang T T, Tan G S, Hai R, Pica N, Petersen E, Moran T M, and Palese P. Broadly protective monoclonal antibodies against H3 influenza viruses following sequential immunization with different hemagglutinins. PLoS Pathog. 2010; 6(2):e1000796.

Corti D, Voss J, Gamblin S J, Codoni G, Macagno A, Jarrossay D, Vachieri S G, Pinna D, Minola A, Vanzetta F, et al. A neutralizing antibody selected from plasma cells that binds to group 1 and group 2 influenza A hemagglutinins. Science. 2011; 333(6044):850-6.

Throsby M, van den Brink E, Jongeneelen M, Poon L L, Alard P, Cornelissen L, Bakker A, Cox F, van Deventer E, Guan Y, et al. Heterosubtypic neutralizing monoclonal antibodies cross-protective against H5N1 and H1N1 recovered from human IgM+ memory B cells. PLoS One. 2008; 3(12):e3942.

Sui J, Hwang W C, Perez S, Wei G, Aird D, Chen L M, Santelli E, Stec B, Cadwell G, Ali M, et al. Structural and functional bases for broad-spectrum neutralization of avian and human influenza A viruses. Nat Struct Mol Biol. 2009; 16(3):265-73.

Krammer F, Albrecht R A, Tan G S, Margine I, Hai R, Schmolke M, Runstadler J, Andrews S F, Wilson P C, Cox R J, et al. Divergent H7 immunogens offer protection from H7N9 virus challenge. J Virol. 2014; 88(8):3976-85.

Margine I, Palese P, and Krammer F. Expression of functional recombinant hemagglutinin and neuraminidase proteins from the novel H7N9 influenza virus using the baculovirus expression system. Journal of visualized experiments: JoVE. 201381):e51112.

Crotty S, Aubert R D, Glidewell J, and Ahmed R. Tracking human antigen-specific memory B cells: a sensitive and generalized ELISPOT system. Journal of immunological methods. 2004; 286(1-2):111-22.

Quinlivan M, Zamarin D, Garcia-Sastre A, Cullinane A, Chambers T, and Palese P. Attenuation of equine influenza viruses through truncations of the NS1 protein. J Virol. 2005; 79(13): 8431-9.

Fodor E, Devenish L, Engelhardt O G, Palese P, Brownlee G G, and Garcia-Sastre A. Rescue of influenza A virus from recombinant DNA. J Virol. 1999; 73(11):9679-82.

Hai R, Krammer F, Tan G S, Pica N, Eggink D, Maamary J, Margine I, Albrecht R A, and Palese P. Influenza viruses expressing chimeric hemagglutinins: globular head and stalk domains derived from different subtypes. J Virol. 2012; 86(10):5774-81.

Smith K, Garman L, Wrammert J, Zheng N Y, Capra J D, Ahmed R, and Wilson P C. Rapid generation of fully human monoclonal antibodies specific to a vaccinating antigen. Nat Protoc. 2009; 4(3):372-84.

The invention claimed is:

1. A binding agent, comprising:
   (a) a first CDR1 of SEQ ID NO: 13; a first CDR2 of SEQ ID NO: 14; a first CDR3 of SEQ ID NO: 15; a second CDR1 of SEQ ID NO: 22; a second CDR2 of SEQ ID NO: 23; and a second CDR3 of SEQ ID NO: 24;
   (b) a first CDR1 of SEQ ID NO: 16; a first CDR2 of SEQ ID NO: 17; a first CDR3 of SEQ ID NO: 18; a second CDR1 of SEQ ID NO: 25; a second CDR2 of SEQ ID NO: 26; and a second CDR3 of SEQ ID NO: 27;
   (c) a first CDR1 of SEQ ID NO: 19; a first CDR2 of SEQ ID NO: 20; a first CDR3 of SEQ ID NO: 21; a second CDR1 of SEQ ID NO: 28; a second CDR2 of SEQ ID NO: 29; and a second CDR3 of SEQ ID NO: 30; or
   (d) a first CDR1 of SEQ ID NO: 37; a first CDR2 of SEQ ID NO: 38; a first CDR3 of SEQ ID NO: 39; a second CDR1 of SEQ ID NO: 40; a second CDR2 of SEQ ID NO: 41; and a second CDR3 of SEQ ID NO: 42.

2. The binding agent of claim 1, comprising: a first CDR1 of SEQ ID NO: 16; a first CDR2 of SEQ ID NO: 17; a first CDR3 of SEQ ID NO: 18; a second CDR1 of SEQ ID NO: 25; a second CDR2 of SEQ ID NO: 26; and a second CDR3 of SEQ ID NO: 27.

3. The binding agent of claim 1, comprising: a first CDR1 of SEQ ID NO: 19; a first CDR2 of SEQ ID NO: 20; a first CDR3 of SEQ ID NO: 21; a second CDR1 of SEQ ID NO: 28; a second CDR2 of SEQ ID NO: 29; and a second CDR3 of SEQ ID NO: 30.

4. The binding agent of claim 1, comprising: a first CDR1 of SEQ ID NO: 37; a first CDR2 of SEQ ID NO: 38; a first CDR3 of SEQ ID NO: 39; a second CDR1 of SEQ ID NO: 40; a second CDR2 of SEQ ID NO: 41; and a second CDR3 of SEQ ID NO: 42.

5. The binding agent of claim 1, wherein the binding agent has an affinity for the epitope of at least $10^7$ $M^{-1}$.

6. The binding agent of claim 1, wherein the first CDR sequences and the second CDR sequences are on first and second polypeptides.

7. The binding agent of claim 1, wherein the first CDR sequences and the second CDR sequences are on a single polypeptide.

8. The binding agent of claim 1, wherein the binding agent is a monoclonal antibody or monobody.

9. The binding agent of claim 1 wherein the binding agent is an antibody fragment.

10. The binding agent of claim 1, comprising binding affinity for an epitope displayed on an H7N9 influenza strain.

11. The binding agent of claim 1, comprising binding affinity for an epitope displayed on an H1N1 influenza strain.

12. The binding agent of claim 1, comprising binding affinity for an epitope displayed on an H3N2 influenza strain.

13. A method of treating a subject for influenza comprising administering a binding agent of claim 1 to the subject.

14. The method of claim 13, wherein the subject is human.

15. The method of claim 13, wherein the subject is infected with influenza.

16. A method of preventing influenza in a subject comprising administering a binding agent of claim 1 to the subject.

17. The method of claim 13, wherein said binding agent is co-administered with one or more additional therapeutic agents selected from the group consisting of antivirals, immunologic agents, antibiotics, and agents for relieving symptoms of influenza infection.

18. The binding agent of claim 1, comprising: a first CDR1 of SEQ ID NO: 13; a first CDR2 of SEQ ID NO: 14; a first CDR3 of SEQ ID NO: 15; a second CDR1 of SEQ ID NO: 22; a second CDR2 of SEQ ID NO: 23; and a second CDR3 of SEQ ID NO: 24.

19. The method of claim 16, wherein the subject is at risk of influenza infection.

20. The method of claim 16, wherein the subject is human.

* * * * *

SEQUENCE LISTING

<160> NUMBER OF SEQ ID NOS: 42

<210> SEQ ID NO 1

```
<211> LENGTH: 355
<212> TYPE: DNA
<213> ORGANISM: Homo sapiens

<400> SEQUENCE: 1
gaggtgcagc tggtggagtc tgggggaggc ttggtccagc ctgggggtc  cctgagactc    60 tcctgtgtag cctctggatt cacctttagt actccttgga tgacgtggat ccgccaggct   120
ccagggaagg gctggagtg gtggcccac ataaagcagg atggaagtga gacatactat     180
gtggactctg tgaagggccg attcaccatc tccagagaca cgccaagaa ctcactgtat    240 ctgcaaatga acagcctgaa agccgaggac acggctttat attactgtgc gagaatgacg   300
cgggaatcat cagaaaacta ctggggccag ggaaccctgg tcaccgtctc ctcag         355

<210> SEQ ID NO 2
<211> LENGTH: 375
<212> TYPE: DNA
<213> ORGANISM: Homo sapiens

<400> SEQUENCE: 2
caggtgcagc tggtgcagtc tggacctgag atgaagaagc ctggggcctc agtgaaggtc    60
tcctgcaaga cttctggtta caggtttacc agatatggga tcagttgggt gcggcaggcc   120
cctggacggg gctggagtg gctggggtgg atcagcgcat acagtggaga cacatattat    180
ggacagaaat tccaggacag agtcaccatg actacagaca gagccacgag tacagcctat   240
atggagttgc ggaacctggg atctgacgac tcggccgttt atttctgtgc gagagatcac   300
gtccaagggg aagtgagcat atattattat gccatggacg tctggggcga agggaccacg   360
gtcaccgtct cctca                                                    375

<210> SEQ ID NO 3
<211> LENGTH: 381
<212> TYPE: DNA
<213> ORGANISM: Homo sapiens

<400> SEQUENCE: 3
caggtgcagc tggtgcagtc tggagctgag gtgaagaagc ccggggcctc agtgaaggtc    60
tcctgcaagg cttctggtta cacgtttaac agctatggaa tcagttgggt gcgacaggcc   120
cccggacaag gcttgagtg gatgggatgg atcagcgctt acactggcga cacaaagttt    180
gcacagaatg tgcagggcag agtcaccatg accatagaca tccacgag  taccgcctac    240 atggaactga ggagcctgag atctgacgac acggccgtat attactgtgc gagacattac   300
ctccaagggg tagtagtggt tgaccccta c tcccacgcta tggacgtctg gggccaaggg   360
accacggtca ccgtctcctc a                                             381

<210> SEQ ID NO 4
<211> LENGTH: 337
<212> TYPE: DNA
<213> ORGANISM: Homo sapiens

<400> SEQUENCE: 4
gatgttgtga tgactcagtc tccactctcc ttgcccgtca cccttggcca gccggcctcc    60
atctcctgca ggtctagtca aagcctcgta tacagtgatg agacacctt cctggaatgg   120 tttcagcaga ggccaggcca atctccaagg cgcctaattt ataaggtttc taaccgggat   180
tctggggtcc cagacagatt cagcggcagt gggtcaggca ctgatttcac actgaaaatc   240
agcagggtgg aggctgagga tgttgggctt tattactgca tgcaacatac acactggccg   300
```

```
cacactttg gccaggggac caaggtggag atcaaac                                 337
```

<210> SEQ ID NO 5
<211> LENGTH: 331
<212> TYPE: DNA
<213> ORGANISM: Homo sapiens

<400> SEQUENCE: 5

```
gaaattgtgt tgacacagtc tccagccacc ctgtctttgt ctccaggaga aagagtcacc        60
ctctcctgca gggccagtga gagtgttggc aacaagttag cctggttcca acagaggcct       120
ggccaggctc ccaggctcct catttataat gcatccaaca gggccactga catcccagcc       180
aggttcagtg gcagtgggtc tgggacagac ttcactctca ccatcagcag cctgcagcct       240
gaagattttg cagtttatta ctgtcagcag cgtggcacgt ggcctcgggg cctcatcacc       300
ttcggccaag ggacacgact ggagattaaa c                                      331
```

<210> SEQ ID NO 6
<211> LENGTH: 325
<212> TYPE: DNA
<213> ORGANISM: Homo sapiens

<400> SEQUENCE: 6

```
gaaattgtgt tgacgcagtc tccaggcacc ctgtctttct ttccagggga aagagccacc        60
ctctcctgca gggccagtca aactattaac agcagattct agcctggta tcagcagaaa       120 cctggccagg ctcccaggct cctcatctat ggtgcatcca gcgggccac tggcatcccg        180 gacaggttca gtggccgtgg gtctgggaca gacttcactc tcgccatcag cagactggag       240
cctgaggatt ttgcagtgta ttactgtcag ttgtatggta gctcacggac gacttttggc       300
cagggaccaa ggtggagat caaac                                              325
```

<210> SEQ ID NO 7
<211> LENGTH: 118
<212> TYPE: PRT
<213> ORGANISM: Homo sapiens

<400> SEQUENCE: 7

```
Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Thr Pro
            20                  25                  30

Trp Met Thr Trp Ile Arg Gln Ala Pro Gly Lys Gly Leu Glu Trp Val
        35                  40                  45

Ala His Ile Lys Gln Asp Gly Ser Glu Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Leu Tyr Tyr Cys
                85                  90                  95

Ala Arg Met Thr Arg Glu Ser Ser Glu Asn Tyr Trp Gly Gln Gly Thr
            100                 105                 110

Leu Val Thr Val Ser Ser
        115
```

<210> SEQ ID NO 8
<211> LENGTH: 125
<212> TYPE: PRT

```
<213> ORGANISM: Homo sapiens

<400> SEQUENCE: 8

Gln Val Gln Leu Val Gln Ser Gly Pro Glu Met Lys Lys Pro Gly Ala
1               5                   10                  15

Ser Val Lys Val Ser Cys Lys Thr Ser Gly Tyr Arg Phe Thr Arg Tyr
                20                  25                  30

Gly Ile Ser Trp Val Arg Gln Ala Pro Gly Arg Gly Leu Glu Trp Leu
            35                  40                  45

Gly Trp Ile Ser Ala Tyr Ser Gly Asp Thr Tyr Tyr Gly Gln Lys Phe
        50                  55                  60

Gln Asp Arg Val Thr Met Thr Thr Asp Arg Ala Thr Ser Thr Ala Tyr
65                  70                  75                  80

Met Glu Leu Arg Asn Leu Gly Ser Asp Ser Ala Val Tyr Phe Cys
                85                  90                  95

Ala Arg Asp His Val Gln Gly Glu Val Ser Ile Tyr Tyr Tyr Ala Met
            100                 105                 110

Asp Val Trp Gly Glu Gly Thr Thr Val Thr Val Ser Ser
        115                 120                 125

<210> SEQ ID NO 9
<211> LENGTH: 127
<212> TYPE: PRT
<213> ORGANISM: Homo sapiens

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Thr Gly Asp Thr Lys Phe Ala Gln Asn Val
        50                  55                  60

Gln Gly Arg Val Thr Met Thr Ile Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Tyr Leu Gln Gly Val Val Val Asp Pro Tyr Ser His
            100                 105                 110

Ala Met Asp Val Trp Gly Gln Gly Thr Thr Val Thr Val Ser Ser
        115                 120                 125

<210> SEQ ID NO 10
<211> LENGTH: 112
<212> TYPE: PRT
<213> ORGANISM: Homo sapiens

<400> SEQUENCE: 10

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
                20                  25                  30

Asp Gly Asp Thr Phe Leu Glu Trp Phe Gln Gln Arg Pro Gly Gln Ser
            35                  40                  45

Pro Arg Arg Leu Ile Tyr Lys Val Ser Asn Arg Asp Ser Gly Val Pro
        50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln His
                85                  90                  95

Thr His Trp Pro His Thr Phe Gly Gln Gly Thr Lys Val Glu Ile Lys
            100                 105                 110

<210> SEQ ID NO 11
<211> LENGTH: 110
<212> TYPE: PRT
<213> ORGANISM: Homo sapiens

<400> SEQUENCE: 11

Glu Ile Val Leu Thr Gln Ser Pro Ala Thr Leu Ser Leu Ser Pro Gly
1               5                   10                  15

Glu Arg Val Thr Leu Ser Cys Arg Ala Ser Glu Ser Val Gly Asn Lys
                20                  25                  30

Leu Ala Trp Phe Gln Gln Arg Pro Gly Gln Ala Pro Arg Leu Leu Ile
            35                  40                  45

Tyr Asn Ala Ser Asn Arg Ala Thr Asp Ile Pro Ala Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Arg Gly Thr Trp Pro Arg
                85                  90                  95

Gly Leu Ile Thr Phe Gly Gln Gly Thr Arg Leu Glu Ile Lys
            100                 105                 110

<210> SEQ ID NO 12
<211> LENGTH: 108
<212> TYPE: PRT
<213> ORGANISM: Homo sapiens

<400> SEQUENCE: 12

Glu Ile Val Leu Thr Gln Ser Pro Gly Thr Leu Ser Phe Phe Pro Gly
1               5                   10                  15

Glu Arg Ala Thr Leu Ser Cys Arg Ala Ser Gln Thr Ile Asn Ser Arg
                20                  25                  30

Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

Gly Arg Gly Ser Gly Thr Asp Phe Thr Leu Ala Ile Ser Arg Leu Glu
65                  70                  75                  80

Pro Glu Asp Phe Ala Val Tyr Tyr Cys Gln Leu Tyr Gly Ser Ser Arg
                85                  90                  95

Thr Thr Phe Gly Gln Gly Thr Lys Val Glu Ile Lys
            100                 105

<210> SEQ ID NO 13
<211> LENGTH: 8
<212> TYPE: PRT
<213> ORGANISM: Homo sapiens

<400> SEQUENCE: 13

Gly Phe Thr Phe Ser Thr Pro Trp
1               5

```
<210> SEQ ID NO 14
<211> LENGTH: 8
<212> TYPE: PRT
<213> ORGANISM: Homo sapiens

<400> SEQUENCE: 14

Ile Lys Gln Asp Gly Ser Glu Thr
1               5

<210> SEQ ID NO 15
<211> LENGTH: 11
<212> TYPE: PRT
<213> ORGANISM: Homo sapiens

<400> SEQUENCE: 15

Ala Arg Met Thr Arg Glu Ser Ser Glu Asn Tyr
1               5                   10

<210> SEQ ID NO 16
<211> LENGTH: 8
<212> TYPE: PRT
<213> ORGANISM: Homo sapiens

<400> SEQUENCE: 16

Gly Tyr Arg Phe Thr Arg Tyr Gly
1               5

<210> SEQ ID NO 17
<211> LENGTH: 8
<212> TYPE: PRT
<213> ORGANISM: Homo sapiens

<400> SEQUENCE: 17

Ile Ser Ala Tyr Ser Gly Asp Thr
1               5

<210> SEQ ID NO 18
<211> LENGTH: 18
<212> TYPE: PRT
<213> ORGANISM: Homo sapiens

<400> SEQUENCE: 18

Ala Arg Asp His Val Gln Gly Glu Val Ser Ile Tyr Tyr Tyr Ala Met
1               5                   10                  15

Asp Val

<210> SEQ ID NO 19
<211> LENGTH: 8
<212> TYPE: PRT
<213> ORGANISM: Homo sapiens

<400> SEQUENCE: 19

Gly Tyr Thr Phe Asn Ser Tyr Gly
1               5

<210> SEQ ID NO 20
<211> LENGTH: 8
<212> TYPE: PRT
<213> ORGANISM: Homo sapiens

<400> SEQUENCE: 20

Ile Ser Ala Tyr Thr Gly Asp Thr
1               5
```

```
<210> SEQ ID NO 21
<211> LENGTH: 20
<212> TYPE: PRT
<213> ORGANISM: Homo sapiens

<400> SEQUENCE: 21

Ala Arg His Tyr Leu Gln Gly Val Val Val Asp Pro Tyr Ser His
1               5                   10                  15

Ala Met Asp Val
            20

<210> SEQ ID NO 22
<211> LENGTH: 11
<212> TYPE: PRT
<213> ORGANISM: Homo sapiens

<400> SEQUENCE: 22

Gln Ser Leu Val Tyr Ser Asp Gly Asp Thr Phe
1               5                   10

<210> SEQ ID NO 23
<211> LENGTH: 3
<212> TYPE: PRT
<213> ORGANISM: Homo sapiens

<400> SEQUENCE: 23

Lys Val Ser
1

<210> SEQ ID NO 24
<211> LENGTH: 9
<212> TYPE: PRT
<213> ORGANISM: Homo sapiens

<400> SEQUENCE: 24

Met Gln His Thr His Trp Pro His Thr
1               5

<210> SEQ ID NO 25
<211> LENGTH: 6
<212> TYPE: PRT
<213> ORGANISM: Homo sapiens

<400> SEQUENCE: 25

Glu Ser Val Gly Asn Lys
1               5

<210> SEQ ID NO 26
<211> LENGTH: 3
<212> TYPE: PRT
<213> ORGANISM: Homo sapiens

<400> SEQUENCE: 26

Asn Ala Ser
1

<210> SEQ ID NO 27
<211> LENGTH: 12
<212> TYPE: PRT
<213> ORGANISM: Homo sapiens

<400> SEQUENCE: 27

Gln Gln Arg Gly Thr Trp Pro Arg Gly Leu Ile Thr
1               5                   10
```

<210> SEQ ID NO 28
<211> LENGTH: 7
<212> TYPE: PRT
<213> ORGANISM: Homo sapiens

<400> SEQUENCE: 28

Gln Thr Ile Asn Ser Arg Phe
1               5

<210> SEQ ID NO 29
<211> LENGTH: 3
<212> TYPE: PRT
<213> ORGANISM: Homo sapiens

<400> SEQUENCE: 29

Gly Ala Ser
1

<210> SEQ ID NO 30
<211> LENGTH: 9
<212> TYPE: PRT
<213> ORGANISM: Homo sapiens

<400> SEQUENCE: 30

Gln Leu Tyr Gly Ser Ser Arg Thr Thr
1               5

<210> SEQ ID NO 31
<211> LENGTH: 88
<212> TYPE: DNA
<213> ORGANISM: Artificial sequence
<220> FEATURE:
<223> OTHER INFORMATION: DNA primer

<400> SEQUENCE: 31
tcgacctccg aagttggggg ggagcaaaag caggggaaaa taaaaacaac caaaatgaac      60
actcaaatcc tggtattcgc tctgattg                                        88

<210> SEQ ID NO 32
<211> LENGTH: 100
<212> TYPE: DNA
<213> ORGANISM: Artificial sequence
<220> FEATURE:
<223> OTHER INFORMATION: DNA primer

<400> SEQUENCE: 32
ttttgggccg ccgggttatt agtagaaaca agggtgtttt cctcatatt tctgaaattc       60 taatcttata tacaaatagt gcaccgcatg tttccattct                           100

<210> SEQ ID NO 33
<211> LENGTH: 372
<212> TYPE: DNA
<213> ORGANISM: Homo sapiens

<400> SEQUENCE: 33
gaggtgcagc tggtggagtc tgaggaggc ttgataaacc ctgggggtc cctgagactc       60 tcctgtgcag cctctggttt caacatcgat aacaaccaaa tgatttgggt ccgccaggct    120
ccaaagaagg gcctggagtg ggtctcactt atttatagcg gtggttctac atattccgca    180
gacaccgtga agggccgatt caccatctcc agagacaatt ccaagaacac agtgtatctt    240
cacatgaaca gtctgcgagc cgaggacacg gccgtgtatt attgtgcgag agattttctc    300

```
agggggaccaa tacatgatta cttttttctac atggacgtct ggggcaaggg gaccacggtc    360
accgtctcct ca                                                          372
```

<210> SEQ ID NO 34
<211> LENGTH: 319
<212> TYPE: DNA
<213> ORGANISM: Homo sapiens

<400> SEQUENCE: 34

```
gaaattgtgt tgacacagtc tccagcctcc ctgtctttgt ctccagggga aagagccacc     60
ctctcctgca gggccagtca gagggttgac agctccatag ctggtaccg acacaaacct    120 ggtcaggctc ccaggctcct catctatgat gcaattaaaa gggccactgg catcccagcc    180
agattcagtg gcagtggata tgggacagac ttcactctta ccatcagccg cctagaggct    240
gaagattttg cagtttatta ctgtcagcag cgtagcacct ggcccacttt cggccctggg    300
accaaagtgg atatcaaac                                                 319
```

<210> SEQ ID NO 35
<211> LENGTH: 124
<212> TYPE: PRT
<213> ORGANISM: Homo sapiens

<400> SEQUENCE: 35

```
Glu Val Gln Leu Val Glu Ser Gly Gly Gly Leu Ile Asn Pro Gly Gly
1               5                   10                  15

Ser Leu Arg Leu Ser Cys Ala Ala Ser Gly Phe Asn Ile Asp Asn Asn
            20                  25                  30

Gln Met Ile Trp Val Arg Gln Ala Pro Lys Lys Gly Leu Glu Trp Val
        35                  40                  45

Ser Leu Ile Tyr Ser Gly Gly Ser Thr Tyr Ser Ala Asp Thr Val Lys
    50                  55                  60

Gly Arg Phe Thr Ile Ser Arg Asp Asn Ser Lys Asn Thr Val Tyr Leu
65                  70                  75                  80

His Met Asn Ser Leu Arg Ala Glu Asp Thr Ala Val Tyr Tyr Cys Ala
                85                  90                  95

Arg Asp Phe Leu Arg Gly Pro Ile His Asp Tyr Phe Phe Tyr Met Asp
            100                 105                 110

Val Trp Gly Lys Gly Thr Thr Val Thr Val Ser Ser
        115                 120
```

<210> SEQ ID NO 36
<211> LENGTH: 106
<212> TYPE: PRT
<213> ORGANISM: Homo sapiens

<400> SEQUENCE: 36

```
Glu Ile Val Leu Thr Gln Ser Pro Ala Ser Leu Ser Leu Ser Pro Gly
1               5                   10                  15

Glu Arg Ala Thr Leu Ser Cys Arg Ala Ser Gln Arg Val Asp Ser Ser
            20                  25                  30

Ile Gly Trp Tyr Arg His Lys Pro Gly Gln Ala Pro Arg Leu Leu Ile
        35                  40                  45

Tyr Asp Ala Ile Lys Arg Ala Thr Gly Ile Pro Ala Arg Phe Ser Gly
    50                  55                  60

Ser Gly Tyr Gly Thr Asp Phe Thr Leu Thr Ile Ser Arg Leu Glu Ala
65                  70                  75                  80
```

Glu Asp Phe Ala Val Tyr Tyr Cys Gln Gln Arg Ser Thr Trp Pro Thr
            85                  90                  95

Phe Gly Pro Gly Thr Lys Val Asp Ile Lys
            100                 105

<210> SEQ ID NO 37
<211> LENGTH: 8
<212> TYPE: PRT
<213> ORGANISM: Homo sapiens

<400> SEQUENCE: 37

Gly Phe Asn Ile Asp Asn Asn Gln
1               5

<210> SEQ ID NO 38
<211> LENGTH: 7
<212> TYPE: PRT
<213> ORGANISM: Homo sapiens

<400> SEQUENCE: 38

Ile Tyr Ser Gly Gly Ser Thr
1               5

<210> SEQ ID NO 39
<211> LENGTH: 18
<212> TYPE: PRT
<213> ORGANISM: Homo sapiens

<400> SEQUENCE: 39

Ala Arg Asp Phe Leu Arg Gly Pro Ile His Asp Tyr Phe Phe Tyr Met
1               5                   10                  15

Asp Val

<210> SEQ ID NO 40
<211> LENGTH: 6
<212> TYPE: PRT
<213> ORGANISM: Homo sapiens

<400> SEQUENCE: 40

Gln Arg Val Asp Ser Ser
1               5

<210> SEQ ID NO 41
<211> LENGTH: 3
<212> TYPE: PRT
<213> ORGANISM: Homo sapiens

<400> SEQUENCE: 41

Asp Ala Ile
1

<210> SEQ ID NO 42
<211> LENGTH: 8
<212> TYPE: PRT
<213> ORGANISM: Homo sapiens

<400> SEQUENCE: 42

Gln Gln Arg Ser Thr Trp Pro Thr
1               5

UNITED STATES PATENT AND TRADEMARK OFFICE
CERTIFICATE OF CORRECTION

PATENT NO. : 10,357,563 B2
APPLICATION NO. : 15/536857
DATED : November 15, 2016
INVENTOR(S) : Patrick Wilson and Carole J. Henry Dunand It is certified that error appears in the above-identified patent and that said Letters Patent is hereby corrected as shown below:

Column 1, at Line 13 please insert the following:
-- STATEMENT REGARDING FEDERAL FUNDING
This invention was made with government support under contracts AI008724, HHSN272201400005C, AI057158, AI057266, AI090023, AI097092, AI109946 and HHSN272201400006C awarded by the National Institutes of Health. The government has
certain rights in the invention. --

Signed and Sealed this
Seventh Day of January, 2020

Andrei Iancu
*Director of the United States Patent and Trademark Office*